US011866504B2

(12) United States Patent
Kershaw et al.

(10) Patent No.: US 11,866,504 B2
(45) Date of Patent: Jan. 9, 2024

(54) BISPECIFIC POLYPEPTIDES FOR ENGAGEMENT OF CAR EXPRESSING IMMUNE CELLS WITH ANTIGEN PRESENTING CELLS AND USES THEREOF

(71) Applicant: Peter MacCallum Cancer Institute, Melbourne (AU)

(72) Inventors: Michael Kershaw, Ocean Gove (AU); Clare Slaney, Greensborough (AU); Bianca Von Scheidt, Ascot Vale (AU)

(73) Assignee: Peter MacCallum Cancer Institute, Melbourne (AU)

( * ) Notice: Subject to any disclaimer, the term of this patent is extended or adjusted under 35 U.S.C. 154(b) by 0 days.

(21) Appl. No.: 17/289,997

(22) PCT Filed: Oct. 29, 2019

(86) PCT No.: PCT/AU2019/051189
§ 371 (c)(1),
(2) Date: Apr. 29, 2021

(87) PCT Pub. No.: WO2020/087116
PCT Pub. Date: May 7, 2020

(65) Prior Publication Data
US 2022/0017628 A1 Jan. 20, 2022

(30) Foreign Application Priority Data

Oct. 30, 2018 (AU) .............................. 2018904117
Sep. 4, 2019 (AU) .............................. 2019903255

(51) Int. Cl.
| | | |
|---|---|---|
| *C07K 16/28* | (2006.01) | |
| *A61P 35/00* | (2006.01) | |
| *A61K 35/17* | (2015.01) | |
| *A61K 39/395* | (2006.01) | |
| *C07K 16/24* | (2006.01) | |
| *C07K 16/32* | (2006.01) | |
| *A61K 39/00* | (2006.01) | |

(52) U.S. Cl.
CPC .......... *C07K 16/2878* (2013.01); *A61K 35/17* (2013.01); *A61K 39/3955* (2013.01); *A61P 35/00* (2018.01); *C07K 16/247* (2013.01); *C07K 16/2809* (2013.01); *C07K 16/32* (2013.01); *A61K 2039/505* (2013.01); *C07K 2317/31* (2013.01); *C07K 2317/622* (2013.01); *C07K 2319/33* (2013.01)

(58) Field of Classification Search
CPC ... A61P 35/00; C07K 14/7051; C07K 16/247; C07K 16/2809; C07K 16/2833; C07K 16/2878; C07K 16/32; C07K 16/44; C07K 16/468; C07K 2317/31; C07K 2317/622; C07K 2319/03; C07K 2319/33; C12N 2510/00; C12N 5/0638

USPC ...................................... 424/93.21; 514/44 R
See application file for complete search history.

(56) References Cited

U.S. PATENT DOCUMENTS

2018/0021440 A1* 1/2018 Yu ...................... C07K 16/3069
424/178.1

FOREIGN PATENT DOCUMENTS

| WO | WO 2016/180948 A1 | 11/2016 | | |
|---|---|---|---|---|
| WO | WO 2017/167919 A1 | 10/2017 | | |
| WO | WO 2017/177337 A1 | 10/2017 | | |
| WO | WO-2017177337 A1 * | 10/2017 | ............. | A61K 35/17 |
| WO | WO-2020028444 A1 * | 2/2020 | ........... | A61K 31/496 |

OTHER PUBLICATIONS

Currus Biologics (2016) https://uniseed.com/project/currus-biologics/, pp. 1-3. (Year: 2016).*
Lu et al. AACR Annual Meeting Apr. 14-18, 2018; Chicago, IL. (See IDS Apr. 29, 2021) (Year: 2018).*
Ma et al. (Oncology Reports vol. 34: 2567-2575, 2015) (See IDS Apr. 29, 2021) (Year: 2015).*
Slaney et al. Jul. 2018 Cancer Discovery 8(8) pp. 0F1-0F11. DOI:10.1158/2159-8290.CD-18-0297 (Year: 2018).*
Wing et al. Cancer Immunol Res. May 2018;6(5):605-616. doi: 10.1158/2326-6066.CIR-17-0314. Epub Mar. 27, 2018. (Year: 2018).*
Shen et al., Prosthetic antigen receptors. J American Chemical Society. 2015;137(32):10108-10111.
International Search Report and Written Opinion dated Dec. 9, 2019 for Application No. PCT/AU2019/051189.
Lu et al., Adaptor controlled CAR-T cell immunotherapy for treatment of folate receptor-alpha/beta positive solid and liquid tumors. Cancer Research. Abstract LB-109:, 2018;doi:10.1158/1538-7445.am2018-LP-109.
Ma et al., Anti-CD3 × EGFR bispecific antibody redirects cytokine-induced killer cells to glioblastoma in vitro and in vivo. Oncology Reports. 2015;34:2567-2575, doi:10.3892/or.2015.4233.

(Continued)

*Primary Examiner* — Janet L Epps-Smith
(74) *Attorney, Agent, or Firm* — Wolf, Greenfield & Sacks, P.C.

(57) ABSTRACT

The present application is directed to bispecific polypeptides comprising a first domain binding an antigen on an antigen presenting cell (ARC) and a second domain binding an antigen on an immune cell expressing a chimeric antigen receptor (CAR). Nucleic acids, vectors and host cells used in producing the polypeptide of the invention are also disclosed. Compositions comprising the bispecific polypeptides and methods of treating cancer and stimulating activation and expansion of immune cells in vivo and in vitro are also disclosed.

16 Claims, 23 Drawing Sheets
Specification includes a Sequence Listing.

(56) References Cited

OTHER PUBLICATIONS

Rennert et al., CAR19 T cells secreting antigen-retargeting fusion proteins have remarkable potency against diverse tumor types. Cancer Research. Abstract 2569, 2018;doi: 10.1158/1538-7445. AM2018-2569.

Shalabi et al., Case report: Impact of BITE on CAR-T cell expansion. Adv Cell Gene Ther. 2019;2:e50,doi:10.1002/acg2.50.

Von Scheidt et al., Enterotoxins can support CAR T cells against solid tumors. PNAS. 2019; 116(50):25229-25235.

Strohl et al., Bispecific T-Cell Redirection versus Chimeric Antigen Receptor (CAR)-T Cells as Approaches to Kill Cancer Cells. Antibodies (Basel). Jul. 3, 2019;8(3):41. doi: 10.3390/antib8030041. PMID: 31544847; PMCID: PMC6784091.

* cited by examiner

Gel1

Cell homoginizer
(0.75% Supe +cells from a 6-well plate)        Supe (0.75% Supe)

| Cell homo (Beat1) | Cell homo (Beat2) | Control homo | Cell supe (Beat1) | Cell supe (Beat2) | |
|---|---|---|---|---|---|
| 3ul 6ul 12 ul | 3ul 6ul 12 ul | | 3ul 6ul 12ul | 3u 6ul 12 ul | + |

Ladder

Gel2 Cell pellets (1/16 cells from a 6-well plate)

| Cell pellet (Beat1) | Cell pellet (Beat2) | Control Pellet |
|---|---|---|
| 3ul 6ul 12 ul | 3ul 6ul 12 ul | + |

A. Cell Proliferation

B. IFN-γ secretion

C. % TCRVβ8+ T cells in the spleen

A

B

C

D

A

CAR

B

CAR+SEB

BISPECIFIC POLYPEPTIDES FOR ENGAGEMENT OF CAR EXPRESSING IMMUNE CELLS WITH ANTIGEN PRESENTING CELLS AND USES THEREOF

RELATED APPLICATIONS

This application is a national stage filing under 35 U.S.C. § 371 of international application number PCT/AU2019/051189, filed Oct. 29, 2019, which claims the benefit of Australian application number 2018904117, filed Oct. 30, 3018 and Australian application number 2019903255, filed Sep. 4, 2019, each of which is herein incorporated by reference in its entirety.

FIELD

The present disclosure relates generally to a bispecific polypeptide, including parts and uses thereof, comprising a first binding domain, which is capable of binding an antigen presenting cell (APC) and a second binding domain, which is capable of binding to a T cell.

RELATED APPLICATIONS

This application claims priority from Australian Provisional Patent Application No. 2018904117 filed 30 Oct. 2018 and Australian Provisional Application No. 2019903255 filed 4 Sep. 2019, the entire contents of which are hereby incorporated by reference.

BACKGROUND

Adoptive cell transfer (ACT) is demonstrating exciting potential for cancer treatment. In ACT, large numbers of autologous tumor-reactive T cells are generated in vitro before reinfusion to patients. Tumour-reactive T cells can be isolated from blood or tumors and expanded in vitro using stimulation with peptides and/or cytokines. The most impressive responses to ACT to date have been in specific tumor types, such as melanoma, where T cell transfer, together with administration of IL-2 and a preconditioning regimen involving chemotherapy and/or total body irradiation, resulted in an objective response rate observed in 52 of 93 patients (56%), with 20 of 93 patients achieving complete responses and 19 of those 20 patients with ongoing durable complete responses in excess of 5 years post treatment (Hinrichs et al., 2014, *Immunology Reviews*, 257(1):56-71). Patients with Epstein-Barr Virus (EBV)-associated lymphoproliferative disorders following bone marrow transplant can also benefit from ACT, with virtually all patients achieving complete resolution of disease after adoptive transfer of EBC-specific T cells (Heslop et al., 2010, *Blood*, 115(5): 925-35). However, isolation of autologous T cells with reactivity against other cancer types is rare.

Methods to improve the reactivity of T cells for ACT include the genetic modification of patient lymphocytes to generate tumor-reactive T cells against most malignancies, including solid cancers and those of the blood. Two main approaches of genetic modification involve genes encoding T cell receptor (TCR) or a chimeric antigen receptor (CAR). A CAR consists of an antibody-derived domain fused with T cell signaling domains that redirects the effector function of T cells against tumor cells. Both approaches can render the T cells tumor-reactive, but the CAR approach, being non-MHC-restricted, is more widely applicable to a broader range of patients.

CARs can take various forms (Kershaw et al., 2013, *Nature Reviews Cancer*, 13(8):525-41), but are typically composed of an extracellular domain consisting of a single-chain variable fragment (scFv) of an antibody specific for a tumour-associated antigen (TAA). This scFv is linked, via hinge and transmembrane domains, to an intracellular region composed of one or more signaling moieties. CARs have been developed with specificity for a range of TAA, including Her2, CEA, FBP, CD19 and CD209. The most advanced clinical studies have utilized CARs specific for CD19 for the treatment of B cell leukemia and lymphomas (Kershaw et al., 2013, supra). In 2017, two of these CD19-CAR T cell therapies were approved by the US FDA for the treatment of B-cell malignancies (Kymriah, Novartis and Yescarta, Kite Pharma/Gilead). Despite these results, objective responses reported for solid tumors have been less frequent, which may be due to insufficient activation, expansion and persistence of CAR T cells and/or the immunosuppressive tumor microenvironment.

Attempts to optimize this type of therapy have led to combining CAR T cells with other therapeutic approaches designed to overcome tumour-induced immunosuppression including co-treatment with α-PD-1 monoclonal antibody (John et al., 2013, *Clinical Cancer Research*, 19:5636-46), genetic modification of signaling and cytokine pathways (Koneru et al., 2015, *Oncoimmunology*, 4:e994446), and the use of adjuvants, such as agonistic α-4-1BB monoclonal antibodies (mAB) (Mardiana et al., 2017, *Cancer Research*) and Bispecific T Cell Engagers (BiTEs). While some of these approaches have proved successful in enabling a direct interaction between T cells and cancer cells, which can lead to T cell expansion in hematopoietic cancer cells, significant expansion in solid cancer setting is rarely observed (Huehls et al., 2015, *Immunological Cell Biology*, 93(3):290-6).

Optimization of therapeutic approaches for the delivery of CAR T cells is often exacerbated by difficulties faced in the expansion and manufacture of CAR T cells in vitro due to low lymphocyte counts and poor condition of cells from heavily treated patients (U.S. Food & Drug Administration: KYMRIAH (tisagenlecleucel), 30 Aug. 2017). Furthermore, even where sufficient donor cells are available, a significant number of cells are required to be manufactured in order to provide an effective dose of these therapies to patients, while allogeneic cells from healthy donors have been suggested as a solution to this problem, there are a number of issues, such as human leucocyte antigen (HLA) mismatch between the donor and recipient, which can lead to Graft vs. Host Disease (GvHD). There remains, therefore, an urgent need for the development of new reagents to improve the in vitro and in vivo expansion of CAR T cells for ACT.

SUMMARY

In an aspect disclosed herein, there is provided a bispecific polypeptide comprising a first binding domain and a second binding domain, wherein the first binding domain is an antibody or an antibody fragment that specifically binds to an antigen expressed on an antigen presenting cell (APC), preferably a professional APC, and wherein the second binding domain is an antibody or an antibody fragment that specifically binds to an antigen on an immune cell that expresses a chimeric antigen receptor (CAR).

In an aspect disclosed herein, there is provided a bispecific polypeptide comprising a first binding domain and a second binding domain, wherein the first binding domain is an antibody or an antibody fragment that specifically binds to an antigen expressed on an antigen presenting cell (APC), and wherein the second binding domain is an antibody or an antibody fragment that specifically binds to a chimeric antigen receptor (CAR) expressed by an immune cell.

In another aspect disclosed herein, there is provided a nucleic acid encoding the bispecific polypeptide as described herein.

In another aspect disclosed herein, there is provided a vector comprising the nucleic acid sequence as described herein operably linked to a regulatory sequence.

In another aspect disclosed herein, there is provided a cell comprising the vector as described herein.

In another aspect disclosed herein, there is provided a method for producing a bispecific polypeptide comprising: (i) culturing a cell as described herein in a culture medium and under conditions suitable for the expression of the bispecific polypeptide; and (i) isolating the expressed bispecific polypeptide from the cell or from the culture medium.

In another aspect disclosed herein, there is provided a pharmaceutical composition comprising a bispecific polypeptide as described herein and a pharmaceutically acceptable carrier.

In another aspect disclosed herein, there is provided a method for the treatment of cancer comprising co-administering to the subject in need thereof a therapeutically effective amount of: (i) an immune cell expressing a CAR; and (ii) a bispecific polypeptide or pharmaceutical composition as described herein, and wherein the bispecific polypeptide simultaneously binds to an antigen expressed on an endogenous APC of the subject and an antigen on the immune cell, preferably wherein the antigen on the immune cell is an antigen on the CAR, thereby stimulating the activation and expansion of the immune cell in vivo for the treatment of cancer.

In another aspect disclosed herein, there is provided a method for stimulating the activation and expansion of an immune cell in vivo comprising co-administering to a subject an effective amount of (i) an immune cell expressing a CAR; and (ii) a bispecific polypeptide or a pharmaceutical composition as described herein to the subject, wherein the bispecific polypeptide simultaneously binds to an antigen expressed on an endogenous APC of the subject and an antigen on the immune cell, preferably wherein the antigen on the immune cell is an antigen on the CAR, thereby stimulating the activation and expansion of the immune cell in vivo.

In another aspect disclosed herein, there is provided a method for stimulating the activation and expansion of an immune cell in vitro comprising culturing an isolated immune cell expressing a CAR in a culture medium comprising (i) an APC or APC mimetic, and (ii) a bispecific polypeptide as described herein, wherein the bispecific polypeptide simultaneously binds to the antigen expressed on the APC or APC mimetic and an antigen on the immune cell, preferably wherein the antigen on the immune cell is an antigen on the CAR, thereby stimulating the activation and expansion of the immune cell in vitro.

In another aspect disclosed herein, there is provided a use of the bispecific polypeptide or the pharmaceutical composition as described herein in the manufacture of a medicament for the treatment of cancer.

In a further aspect, there is provided a bispecific polypeptide or a pharmaceutical composition as herein described, for use in the treatment of cancer.

In a further aspect, the invention provides a kit or article of manufacture including one or more bispecific polypeptides of the invention, a nucleic acid encoding said bispecific polypeptide and/or pharmaceutical compositions as described above.

In other aspects there is provided a kit for use in a therapeutic application mentioned above, the kit comprising:
(a) a container holding a bispecific polypeptide, nucleic acid, vector or pharmaceutical composition of the invention; and
(b) a label or package insert with instructions for use.

In certain embodiments the kit may also comprise one or more active principles or ingredients for treatment of cancer. For example, the kit may also comprise an immune cell expressing a CAR.

DETAILED DESCRIPTION

Figure 1:
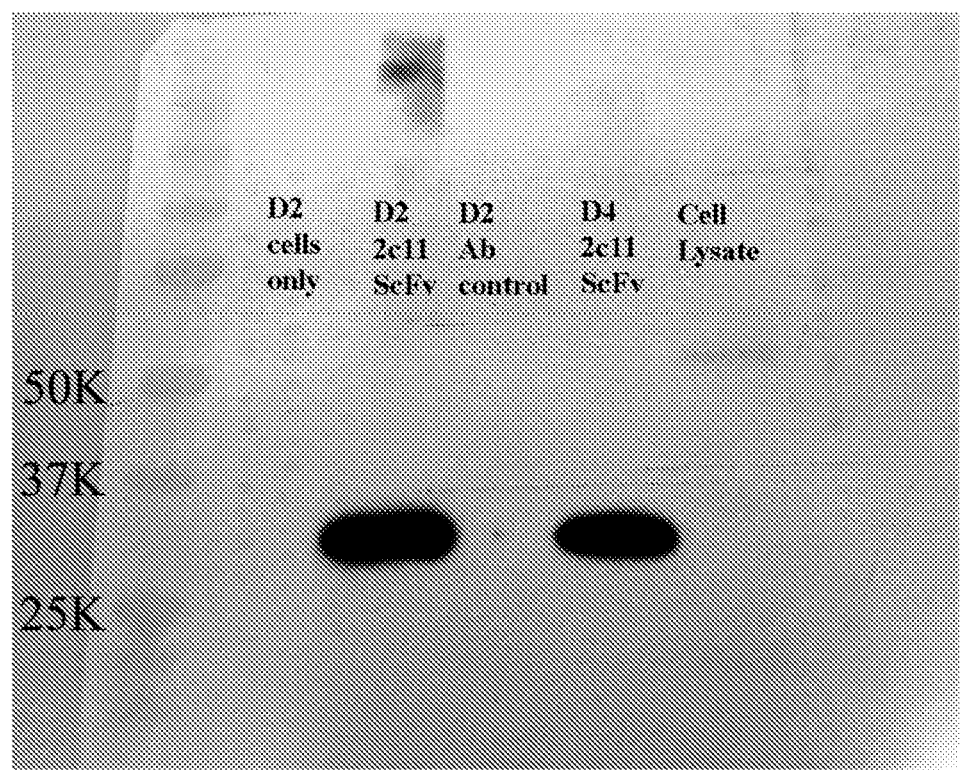
FIG. 1 shows that a binding domain specific for an antigen on a CAR T cell can be expressed using the Expi293 cell expression system.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The reference in this specification to any prior publication (or information derived from it), or to any matter which is known, is not, and should not be taken as an acknowledgement or admission or any form of suggestion that that prior publication (or information derived from it) or known matter forms part of the common general knowledge in the field of endeavor to which this specification relates.

Unless specifically defined otherwise, all technical and scientific terms used herein shall be taken to have the same meaning as commonly understood by one of ordinary skill in the art.

Unless otherwise indicated the molecular biology, cell culture and laboratory techniques utilized in the present specification are standard procedures, well known to those skilled in the art. Such techniques are described and explained throughout the literature in sources such as, J. Perbal, *A Practical Guide to Molecular Cloning*, John Wiley and Sons (1984), J. Sambrook et al., *Molecular Cloning: A Laboratory Manual*, Cold Spring Harbor Laboratory Press (1989), T. A. Brown (editor), *Essential Molecular Biology: A Practical Approach*, Volumes 1 and 2, IRL Press (1991), D. M. Glover and B. D. Hames (editors), *DNA Cloning: A Practical Approach*, Volumes 1-4, IRL Press (1995 and 1996), and F. M. Ausubel et al. (editors), *Current Protocols in Molecular Biology*, Greene Pub; all of which are incorporated by reference. The procedures described are believed to be well known in the art and are provided for the convenience of the reader. All other publications mentioned in this specification are also incorporated by reference in their entirety.

As used in the subject specification, the singular forms "a", "an" and "the" include plural aspects unless the context clearly dictates otherwise. Thus, for example, reference to "a polypeptide" includes a single polypeptide, as well as two or more polypeptides; reference to "an antigen presenting cell (APC)" includes a single APC, as well as two or more APCs; and so forth.

Amino acid and nucleotide sequences are referred to by sequence identifier numbers (SEQ ID NO), as shown in Table 1, below.

TABLE 1

| SEQ ID NO | Name | Sequence Type |
|---|---|---|
| 1 | CD40 scFv | Nucleic acid |
| 2 | CD40 scFv | Amino acid |
| 3 | MHCII scFv | Nucleic acid |
| 4 | MHCII scFv | Amino acid |
| 5 | CD3 scFv | Nucleic acid |
| 6 | CD3 scFv | Amino acid |
| 7 | c-myc-tag scFv | Nucleic acid |
| 8 | c-myc-tag scFv | Amino acid |
| 9 | Linker 1 | Nucleic acid |
| 10 | Linker 1 | Amino acid |
| 11 | Linker 2 | Nucleic acid |
| 12 | Linker 2 | Amino acid |
| 13 | Linker 3 | Nucleic acid |
| 14 | Linker 3 | Amino acid |
| 15 | CD40/c-myc-tag (BEAT1) | Nucleic acid |
| 16 | BEAT1 | Amino acid |
| 17 | MHCII/c-myc-tag (BEAT2) | Nucleic acid |
| 18 | BEAT2 | Amino acid |
| 19 | CD40/CD3 (BEAT3) | Nucleic acid |
| 20 | BEAT3 | Amino acid |
| 21 | MHCII/CD3 (BEAT4) | Nucleic acid |
| 22 | BEAT4 | Amino acid |
| 23 | BEAT1 vector | Nucleic acid |
| 24 | BEAT2 vector | Nucleic acid |
| 25 | BEAT3 vector | Nucleic acid |
| 26 | BEAT4 vector | Nucleic acid |

The present disclosure is predicated, at least in part, on the inventors' unexpected finding that the engagement of CAR T cells with antigen presenting cells (APCs) using bispecific polypeptides enhances T cell expansion in vitro and in vivo with a high degree of tumour inhibition without toxicity, while reducing the effective dose of CAR T cells required to achieve a therapeutic effect. Importantly, the CAR T cells receive activation and proliferation signals in lymphoid tissue, away from the immunosuppressive tumour microenvironment.

Therefore, in an aspect disclosed herein, there is provided a bispecific polypeptide comprising a first binding domain and a second binding domain, wherein the first binding domain is an antibody or antibody fragment that specifically binds to an antigen expressed on an antigen APC, and wherein the second binding domain is an antibody or antibody fragment that specifically binds to an antigen on a chimeric antigen receptor (CAR) expressed by an immune cell.

Bispecific Polypeptides

As used herein, the term "bispecific polypeptide" means a polypeptide that can specifically bind two different target antigens simultaneously. The bispecific polypeptides described herein comprise two structurally distinct binding domains (i.e., regions), each of which specifically binds to a single target antigen. Bispecific polypeptides can be used to bind to a target antigen on an APC and a different target antigen on an immune cell that expresses a CAR. Further, bispecific polypeptides can be used to bind to a target antigen on an APC and a different target antigen on a CAR expressed by an immune cell. Bispecific polypeptides can include polypeptide sequences (i.e., domains) of one of more antibodies or antibody fragments (e.g., one or more scFvs). In another embodiment, the bispecific polypeptides can include polypeptide sequences of one or more ligands.

In an embodiment, the bispecific polypeptide is a tandem single-chain variable fragment antibody (taFv) having a first scFv and a second scFv.

The bispecific polypeptides described herein may be variously referred to as "Bispecific Engagers of APCs and T cells" or "BEATs".

"Polypeptide", "peptide", "protein" and "proteinaceous molecule" are used interchangeably herein to refer to molecular comprising or consisting of a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers.

The term "amino acid" as used herein refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basis chemical structure as a naturally occurring amino acid, e.g., a carbon that is bound to a hydrogen, a carboxyl group, an amino group, and an R group. Such analogs may have modified R groups (e.g., norleucine) or modified peptide backbones. Amino acid mimetics refers to chemical compounds that have a structure that is different from the general chemical structure of an amino acid, but that functions similarly to a naturally occurring amino acid.

Amino acids may be referred to herein by their commonly used full name (e.g., cysteine), their commonly known three letter symbols (e.g., Cys), or by the one-letter symbols recommended by the IUPAC-IUB Biochemical Nomenclature Commission (e.g., C). Nucleotides, likewise, may be referred to by their commonly accepted single-letter codes.

The term "antigen" as used herein refers to a molecule bound by an "antibody", "antibody fragment" or a "bispecific polypeptide". Antigens may be proteins recognized by immunoglobulins, in which case the sites on the proteins bound by the immunoglobulins are referred to as "epitopes". In an embodiment, the antigen can be a ligand of a cell surface receptor (e.g., MHCII, Clec9a, PD-L1, PD-L2, galectin, CD11c, CD19, CD40 and CD83). In another embodiment, the antigen is a tag on a CAR expressed by an immune cell.

The term "antigen presenting cell" or "APC" as used herein may be a professional antigen presenting cell (e.g., a dendritic cell, macrophage, B-cell, epithelial cell, etc.) or a non-professional antigen presenting cell (e.g., a fibroblast, thymic epithelial cell, thyroid epithelial cell, glial cell, pancreatic beta cell, vascular endothelial cell, etc.). In a preferred embodiment, the APC is a professional antigen binding cell, and is not a tumour cell.

In an embodiment, the first binding domain specifically binds to an antigen expressed on an APC selected from the group consisting of MHCII, Clec9a, PD-L1, PD-L2, galectin, CD11c, CD19, CD40 and CD83. MHCII is expressed on dendritic cells (DCs), mononuclear phagocytes, some endothelial cells, thymic epithelial cells, and B cells; Clec9a is expressed on BDCA+ dendritic cells and a small subset of CD14+/CD16-monocytes; PD-L1 and PD-L2 are expressed on macrophages, myeloid DCs, B cells and vascular endothelial cells; galectin is expressed by T helper cells and B cells; CD11c is expressed at high levels by DCs; CD19 is expressed on all professional B cells to mature B cells and follicular DCs; CD40 is expressed by dendritic cells, B cells and macrophages; and CD83 is predominantly expressed by mature DCs. In a preferred embodiment, the antigen specifically bound by the first binding domain is not a tumour-associated antigen.

In an embodiment, the second binding domain specifically binds to an antigen on an immune cell expressing a CAR or similar receptor. In further embodiments, the second binding domain of the bispecific polypeptides of the invention, may bind to an antigen on the immune cell, wherein the antigen is not part of the CAR, but is an antigen present on the cell surface of the immune cell.

In certain embodiments, the immune cell is an engineered T-cell or NK cell, typically, wherein the antigen on the engineered T-cell or NK cell is part of a CAR. In accordance with these embodiments, the second binding domain of the bispecific polypeptide of the invention may bind to an extracellular portion of the CAR. The second binding domain may bind to the antigen-binding domain of the CAR, or it may bind to an extracellular region of the CAR that is not involved in antigen binding.

In certain embodiments, the CAR present on an immune cell can also comprise additional amino acids or molecules for binding with the second binding domain. As is known in the art, CAR constructs may be designed to include a "tag", which is typically a short amino acid sequence that is specifically recognized by an antibody. In some embodiments, the immune cell is a T-cell or a NK cell engineered to express a CAR which includes a tag. In the context of such embodiments, the second binding domain of the bispecific polypeptide may bind to the tag or it may bind to a region of the CAR other than the tag. In some embodiments in which the immune cell is a T-cell or a NK cell engineered to express a CAR which includes a tag, the second binding domain of the bispecific polypeptide binds to a region of the CAR other than the tag.

Illustrative examples of tags present on CARs include peptide tags (e.g., FLAG-tag, HA-tag, His-tag, Myc-tag, S-tag, SBP-tag, Strep-tag, eXact-tag) and protein tags (e.g., GST-tag, MBP-tag, GFP-tag, a tag in the form of a domain for binding to an antibody or other protein, a nuclear protein (such as a leucine zipper) or any other protein modification to a CAR). In an embodiment, the antigen or affinity tag on the CAR is a c-Myc-tag.

In some embodiments, the immune cell is a T-cell or a NK cell engineered to express a CAR which does not include a tag. In some embodiments, the immune cell is a T-cell or a NK cell engineered to express a CAR which does not include a tag or any heterologous tumour-associated antigens or fragments of tumour-associated antigens.

In certain embodiments, the immune cell is a T-cell or a NK cell engineered to express a CAR and the bispecific polypeptide binds to an extracellular part of the CAR. As is known in the art, a CAR is a cell-surface receptor comprising an extracellular domain, a transmembrane domain and a cytoplasmic domain in a combination that is not naturally found in a single protein. The extracellular domain comprises an antigen-binding domain, which may be an antibody or antibody fragment. The antibody or antibody fragment may be a human antibody or fragment, humanized antibody or fragment or a non-human antibody or fragment. Typically, the antigen-binding domain is an antibody fragment, such as a Fab or scFv. Most typically, the antigen-binding domain is an scFv. The extracellular domain also typically comprises a spacer (or hinge) region linking the antigen-binding domain to the transmembrane domain. The spacer region may be derived from an immunoglobulin, such as IgG1 or IgG4, or it may be derived from alternative cell-surface proteins, including, but not limited to, CD4, CD8, or CD28.

In certain embodiments, the bispecific polypeptide of the invention comprises a second binding domain derived from an anti-idiotype antibody or antigen-binding fragment thereof, wherein the anti-idiotype antibody is an anti-idiotype antibody of the antibody portion of a CAR. In other words, the second binding domain binds to the antigen binding domain of the CAR.

Anti-idiotype antibodies are known in the art and the skilled person will be well able to utilise to the antigen-binding domains of these antibodies in the design of a bispecific polypeptide of the invention. Accordingly, in some embodiments, the second binding domain of the bispecific polypeptide of the invention comprises an antibody or antibody fragment derived from an anti-idiotype antibody specific for an anti-CD 19, anti-Her2, or other antibody, or antigen-binding fragment of an anti-idiotype antibody for binding an antibody found in a CAR.

A number of anti-idiotype antibodies are known in the art. For example, International Patent Application Publication No. WO 2014/190273 and Jena et al. 2013, *PLoS One*, 8(3): e57838, describe an anti-idiotype antibody (mAb clone no. 136.20.1) that recognizes the anti-CD19^ scFv FMC63, which is used in a number of CAR constructs in current development.

In certain embodiments, the second binding domain of the bispecific polypeptide of the invention comprises an antibody or antigen-binding domain derived from an anti-idiotype antibody specific for an anti-CD19 antibody, or antigen-binding fragment of the anti-idiotype antibody, that may have one or more of the same CDRs (i.e. one or more of, or all of, VH CDR1, VH CDR2, CH CDR3, VL CDR1, VL CDR2, and VL CDR3, using the Kabat definition, the Chothia definition, or a combination of the Kabat and Chothia definitions) as mAb clone no. 136.20.1. In some embodiments, the multi-specific antigen-binding construct comprises an antigen-binding polypeptide construct derived from an anti-idiotype antibody specific for an anti-CD19 antibody, or antigen-binding fragment of the anti-idiotype antibody, that may have one or more (for example, two) variable regions from mAb clone no. 136.20.1. In some embodiments, the multi-specific antigen-binding construct comprises an antigen-binding polypeptide construct derived from an anti-idiotype antibody specific for an anti-CD19 antibody, or antigen-binding fragment of the anti-idiotype antibody, that binds to the same epitope as mAb clone no. 136.20.1.

Other examples of anti-idiotype antibodies include those that are commercially available from AbD Serotec®, an anti-idiotype antibody specific for an anti-CD22 antibody described in International Patent Publication No. WO 2013/188864, an anti-idiotype antibody specific for an anti-CEA antibody described in International Patent Publication No. WO 97/34636, an anti-idiotype antibody specific for an anti-GD2 antibody described in U.S. Pat. No. 5,935,821, and an anti-idiotype antibody specific for an anti-NY-ESO-1 antibody described in Jakka et al. 2013, *Anticancer Research*, 33(10): 4189-420. Custom anti-idiotype antibodies may also be obtained from AbD Serotec®.

Alternatively, anti-idiotype antibodies to CARs targeting CD19 or other tumour-associated antigens may be made according to the method described in Jena et al., supra, and used for the construction of an anti-idiotype antigen-binding polypeptide construct.

In some embodiments, the bispecific polypeptide comprises an second binding domain that binds to an extracellular region of a CAR that is not involved in antigen binding. The second binding domain of the bispecific polypeptides of the invention may bind to any antigen on an extracellular domain of a CAR present on an immune cell. For example, the second binding domain of the bispecific polypeptide may bind to the hinge region of the CAR (i.e., between the transmembrane domain and scFv portion of the CAR), or to the spacer region between the Variable Heavy and Variable Light chains of the scFv portion of the CAR, or any other region of the CAR.

In some embodiments, the hinge region may be an scFv-CD28 or scFv-CD8 junction, which comprises neo-epitopes that may be targeted by the second binding domain. In some embodiments, the hinge region may comprise mutated (Fc-binding null) IgG CH2/3 that may be targeted by the second binding domain. In some embodiments, the hinge region may comprise a spacer such as a Strep-tag II as described by Liu et al. (2016, *Nature Biotechnology*, 34:430-434) that may be targeted by the second binding domain.

An example of an anti-CAR antibody that binds to a hinge region of the CAR molecule is the 2D3 antibody described in International Patent Application Publication No. WO 2014/190273, which binds to an IgG4 CH2-CH3 hinge region. In some embodiments, the multi-specific antigen-binding construct comprises an antigen-binding polypeptide construct that binds to an IgG4 CH2-CH3 hinge region. In some embodiments, the multi-specific antigen-binding construct comprises an antigen-binding polypeptide construct that binds to an IgG4 CH2-CH3 hinge region and has one or more of the same CDRs (i.e., one or more of, or all of, VH CDR1, VH CDR2, CH CDR3, VL CDR1, VL CDR2 and VL CDR3) as 2D3, or has one or more (for example, two) variable regions of 2D3 as described in WO 2014/190273. In some embodiments, the second binding domain of the bispecific polypeptide binds to an IgG4 CH2-CH3 hinge region and binds to the same epitope as 2D3 as described in WO 2014/190273.

The terms "Chimeric Antigen Receptor" or "CAR" as used herein mean a recombinant polypeptide comprising an antigen binding domain that is linked to at least one intracellular signaling domain. The antigen binding domain of a CAR is a functional portion of the CAR that specifically binds to (i.e., specifically targets) an antigen expressed on a cancer cell (i.e., a "tumour-associated antigen"). Examples of tumour-associated antigens are known to persons skilled in the art, illustrative examples of which include Her2, CEA, FBP, CD19 and CD209.

As used herein "tumour-associated antigen" refers to an antigen that is expressed by cancer cells. A tumour-associated antigen may or may not be expressed by non-tumour cells. When a tumour-associated antigen is not expressed by non-tumour cells (i.e., when it is unique to tumour cells) it may also be referred to as a "tumour-specific antigen." When a tumour-associated antigen is not unique to a tumour cell, it is also expressed on a non-tumour cell under conditions that fail to induce a state of immunologic tolerance to the antigen. The expression of the antigen on the tumour may occur under conditions that enable the immune system to respond to the antigen. Tumour-associated antigens may be antigens that are expressed on non-tumour cells during fetal development when the immune system is immature and unable to respond, or they may be antigens that are normally present at low levels on normal cells but which are expressed at much higher levels on tumour cells. Those tumour-associated antigens of greatest clinical interest are differentially expressed compared to the corresponding non-tumour tissue and allow for a preferential recognition of tumour cells by specific T-cells or immunoglobulins.

Complete and sustained T cell activation and proliferation require a primary initiating signal (signal 1), a secondary co-stimulatory receptor engagement signal (signal 2) and a cytokine receptor engagement signal (signal 3). As CAR T cells do not operate in a MHC-restricted manner, their interaction with APCs is generally deficient, with signal 2 and signal 3 being severely compromised. Therefore, the incorporation of one or more signaling domains can impact on the levels and sustenance of the activation of T cells in response to tumour associated antigen, which can result in increased cytokine production.

In an embodiment, the CAR comprises at least one intracellular signaling domain. Suitable signaling domains will be familiar to persons skilled in the art, illustrative examples of which include CD3ζ, CD28, 41BB, DAP10, OX40, ICOS, DAP12, KIR2DS2, 4-1BB, CD3ε, CD35, CD3υ, CD25, CD27, CD79A, CD79B, CARD11, FcRa, Fcftp, FcRy, Fyn, HVEM, Lck, LAT, LRP, NKG2D, NOTCH1, NOTCH2, NOTCH3, NOTCH4, ROR2, Ryk, SLAMF1, Slip76, pTa, TCRa, TCRβ, TRIM, Zap70, PTCH2 and LIGHT. In an embodiment, the CAR comprises at least two intracellular signaling domains. In another embodiment, the intracellular signaling domains of a CAR comprise the CD28 and CD3ζ signaling domains.

In further embodiments, the second binding domain binds to an antigen on an immune cell that expresses a CAR, wherein the antigen is not the CAR or is not on the CAR. In other words, the immune cell that expresses the CAR may also comprise one or more antigens which can be bound by the second binding domain of the bispecific polypeptides of the invention. For example, the antigen may comprise a naturally-occurring protein present on the immune cell surface (such as CD3, CD4, CD8, CD25, CD127, CD196 (CCR6), CD27, CD28, CD45RA, CD45RO, CD62L, CD197, and HLA-DR). Alternatively, the antigen on the immune cell may be an artificially introduced antigen, such as an affinity tag. Examples of peptide tags which may be present on the surface of the immune cell include peptide tags (e.g., FLAG-tag, HA-tag, His-tag, Myc-tag, S-tag, SBP-tag, Strep-tag, eXact-tag) and protein tags (e.g., GST-tag, MBP-tag, GFP-tag).

The first and second binding domains of the bispecific polypeptide of the invention are preferably in the form of an antibody or an antibody fragment. The term "antibody" as used herein broadly refers to any immunoglobulin (Ig) molecule comprised of four polypeptide chains, two heavy (H) chains and two light (L) chains. Also disclosed herein are antigen-binding fragments, mutants, variants, and derivatives thereof, which retain the essential epitope binding features of the antibody molecule. Such mutants, variants, and derivatives will be known to persons skilled in the art, illustrative examples of which are described elsewhere herein.

An antibody heavy chain will typically comprise a heavy chain variable region (HCVR or VH) and a heavy chain constant region. The heavy chain constant region is typically comprised of three domains, CH1, CH2 and CH3. A light chain will typically comprise a light chain variable region (LCVR or VL) and a light chain constant region, CL. The VH and VL regions can be further subdivided into regions of hypervariability, also known as complementary determining regions (CDR), interspersed with framework regions (FR). Each VH and VL is typically comprised of three CDs and four FR, arranged from amino-terminus to carboxy-terminus in the following order: FR1, CDR1, FR2, CDR2, FR3, CDR3 and FR4. Immunoglobulin molecules can be of any type (e.g. IgG, IgE, IgM, IgD, IgA and IgY), class (e.g. IgG1, IgG2, IgG3, IgG4, IgA1 and IgA2) or subclass.

The term "antigen-binding fragment" or "antibody fragment", as used herein, means one or more fragments of an antibody that retain the ability to specifically bind to the target antigen. Illustrative examples of antigen-binding fragments include (i) a Fab fragment, a monovalent fragment consisting of the VL, VH, CL and CH1 domains; (ii) a F(ab')$_2$ fragment, a F(ab')$_2$ fragment, a bivalent fragment comprising two Fab fragments linked by a disulfide bridge at the hinge region; (iii) a Fd fragment consisting of the VH and CH1 domains; (iv) a single-chain variable fragment (scFv) consisting of the VL and VH domains of a single arm of an antibody, (v) a dAb fragment (Ward et al. 1989, *Nature*, 341: 544-6), which comprises a single variable domain; and (vi) an isolated CDR.

In an embodiment, the first binding domain comprises a scFv. In another embodiment, the second binding domain comprises a scFv.

Suitable immune cells will be familiar to persons skilled in the art, illustrative examples of which include T cells, tumour infiltrating lymphocytes (TIL) and natural killer (NK) cells. In an embodiment, the cell is a T cell, a natural killer (NK) cell or a tumour infiltrating lymphocyte (TIL).

In a preferred embodiment, the immune cell that expresses the CAR is a T cell. Illustrative examples of suitable T cells include helper T cells (HTL; CD4$^+$ T cell), a cytotoxic T cell (CTL; CD8$^+$ T cell), CD4$^+$CD8$^+$ T cell, CD4$^-$CD8$^-$ T cell, or any other subset of T cells. Other illustrative examples of suitable T cells include T cells expressing one or more of the following markers: CD3, CD4, CD8, CD27, CD28, CD45RA, CD45RO, CD62L, CD127, CD197, and HLA-DR.

Sources of cells for use in accordance with the present invention will be known to persons skilled in the art, illustrative examples of which include peripheral blood, peripheral blood mononuclear cells, bone marrow, lymph nodes tissue, cord blood, thymus tissue, tissue from the site of infection, ascites, pleural effusion, spleen tissue, and tumors. In an embodiment, the cells are derived from whole blood.

The term "sequence identity" or "sequence homology" as used herein refers to the subunit sequence identity between two polymeric molecules, e.g., between two nucleic acid molecules, such as two DNA molecules or two RNA molecules, or between two polypeptide molecules. When a subunit position in both of the two molecules is occupied by the same monomeric subunit, e.g., if a position in each two DNA molecules is occupied by adenine, then they are homologous or identical at that position. The homology between two sequences is a direct function of the number of matching or homologous positions, e.g., if half (e.g., five positions in a polymer ten subunits in length) of the positions in two sequences are homologous, the two sequences are 50% homologous; if 90% of the positions (i.e., 9 of 10), are matched or homologous, the two sequences are 90% homologous.

In an embodiment, the bispecific polypeptide comprises a first binding domain comprising an amino acid sequence selected from the group consisting of SEQ ID NO: 2, or 4, or an amino acid sequence having at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, or more preferably at least 99% sequence identity to an amino acid sequence selected from the group consisting of SEQ ID NO: 2 or 4.

In an embodiment, the bispecific polypeptide comprises a second binding domain comprising an amino acid sequence of SEQ ID NO: 6 or 8, or an amino acid sequence having at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, or more preferably at least 99% sequence identity to SEQ ID NO: 6 or 8.

In an embodiment, the bispecific polypeptide comprises an amino acid comprising an amino acid sequence selected from the group consisting of SEQ ID NO: 16, 18, 20, or 22, or an amino acid sequence having at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, or more preferably at least 99% sequence identity to an amino acid sequence selected from the group consisting of SEQ ID NO: 16, 18, 20, or 22.

In an embodiment, the bispecific polypeptide comprises a first binding domain comprising an amino acid of SEQ ID NO: 2, or an amino acid sequence having at least at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, or more preferably at least 99% sequence identity to SEQ ID NO: 2; and a second binding domain comprising an amino acid of SEQ ID NO: 6, or an amino acid sequence having at least at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, or more preferably at least 99% sequence identity to SEQ ID NO: 6.

In an embodiment, the bispecific polypeptide comprises a first binding domain comprising an amino acid of SEQ ID NO: 2, or an amino acid sequence having at least at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, or more preferably at least 99% sequence identity to SEQ ID NO: 2; and a second binding domain comprising an amino acid of SEQ ID NO: 8, or an amino acid sequence having at least at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, or more preferably at least 99% sequence identity to SEQ ID NO: 8.

In an embodiment, the bispecific polypeptide comprises a first binding domain comprising an amino acid of SEQ ID NO: 4, or an amino acid sequence having at least at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, or more preferably at least 99% sequence identity to SEQ ID NO: 4; and a second binding domain comprising an amino acid of SEQ ID NO: 6, or an amino acid sequence having at least at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, or more preferably at least 99% sequence identity to SEQ ID NO: 6.

In an embodiment, the bispecific polypeptide comprises a first binding domain comprising an amino acid of SEQ ID NO: 4, or an amino acid sequence having at least at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, or more preferably at least 99% sequence identity to SEQ ID NO: 4 and a second binding domain comprising an amino acid of SEQ ID NO: 8, or an amino acid sequence having at least at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, or more preferably at least 99% sequence identity to SEQ ID NO: 8.

The bispecific polypeptides of the invention can include a linker sequence that links the first binding domain and the second binding domain. The linkers may, for example, function to join two domains of an antigen-binding polypeptide construct (such as the VH and VL of an scFv or diabody), or they may function to join two antigen-binding polypeptide constructs together (such as two or more Fabs or sdAbs), or they may function to join an antigen-binding polypeptide construct to a scaffold. In some embodiments, the bi-specific polypeptide may comprise multiple linkers (i.e., two or more), for example, one or more scFvs linked to a scaffold may comprise a linker joining the VH and VL of the scFv and a linker joining the scFv to the scaffold. Appropriate linkers are known in the art and can be readily selected by the skilled artisan based on the intended use of the linker (see, for example, Müller & Kontermann, "Bispecific Antibodies" in Handbook of Therapeutic Antibodies, Wiley-VCH Verlag GmbH & Co. 2014).

Useful linkers include glycine-serine (GlySer) linkers, which are well-known in the art and comprise glycine and serine units combined in various orders. Examples include, but are not limited to, (GS), (GSGGS)$_n$, (GGGS)$_n$ and (GGGGS)$_n$, where n is an integer of at least one, typically an integer between 1 and about 10, for example, between 1 and about 8, between 1 and about 6, or between 1 and about 5.

Other useful linkers include sequences derived from immunoglobulin hinge sequences. The linker may comprise all or part of a hinge sequence from any one of the four IgG classes and may optionally include additional sequences. For example, the linker may include a portion of an immunoglobulin hinge sequence and a glycine-serine sequence. A nonlimiting example is a linker that includes approximately the first 15 residues of the IgG1 hinge followed by a GlySer linker sequence, such as those described above, that is about 10 amino acids in length.

The length of the linker will vary depending on its application. Appropriate linker lengths can be readily selected by the skilled person. For example, when the linker is to connect the VH and VL domains of an scFv, the linker is typically between about 5 and about 20 amino acids in length, for example, between about 10 and about 20 amino acid in length, or between about 15 and about 20 amino acids in length. When the linker is to connect the VH and VL domains of a diabody, the linker should be short enough to prevent association of these two domains within the same chain. For example, the linker may be between about 2 and about 12 amino acids in length, such as, between about 3 and about 10 amino acids in length, or about 5 amino acids in length.

In some embodiments, when the linker is to connect two Fab fragments, the linker may be selected such that it maintains the relative spatial conformation of the paratopes of a F(ab') fragment, and is capable of forming a covalent bond equivalent to the disulphide bond in the core hinge of IgG. In this context, suitable linkers include IgG hinge regions such as, for example those from IgG1, IgG2 or IgG4. Modified versions of these exemplary linkers can also be used. For example, modifications to improve the stability of the IgG4 hinge are known in the art (see for example, Labrijn et al. 2009, *Nature Biotechnology*, 27: 767-771).

The linker may comprise a sequence of amino acid residues joining the first and second binding domains. Alternatively, the first and second binding domains may be linked via chemical conjugation (for example, to form a bis-aryl conjugate between the domains). Examples of suitable methods for chemical conjugation of binding domains are known in the art. Such methods include the use of succinimidyl compound modification of primary amines present on lysine residues, as used in TriLink Technologies bioconjugation reagents. In an embodiment, if the first and/or second binding domains are scFvs, the bispecific polypeptide comprises a linker sequence between the VH and VL domains of the scFvs. Suitable linker sequences would be known to persons skilled in the art, illustrative examples of which include relatively flexible and hydrophilic amino acid residues. In an embodiment, the linker sequence is selected from the group consisting of SEQ ID NO: 10, 12 or 14 or an amino acid sequence having at least 70% identity thereto, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, or more preferably at least 99% sequence identity to SEQ ID NO: 10, 12 or 14.

An antibody or antibody fragment can contain additional amino acids or molecules for purification or identification. For example, the antibody can contain an epitope or affinity tag. Illustrative examples of such epitopes or affinity tags include, peptide tags (e.g., FLAG-tag, HA-tag, His-tag, Myc-tag, S-tag, SBP-tag, Strep-tag, eXact-tag) and protein tags (e.g., GST-tag, MBP-tag, GFP-tag). In an embodiment, the epitope or affinity tag is a His-tag.

Nucleic Acids and Vectors

In another aspect disclosed herein, there is provided a nucleic acid encoding the bispecific polypeptide described herein. In yet another aspect there is provided a cell comprising the vector described herein.

The terms "polynucleotide", "polynucleotide sequence", "nucleotide sequence", "nucleic acid" or "nucleic acid sequence" as used interchangeably herein to designate mRNA, RNA, cRNA, cDNA or DNA. The term typically refers to polymeric form of nucleotides of at least 10 bases in length, either ribonucleotides or deoxynucleotides or a modified form or either type of nucleotide. The term includes single and double stranded forms of RNA and DNA.

As used herein, the term "gene" includes a nucleic acid molecule capable of being used to produce mRNA optionally with the addition of elements to assist in this process. Genes may or may not be capable of being used to produce a functional protein. Genes can include both coding and non-coding regions (e.g., introns, regulatory elements, promoters, enhancers, termination sequences and 5' and 3' untranslated regions).

The term "transgene" is used herein to describe genetic material that has been or is about to be artificially introduced into a genome of a host organism and that is transmitted to the progeny of that host. In some embodiments, it confers a desired property to a T cell which it is introduced, or otherwise leads to a desired therapeutic outcome.

As used herein, the terms "encode," "encoding" and the like refer to the capacity of a nucleic acid to provide for another nucleic acid or a polypeptide. For example, a nucleic acid sequence is said to "encode" a polypeptide if it can be transcribed and/or translated to produce the polypeptide or if it can be processed into a form that can be transcribed and/or translated to produce the polypeptide. Such a nucleic acid sequence may include a coding sequence or both a coding sequence and a non-coding sequence. Thus, the terms "encode," "encoding" and the like include an RNA product resulting from transcription of a DNA molecule, a protein resulting from translation of an RNA molecule, a protein resulting from transcription of a DNA molecule to form an RNA product and the subsequent translation of the RNA product, or a protein resulting from transcription of a DNA molecule to provide an RNA product, processing of the RNA product to provide a processed RNA product (e.g., mRNA) and the subsequent translation of the processed RNA product.

In an embodiment, the nucleic acid sequence encoding the bispecific polypeptide has a polynucleotide sequence selected from the group consisting of SEQ ID NO: 15, 17, 19, 21, 31 or 33, or a nucleic acid sequence having at least 70%, preferably at least 71%, preferably at least 72%, preferably at least 73%, preferably at least 74%, preferably at least 75%, preferably at least 76%, preferably at least 77%, preferably at least 78%, preferably at least 79%, preferably at least 80%, preferably at least 81%, preferably at least 82%, preferably at least 83%, preferably at least 84%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, or more preferably at least 99% sequence identity to SEQ ID NO: 15, 17, 19, 21, 31 or 33.

In another aspect, there is provided a vector comprising the nucleic acid described herein operably linked to a regulatory sequence.

The terms "regulatory element" or "regulatory sequence" refer to nucleic acid sequences (e.g., DNA) necessary for expression of an operably linked coding sequence in a particular cell. The regulatory sequences that are suitable for eukaryotic cells include promoters, polyadenylation signals, transcriptional enhancers, translational enhancers, leader or trailing sequences that modulate mRNA stability, as well as targeting sequences that target a product encoded by a transcribed polynucleotide to an intracellular compartment within a cell or to the extracellular environment.

Typically, the regulatory sequences include, but are not limited to, a promoter sequence, a 5' non-coding region, a cis-regulatory region such as a functional binding site for transcriptional regulatory protein or translational regulatory protein, an upstream open reading frame, ribosomal-binding sequences, transcriptional start site, translational start site, and/or nucleotide sequence which encodes a leader sequence, termination codon, translational stop site and a 3' non-translated region. Constitutive or inducible promoters as known in the art are contemplated. The promoters may be either naturally occurring promoters, or hybrid promoters that combine elements of more than one promoter.

Promoter sequences contemplated may be native to mammalian cells or may be derived from an alternative source, where the region is functional in the chosen organism. The choice of promoter will differ depending on the intended host cell. For example, promoters which could be used for expression in mammalian cells include the metallothionein promoter, which can be induced in response to heavy metals such as cadmium, the β-actin promoter as well as viral promoters such as the SV40 large T antigen promoter, human cytomegalovirus (CMV) immediate early (IE) promoter, Rous sarcoma virus LTR promoter, the mouse mammary tumour virus LTR promoter, the adenovirus major late promoter (Ad MLP), the herpes simplex virus promoter, and a HPV promoter, particularly the HPV upstream regulatory region (URR), among others. All these promoters are well described in the art and readily available.

Enhancer elements may also be used herein to increase expression levels of the nucleic acid sequence within the vector construct. Examples include the SV40 early gene enhancer, as described for example in Dijkema et al. (1985, *EMBO Journal*, 4:761), the enhancer/promoter derived from the long terminal repeat (LTR) of the Rous Sarcoma Virus, as described for example in Gorman et al., (1982, *Proceedings of the National Academy of Science. USA,* 79:6777) and elements derived from human CMV, as described for example in Boshart et al. (1985, *Cell,* 41:521), such as elements included in the CMV intron A sequence.

The vector construct may also comprise a 3' non-translated sequence. A 3' non-translated sequence refers to that portion of a gene comprising a DNA segment that contains a polyadenylation signal and any other regulatory signals capable of effecting mRNA processing or gene expression. The polyadenylation signal is characterised by effecting the addition of polyadenylic acid tracts to the 3' end of the mRNA precursor. Polyadenylation signals are commonly recognized by the presence of homology to the canonical form 5' AATAAA-3' although variations are not uncommon. The 3' non-translated regulatory DNA sequence preferably includes from about 50 to 1,000 nts and may contain transcriptional and translational termination sequences in addition to a polyadenylation signal and any other regulatory signals capable of effecting mRNA processing or gene expression.

The term "operably connected" or "operably linked" as used herein refers to a juxtaposition wherein the components so described are in a relationship permitting them to function in their intended manner. For example, a regulatory sequence "operably linked" to a coding sequence refers to the positioning and/or orientation of the regulatory sequence relative to the coding sequence to permit expression of the coding sequence under conditions compatible with the regulatory sequence.

As used here the terms "open reading frame" and "ORF" are used interchangeably herein to refer to the amino acid sequence encoded between translation initiation and termination codons of a coding sequence. The terms "initiation codon" (e.g., ATG) and "termination codon" (e.g., TGA, TAA, TAG) refer to a unit of three adjacent nucleotides ('codon') in a coding sequence that specifies initiation and chain termination, respectively, of protein synthesis (mRNA translation).

As used herein the term "recombinant" as applied to "nucleic acid molecules", "polynucleotides" and the like is understood to mean artificial nucleic acid structures (i.e., non-replicating cDNA or RNA; or replicons, self-replicating cDNA or RNA) which can be transcribed and/or translated in the cells as described herein.

Recombinant nucleic acid molecules or polynucleotides may be inserted into a vector. Non-viral vectors such as plasmid expression vectors or viral vectors may be used. The kinds of vectors and the technique of insertion of the nucleic acid construct according to this invention are known in the art, illustrative examples of which include cosmids, plasmids (e.g., naked or contained in liposomes) and viruses (e.g., lentiviruses, retroviruses, adenoviruses, and adeno-associated viruses).

In an embodiment, the vector comprises a polynucleotide sequence selected from the group consisting of SEQ ID NO: 23-26.

The nucleic acid sequence, polynucleotide or vector construct as described herein comprises a heterologous sequence that does not occur in nature.

In yet another aspect, there is provided a host cell comprising the vector described herein. Suitable host cells would be known to persons skilled in the art, illustrative examples of which include bacterial cells (e.g., *E. coli, P. mirabilis*), fungal cells (e.g., *S. cerevisiae, P. pastoria, T. reesei*), plant cells, insect cells (e.g., SF-9, SF21, Hi-5), or mammalian cells. In an embodiment, the host cell is a mammalian cell. Suitable mammalian cells would be known to persons skilled in the art, illustrative examples of which include a CHO or 293T cells. These cells are widely available from commercial suppliers.

Methods for Producing Bispecific Polypeptides

In another aspect, there is provided a method for producing the bispecific polypeptide described herein, comprising (i) culturing a cell as described herein in a culture medium and under conditions suitable for the expression of the bispecific polypeptide; and (ii) isolating the bispecific polypeptide from the cell or from the culture medium.

The bispecific polypeptides described herein can be produced using any number of expression systems would be known to persons skilled in the art, illustrative examples of which include production in or by bacteria (e.g., *E. coli, P. mirabilis*), fungi (e.g., *S. cerevisiae, P. pastoria, T. reesei*), plants or plant cells, insects or insect cells (e.g., SF-9, SF21, Hi-5), or mammalian cells. In an embodiment, the expression system is a mammalian expression system. Suitable mammalian expression systems would be known to persons skilled in the art, illustrative examples of which include a CHO or 293 expression system. These expression systems are widely available from commercial suppliers. In an embodiment, the bispecific polypeptides are produced using a mammalian expression system.

In another aspect, there is provided a method for producing the bispecific polypeptide described herein, comprising combining the first binding domain and the second binding domain under conditions suitable for the formation of a chemically conjugated bispecific polypeptide comprising the first binding domain and the second binding domain.

In a preferred embodiment, the chemically conjugated bispecific polypeptide is formed following succinimidyl compound modification of primary amines present on lysine residues, as described elsewhere herein.

It will be within the purview of the skilled person to utilise commercially available antibodies, or antigen-binding domains thereof, in order to generate the bispecific polypeptides as described herein. Further, it is within the purview of the skilled person to to reproduce antibodies or antigen binding domains thereof based on published sequence information pertaining to antibodies or antigen binding domains having the desired specificity, and to thereby include such antibodies or antigen binding domains thereof in a bispecific polypeptide according to the present invention. In particular, it will be understood that the present invention encompasses the generation of any bispecific antibody which is designed to have the specific binding affinities of the first and second binding domains as described herein (i.e., a first binding domain for binding to an antigen on an antigen presenting cell, preferably a professional antigen presenting cell such as a dendritic cell; and a second binding domain for binding to an antigen on an immune cell expressing a CAR, including wherein the antigen is an antigen on the CAR). The skilled person will appreciate that any combination of antigen binding domains with the desired binding specificity can be utilized to obtain a bispecific polypeptide of the invention.

Pharmaceutical Compositions

In another aspect, there is provided a pharmaceutical composition comprising the bispecific polypeptide described herein and a pharmaceutically acceptable carrier.

The composition described herein may be prepared in a manner known in the art and are those suitable for parenteral administration to mammals, particularly humans, comprising a therapeutically effective amount of the composition with one or more pharmaceutically acceptable carriers or diluents.

The term "pharmaceutically acceptable carrier" as used herein means any suitable carriers, diluents or excipients. These include all aqueous and non-aqueous isotonic sterile injection solutions which may contain anti-oxidants, buffers and solutes, which render the composition isotonic with the blood of the intended recipient; aqueous and non-aqueous sterile suspensions, which may include suspending agents and thickening agents, dispersion media, antifungal and antibacterial agents, isotonic and absorption agents and the like. It will be understood that compositions of the invention may also include other supplementary physiologically active agents.

The carrier is typically pharmaceutically "acceptable" in the sense of being compatible with the other ingredients in the composition and not injurious to the subject. Compositions include those suitable for parenteral administration, including subcutaneous, intramuscular, intravenous and intradermal administration. The compositions may conveniently be presented in unit dosage form and may be prepared by any method well known in the art of pharmacy. Such methods include preparing the carrier for association with the isolated T cells. In general, the compositions are prepared by uniformly and intimately bringing into association any active ingredients with liquid carriers.

In an embodiment, the composition is suitable for parenteral administration. In another embodiment, the composition is suitable for intravenous administration.

Compositions suitable for parenteral administration include aqueous and non-aqueous isotonic sterile injection solutions which may contain anti-oxidants, buffers, bactericides and solutes, which render the composition isotonic with the blood of the intended recipient; and aqueous and non-aqueous sterile suspensions which may include suspending agents and thickening agents.

The present disclosure also contemplates the combination of the composition described herein with other active agents and/or in addition to other treatment regimens or modalities such as radiation therapy or surgery. When the composition described herein is used in combination with known active agents, the combination may be administered either in sequence (either continuously or broken up by periods of no treatment) or concurrently or as an admixture. Suitable anti-cancer agents will be known to persons skilled in the art. Treatment in combination is also contemplated to encompass the treatment with either the composition of the invention followed by a known treatment, or treatment with a known agent followed by treatment with the composition of the invention, for example, as maintenance therapy. For example, in the treatment of cancer it is contemplated that the composition of the present invention may be administered in combination with an alkylating agent (such as mechlorethamine, cyclophosphamide, chlorambucil, ifosfamidecysplatin, or platinum-containing alkylating agents such as cisplatin, carboplatin and oxaliplain), and antimetabolite (such as a purine or pyrimidine analogue or an anti-folate agent, such as azathioprine and mercaptopurine), an anthracycline (such as daunorubicin, doxorubicin, epirubicin idarubicin, valrubicin, mitoxantrone or anthracycline analog), a plant alkaloid (such as a vinca alkaloid or a taxane, such as vincristine, vinblastine, vinorelbine, vindesine, paclitaxel or doestaxel), a topoisomerase inhibitor (such as a type I or type II topoisomerase inhibitor), a podophyllotoxin (such as etoposide or teniposide), a tyrosine kinase inhibitor (such as imatinib mesylate, nilotinib or dasatinib), an adenosine receptor inhibitor (such as A2aR inhibitors, SCH58261, CPI-444, SYN115, ZM241385, FSPTP or $A2_BR$ inhibitors such as PSB-1115), adenosine receptor agonists (such as CCPA, IB-MECA and CI-IB-MECA), a checkpoint inhibitor, including those of the PDL-1:PD-1 axis, nivolumab, pembrolizumab, atezolizumab, BMS-936559, MEDI4736, MPDL33280A or MSB0010718C), an inhibitor of the CTLA-4 pathway (such as ipilimumab and tremelimumab), an inhibitor of the TIM-3 pathway or an agonist monoclonal antibody that is known to promote T cell function (including anti-OX40, such as MEDI6469; and anti-4-BB, such as PF-05082566).

In a further aspect, the invention provides a kit or article of manufacture including one or more bispecific polypeptides of the invention, a nucleic acid encoding said bispecific polypeptide and/or pharmaceutical compositions as described above.

In further aspects there is provided a kit for use in a therapeutic application mentioned above, the kit comprising:

(a) a container holding a bispecific polypeptide, nucleic acid, vector or pharmaceutical composition of the invention; and
(b) a label or package insert with instructions for use.

The kit may also comprise one or more active principles or ingredients for treatment of cancer For example, the kit may also comprise an immune cell expressing a CAR.

The "kit" or "article of manufacture" may comprise a container and a label or package insert on or associated with the container. Suitable containers include, for example, bottles, vials, syringes, blister pack, etc. The containers may be formed from a variety of materials such as glass or plastic. The container holds a therapeutic composition which is effective for treating the condition and may have a sterile access port (e.g., the container may be an intravenous solution bag or a vial having a stopper pierceable by a hypodermic injection needle). The label or package insert indicates that the therapeutic composition is used for treating the condition of choice. In an embodiment, the label or package insert includes instructions for use and indicates that the therapeutic or prophylactic composition can be used to treat a cancer or other condition described herein.

The kit may comprise (a) a therapeutic or prophylactic composition; and (b) a second container with a second active principle or ingredient contained therein. The kit according to this embodiment of the invention may further comprise a package insert indicating the composition and other active principle can be used to treat cancer or condition described herein. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further comprise other materials desirable from a commercial and user standpoint, which would be known to persons skilled in the art, suitable examples of which include other buffers, diluents, filters, needles, and syringes.

Methods of Treatment

In another aspect, there is provided a method for the treatment of cancer comprising co-administering to a subject in need thereof a therapeutically effective amount of: (i) an immune cell expressing a CAR; and (ii) a bispecific polypeptide or pharmaceutical composition as described herein, wherein the bispecific polypeptide simultaneously binds to an antigen expressed on an endogenous APC of the subject and an antigen on the CAR expressed by the immune cell in vivo to stimulate the activation and expansion of the immune cell for the treatment of cancer.

Co-administration of an immune cell expressing a CAR and a bispecific polypeptide or pharmaceutical composition as described herein may be achieve by formulating the immune cell and the bispecific polypeptide or pharmaceutical composition in the same composition (e.g., for simultaneous co-administration) or they may be formulated as different compositions for sequential administration. By "sequential" administration is meant there is an interval between the administration of the immune cell and the bispecific polypeptide or pharmaceutical composition. The interval between sequential administrations may be seconds, minutes, hours or days. In an embodiment, periodic re-administration of the immune cell and the bispecific polypeptide or pharmaceutical composition may be required to achieve a desired therapeutic effect. Sequential administration may be in any order.

The inventors have surprisingly shown that the bispecific polypeptide described herein stimulates the activation and expansion of immune cell in vivo, thereby improving the efficacy of immune cell therapies, such as CAR T cell therapies. Accordingly, the bispecific polypeptide may be referred to as an "adjuvant". The term "adjuvant" as used herein refers to a bispecific polypeptide that can increase the magnitude of the immune response elicited by the immune cell expressing a CAR beyond that which would be expected from the immune cell expressing a CAR alone.

Immune cell activation can be accomplished by providing a primary stimulation signal through, for example, the T cell TCR/CD3 complex or via stimulation of the CD2 surface protein and by providing a secondary co-stimulation signal through an accessory molecule, e.g, CD28 or 4-1BBL. In addition to the primary stimulation signal provided through the TCR/CD3 complex, or via CD2, induction of T cell responses requires a second, costimulatory signal. In particular embodiments, a CD28 binding agent can be used to provide a costimulatory signal. Suitable costimulatory ligands include, but are not limited to, CD7, B7-1 (CD80), B7-2 (CD86), 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, ILT3, ILT4, an agonist or antibody that binds Toll ligand receptor, and a ligand that specifically binds with B7-H3.

The terms "expanded", "expansion", "expanding", "propagation" and the like are used interchangeably herein to refer to the increase in the number of immune cells, either prior to administration of the cells to the subject or preparation of a pharmaceutical composition or after administration. Immune cells may be expanded using any cell culture method known in the art. For example, immune cells may be expanded in in vitro tissue culture systems, including liquid culture, monolayers and the like.

The therapeutic regimen for the treatment of cancer can be determined by a person skilled in the art and will typically depend on factors including, but not limited to, the type, size, stage and receptor status of the tumour in addition to the age, weight and general health of the subject. Another determinative factor may be the risk of developing recurrent disease. For instance, for a subject identified as being at high risk or higher risk or developing recurrent disease, a more aggressive therapeutic regimen may be prescribed as compared to a subject who is deemed at a low or lower risk of developing recurrent disease. Similarly, for a subject identified as having a more advanced stage of cancer, for example, stage III or IV disease, a more aggressive therapeutic regimen may be prescribed as compared to a subject that has a less advanced stage of cancer.

The term "cancer" as used herein means any condition associated with aberrant cell proliferation. Such conditions will be known to persons skilled in the art. In an embodiment, the cancer is a solid cancer. In another embodiment, the cancer is a Her2 positive cancer. In another embodiment, the cancer is selected from the group consisting of breast cancer, pancreatic cancer, and lung cancer.

The terms "treat", "treatment" and "treating" as used herein refers to any and all uses which remedy a condition or symptom, or otherwise prevent, hinder, retard, abrogate or reverse the onset or progression of cancer or other undesirable symptoms in any way whatsoever. Thus, the term "treating" and the like are to be considered in their broadest possible context. For example, treatment does not necessarily imply that a subject is treated until total recovery or cure. In conditions that display or are characterized by multiple symptoms, the treatment need not necessarily remedy, prevent, hinder, retard, abrogate or reverse all of said symptoms, but may remedy, prevent, hinder, retard, abrogate or reverse one or more of said symptoms.

The subject in which cancer is to be treated may be a human or a mammal of economic importance and/or social importance to humans, for instance, carnivores other than humans (e.g., cats and dogs), swine (e.g., pigs, hogs, and wild boars), ruminants (e.g., cattle, oxen, sheep, giraffes, deer, goats, bison, and camels), horses, and birds including those kinds of birds that are endangered, kept in zoos, and fowl, and more particularly domesticated fowl, e.g., poultry, such as turkeys, chickens, ducks, geese, guinea fowl, and the like, as they are of economic importance to humans. The term "subject" does not denote a particular age. Thus, adult, juvenile and newborn subjects are intended to be covered.

The terms "subject", "individual" and "patient" are used interchangeably herein to refer to any subject to which the present disclosure may be applicable. In an embodiment, the subject is a mammal. In another embodiment, the subject is a human.

The term "therapeutically effective amount" as used herein means the amount of cells when administered to a mammal, in particular a human, in need of such treatment, is sufficient to treat cancer. The precise amount of modified cells to be administered can be determined by a physician with consideration of individual differences in age, weight, tumor size, extent of infection or metastasis, and condition of the subject.

Typically, administration of immune cell (e.g., CAR-T cell) therapies is defined by number of cells per kilogram of body weight. However, because the modified cells will replicate and expand after transfer, the administered cell dose will not resemble the final steady-state number of cells. In an embodiment, a pharmaceutical composition comprising the modified cells of the present invention may be administered at a dosage of $10^4$ to $10^9$ cells/kg body weight. In another embodiment, a pharmaceutical composition comprising the modified cells of the present invention may be administered at a dosage of $10^5$ to $10^6$ cells/kg body weight, including all integer values within those ranges.

Compositions comprising the bispecific polypeptides as described herein can also be administered multiple times at these dosages. The optimal dosage and treatment regimen for a particular subject can be readily determined by one skilled in the art by monitoring the patient for signs of disease and adjusting the treatment accordingly.

In an embodiment, the immune cell is derived from an autologous cell. In another embodiment, the immune cell is derived from an allogeneic cell.

The term "autologous" refers to any material derived from the same individual to whom the material is later to be re-introduced to the individual.

The term "allogeneic" refers to any material derived from a different individual of the same species as the individual to whom the material is introduced. Two or more individuals are said to be allogeneic to one another when the genes at one or more loci are not identical. In some aspects, allogeneic materials from individuals of the same species may be sufficiently genetically distinct to interact antigenically.

Cell Manufacturing

In order to achieve sufficient therapeutic doses of immune cell compositions, methods for manufacturing of immune cells typically involved one or more rounds of stimulation, activation and/or expansion. In accordance with the methods disclosed herein, immune cells may be stimulated to activate and expand both in vivo and in vitro.

Accordingly, in another aspect disclosed herein, there is provided a method for stimulating the activation and expansion of an immune cell in vivo comprising co-administering to a subject an effective amount of: (i) an immune cell expressing a CAR; and (ii) a bispecific polypeptide, or the pharmaceutical composition as described herein, wherein the bispecific polypeptide simultaneously binds to an antigen expressed on an endogenous APC of the subject and an antigen on the CAR expressed by the immune cell in vivo.

The in vivo activation and expansion of immune cells as described herein facilitates a reduction in the number of immune cells required for each therapeutic dose of the immune cell.

In another aspect, there is provided a method for stimulating the activation and expansion of an immune cell in vitro comprising culturing an isolated immune cell expressing a CAR in a culture medium comprising: (i) an APC or APC mimetic; and (ii) a bispecific polypeptide as described herein, wherein the bispecific polypeptide simultaneously binds to an antigen expressed on the APC or APC mimetic and an antigen on the CAR expressed by the immune cell.

The immune cell manufacturing methods contemplated herein simple and robust culture initiation and activation steps that contribute to a resulting immune cell composition that is a superior therapeutic product. In one embodiment, culture initiation and activation comprises seeding cell populations in a cell culture vessel, e.g., cell culture bag, GREX bioreactor, WAVE bioreactor, etc. and activating immune cells through primary and co-stimulatory immune cell signaling pathways. The cellular compositions may further be cultured in the presence of one or more additional growth factors or cytokines, e.g., IL-2, IL7, and/or IL-15, or any suitable combination thereof.

In another embodiment, activation and expansion of immune cells comprises culturing isolated immune cells with an APC or APC mimetic. In an embodiment, the APC or APC mimetic is selected from the group consisting of a donor-derived APC, a synthetic artificial APC (aAPC), microbeads (Dynabeads) functionalized with activating antibodies for CD3 and CD8, autologous monocyte-derived dentritic cells (mo-DCs) and scaffolds that mimic APCs.

In particular embodiments, culture initiation comprises seeding a population of cells comprising T cells, e.g., PBMCs, in a cell culture vessel, at a desired density, e.g., $1-5\times10^6$ cells/mL in a suitable cell culture medium containing one or more cytokines, primary stimulatory ligands, and co-stimulatory ligands. In another embodiment, the cytokines, stimulatory, and co-stimulatory ligands may be subsequently added to the PBMCs in the cell culture medium.

In one embodiment, the cell culture vessel is a cell culture bag, including but not limited MACS® GMP Cell Expansion Bags, MACS® GMP Cell Differentiation Bags, EXP-Pak™ Cell Expansion Bio-Containers, VueLife™ bags, KryoSure™ bags, KryoVue™ bags, Lifecell® bags, PermaLife™ bags, X-Fold™ bags, Si-Culture™ bags, and VectraCell™ bags, as contemplated elsewhere herein.

In particular embodiments, the cells are seeded in a cell culture vessel comprising a suitable cell culture medium. Illustrative examples of suitable cell culture media include, but are not limited to TCGM; X-VIVO™15 supplemented with 2 mM GlutaMAX™-I, 10 mM HEPES, and 5% human AB serum), CTS™ OpTmizer~ T Cell Expansion SFM (Life Technologies), CTS™ AIM V® Medium (Life Technologies), RPMI 1640, Clicks, DMEM, MEM, a-MEM, F-12, X-Vivo 15 (Lonza), CellGro® Serum-Free Medium (CellGenix), and X-Vivo 20 (Lonza) with added amino acids, sodium pyruvate, and vitamins, either serum-free or supplemented with an appropriate amount of serum (or plasma) or a defined set of hormones, and/or an amount of cytokine(s) sufficient for the growth and expansion of immune cells.

Cell culture media contemplated herein may further comprise one or more factors including, but not limited to serum (e.g., fetal bovine or human serum), interleukin-2 (IL-2), insulin, IFN-γ, IL-4, IL-7, IL-21, GM-CSF, IL-10, IL-12, IL-15, TGFβ, and TNF-α.

In an embodiment, the APC or APC mimetic is selected from the group consisting of a donor-derived APC, a synthetic artificial APC (aAPC), microbeads (Dynabeads) functionalized with activating antibodies for CD3 and CD8, autologous monocyte-derived dentritic cells (mo-DCs) and scaffolds that mimic APCs.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Unless otherwise defined, all technical and scientific terms used herein have the same meanings as commonly understood by one of ordinary skill in the art to which this invention belongs.

The various embodiments enabled herein are further described by the following non-limiting examples.

EXAMPLES

A. Materials
Cell Culture

E0771 is a mouse breast cancer cell line (Johnstone et al., 2015, *Disease Models & Mechanisms*, 8:237-51), 24JK is a methylcholanthrene-induced fibrosarcoma (Shiloni et al., 1993, *Cancer Immunology and Immunotherapy*, 37:286-92), and MC38 is a chemically-induced colon adenocarcinoma (Corbett et al., 1975, *Cancer Research*, 35:2434-9). These cell lines originated from C57BL/6 mice, and the parental cell lines were retrovirally transduced to express the human-Her2 antigen under the control of the mouse stem cell virus LTR promoter. These Her2+ cell lines are referred to as 24JK-Her2, MC38-Her2, and E0771-Her2. The MDA-MB-231, PANC1 and A549 cell lines are Her2+.

All cell lines were maintained at 37° C. 5% CO2 in RPMI media with supplements including 10% heat-inactivated fetal bovine serum (FBS), 1 mmol/L sodium pyruvate, 2 mmol/L glutamine, 0.1 mmol/L non-essential amino acids, 10 mM 4-(2-hydroxyethyl)-1-piperazineethanesulfonic acid (HEPES), 100 U/mL penicillin and 100 μg/mL streptomycin. E0771-Her2 was cultured in supplemented DMEM, which enhanced adherence to flasks.

CAR T Cells

PBMC were collected from the buffy coats of whole blood taken from human or mouse donors. Transduction of human T cells using a Her2-specific CAR retroviral vector or control empty vector was performed in accordance with the methods described in Ritchie et al. (2013, *Molecular Therapy*, 21(11):2122-29). Transduction of mouse T cells using a Her2-specific CAR retroviral vector or control empty vector was performed in accordance with the methods described in Mardiana et al. (2017, *Cancer Research*).

Other Immune Cells

APCs were generated using irradiated PBMCs, FACS sorted CD19+ B cells from PBMCs, or monocyte-derived dendritic cells (Mo-DC). A commercially available kit (Miltenyi Biotec) was used to generate mo-DC in a mixture of immature and mature mo-DC.

B. BEAT Design

BEATs were designed by joining two antibody scFv domains into a single polypeptide chain with a flexible linker. The first scFv domain was designed to specifically bind to CD40 (SEQ ID NO: 2) or MHCII (SEQ ID NO: 4). cDNA was isolated from hybridoma cell lines producing monoclonal antibodies against CD40 (FGK45) and MHCII (M5/114). Genes encoding variable H and L domains of these monoclonal antibodies were cloned and genetically fused by a (G4S)3-linker sequence to produce APC-specific scFvs. The second scFv domain was designed to specifically bind CD3 (SEQ ID NO: 6) or the c-myc-tag (SEQ ID NO: 8) of the Her2-specific CAR described above and a CAR-specific scFv was generated using the same method.

The APC-specific scFvs and the CAR-specific scFv were recombinantly linked to produce the genes encoding the BEATs (SEQ ID NO: 17 and 19).

C. BEAT Production

BEAT coding sequences were cloned into a pCDNA3.4 TOPO vector containing a cytomegalovirus (CMV) promoter for high-level expression of native protein in mammalian cell cultures. The coding sequences of the inserts were verified according to standard protocols. Expi293 Expression System (Invitrogen), jetPEI (Polyplus-transfection S.A.), and lipofectamine was used to transfect mammalian cells for rapid and ultra-high yield protein production of BEATs.

For the bacterial production of BEATs, a Gateway cloning system (Invitrogen) was used. Accordingly, BEAT coding sequences were inserted into an entry plasmid to create pDONR221ZeoBEAT. Competent *E. coli* were then transformed and positive clones containing the pDONR221ZeoBEAT were selected and sequenced. Thereafter, the pDONR221ZeoBEAT was combined with the pDestination vector pET15bGW to create pET15bBEAT. Competent *E. coli* were then transformed and positive clones containing the pET15bBEAT were selected and sequenced. The pET15bBEAT was then transformed into BL21DE3 *E. coli* and induced with IPTG to produce the BEAT polypeptides.

BEAT polypeptides containing the His-tag were collected using His60 Ni Superflow resin/Nickel beads. The purity and concentration of the BEATs were tested using a 6His check kit (Cisbio) electrophoresis and western blot.

To confirm the binding of the recombinant BEAT polypeptides, the BEATs will be conjugated with fluorescent dyes. The binding of the labelled BEATs will be confirmed using flow cytometry. In addition, we will confirm that the BEATs and the original monoclonal antibodies bind to the same molecules using a competitive binding assay.

Chemically conjugated BEAT polypeptides were prepared using the Protein-Protein Conjugation kit (TriLink Bio Technologies). In brief, antibodies specific for myc-tag (present in the CAR), CD40, PD-L2 or Clec9a were desalted and concentrated to the modification buffer using zebra columns.

When preparing the BEAT polypeptides, one antibody was modified by S-HyNic, and the other by S-4FB, both at a Molar Substitution Ratio 5. After incubating the antibodies with S-HyNic or S-4FB at room temperature for 2.5 hours, the modified antibodies were desalted and transferred to conjugation buffer using zebra columns. Subsequently, equivalent molar amounts of S-HyNic and S-4FB modified antibodies were mixed together, and 10× TurboLink Catalyst Buffer was added to the mixture at 1/10 volume. The protein mixture was then incubated overnight at 4° C. On the second day of the conjugation protocol, the sample was centrifuged at 5000 g for 5 minutes to remove any aggregates.

Conjugation of the antibodies was confirmed by electrophoresis (NuPAGE gel, Invitrogen). Thereafter, the conjugated product was purified using a HiLoad 16/600 Superdex™ 200 pg column (GE Healthcare Life Sciences) on fast protein liquid chromatography (FPLC) to PBS −/−. After purification using FPLC, the molecular weights of the different fractions of the chemically conjugated BEATs were confirmed by electrophoresis (NuPAGE gel, Invitrogen). In some instances, the purified chemically conjugated BEATs were further concentrated using Vivaspins (Sartorius Stedim).

E. SEB Functional Analysis

Human or mouse T cells were co-cultured with APCs and SEB and assessed for cell proliferation, IFN-γ secretion and TCRVβ8$^+$ T cell infiltration to the spleen at 24-72 hours post-co-culture.

To determine whether SEB could enhance CAR T cell treatment efficacy by enhancing T cell expansion, we tested three different murine cancer models, E0771-Her2 breast cancer, 24JK-Her2 sarcoma and MC38-Her2 carcinoma implanted in the Her2 transgenic mice. These immunocompetent Her2 transgenic mice express human Her2 in normal breast and cerebrum under the control of the whey acidic protein (WAP) promoter, so they are tolerant to Her2+ cell lines (Piechocki et al., 2003, *Journal of Immunology*, 171: 5787-94). When Her2+ tumours were established, CAR T cells were adoptively transferred and two doses of SEB were administered i.p. on the same day and 5 days later.

F. BEAT Functional Analysis

A chemically conjugated bispecific polypeptide was generated from anti-CD40/anti-myc antibodies to assess the effect of the BEAT on cell proliferation. A c-myc-tag already present on the Her2-specific CAR described above, served as the CAR-specific antigen.

T cells, BEATs and APCs will be co-cultured and a number of assays will be used to confirm the functional changes on T cells and APCs. Cell proliferation (tritiated thymidine incorporation, CFSE labelling and cell counts), cytokine secretion (ELISA, cytokine bead-array assay and intracellular staining) and cell activation/differentiation status (markers including CD25, CD69, CD45RA, CD45RO, CD27, CD28, MHCII, CD80, CD86 and CCR7) will be measured 24-72 hours post co-culture.

The cytotoxic capacity of T cells stimulated by BEATs will be assessed using a range of assays, including a chromium release assay for testing cell lysis, granzyme B and CD107a staining on T cells, Annexin V/7AAD and a real-time apoptosis/necrosis analysis (RealTime-Glo Annexin V apoptosis and necrosis assay kit, Promega). Appropriate BEAT, T cell and tumour cell controls will be used to determine the specificity.

To determine the ability of BEAT-generated CAR T cells to respond against a variety of solid tumour cell lines, we will use Her2-positive human cell lines MDA-MB-231 breast, PANC1 pancreatic and A549 lung cancer cell lines (or controls) as targets following implantation in immuno-deficient mice, or E0771-Her2, MC38-Her2, 24JK-Her2 mouse tumor cell lines in Her2-transgenic mice. When Her2+ tumours are established, CAR T cells will be adoptively transferred and two doses of BEATs administered i.p. on the same day and 5 days later.

Results

BEAT Production Using a Mammalian System

Mammalian systems can be used to produce BEATs in a soluble form and has the advantage of appropriate post-translational modifications, however, the yield is relatively low (i.e., every $10^8$ cells produced less than 1 nmol scFv protein).

Figure 2:
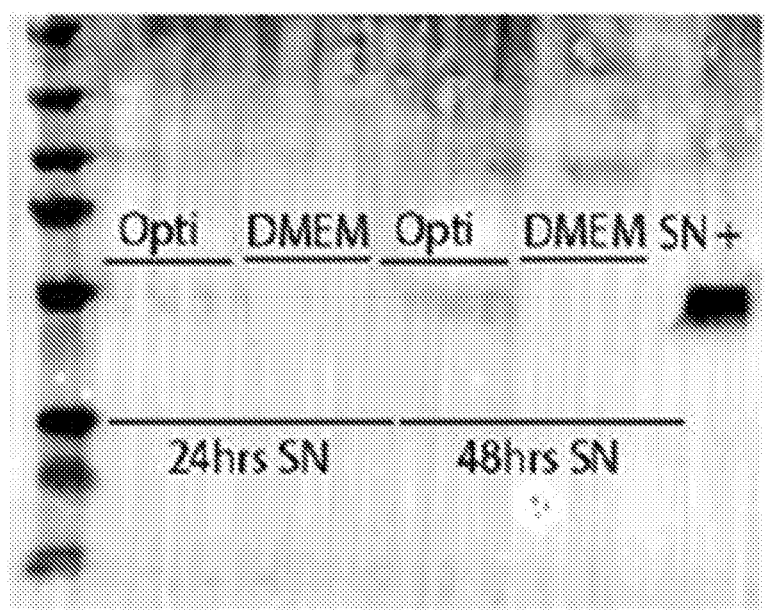
FIG. 2 shows that a full-length bispecific polypeptide can be expressed using the 293T cell line and the lipofectamine system. (A-B) Photographic representations of western blots for His-Tag of protein lysates from 293T cells expressing BEAT1 (9E10-M5/114).
Figure 2:
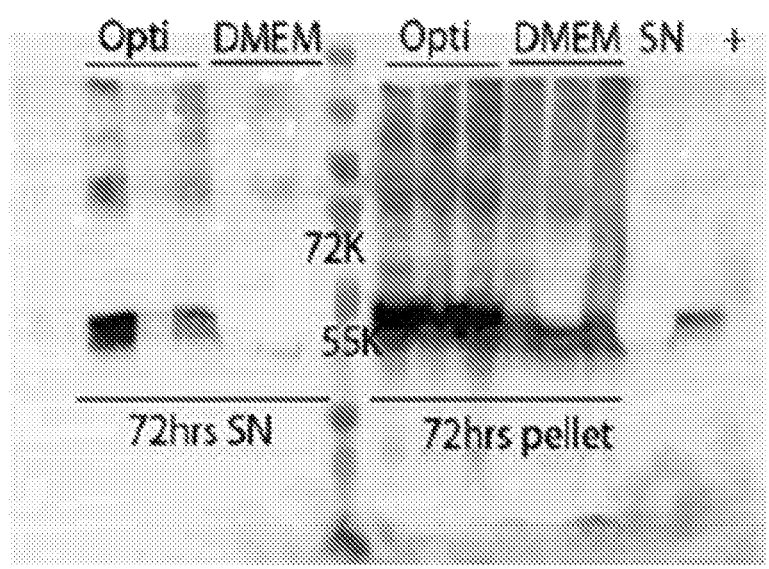
Figure 3:
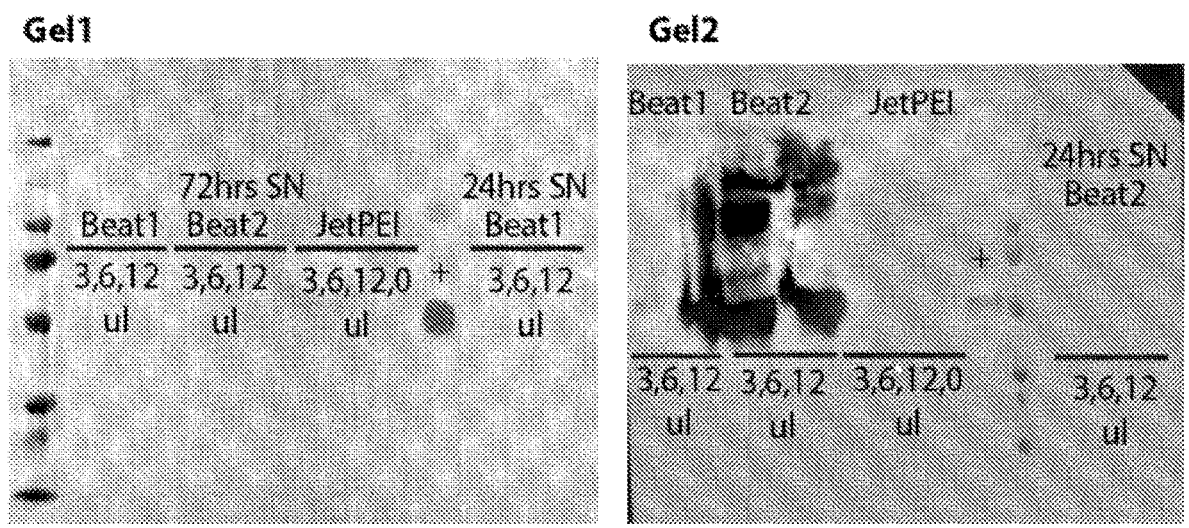
FIG. 3 shows that a full-length bispecific polypeptides can be expressed using the 293T cell line and the jetPEI system. (A-B) Photographic representations of western blots for HisTag of protein lysates from 293T cells expressing BEAT2 (MHCII/c-myc) and BEAT3 (CD40/CD3).
Figure 4:
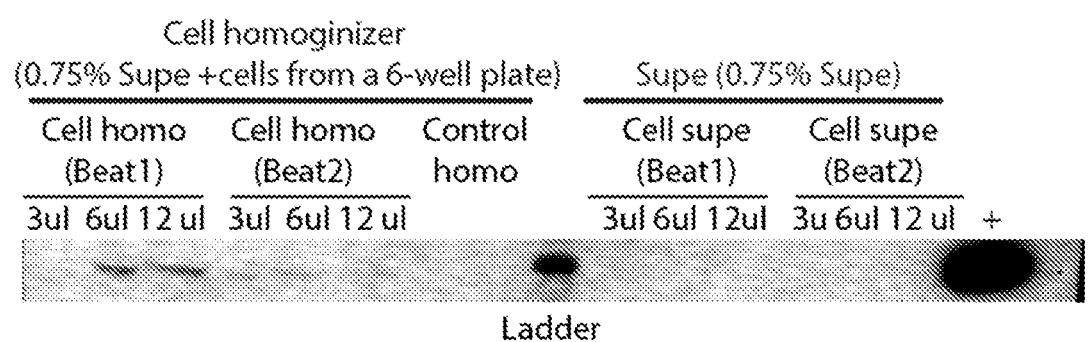
FIG. 4 shows that full-length bispecific polypeptides can be expressed and released from cells after cell homogenization. Photographic representations of western blots for HisTag of protein lysates from 293T cells expressing BEAT2 (MHCII/c-myc) and BEAT3 (CD40/CD3) from (A) homogenized 0.75% Supe+cells from a 6-well plate, and (B) non-homogenised cell pellets from a 6-well plate.
Figure 4:
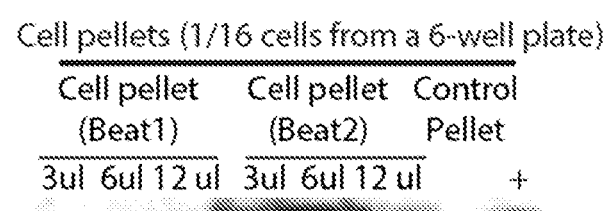

Using the Expi293 cell expression system, scFv was successfully generated for CD3 (CAR-specific; SEQ ID NO: 6; FIG. 1). Full-length BEATs were produced for BEAT2 (MHCII/c-myc); SEQ ID NO: 18) and BEAT3 (CD40/CD3; SEQ ID NO: 20) using both lipofectamine (FIG. 2) and the jetPEI (FIG. 3) systems. The jetPEI system, however, allowed for the more efficient release of the recombinant BEATs following cell homogenisation (FIG. 4).

SEB Enhanced T Cell Proliferation and IFN-γ Secretion In Vitro

SEB is a bispecific polypeptide that specifically binds to MHCII molecules outside the peptide binding grooves on APCs and TCRs on T cells bearing particular TCR Vβ chains, in particular Vβ3, 7, 8 and 17 in mice. The simultaneous binding of SEB to MHCII and TCR stimulates a large number of T cells, both CD4+ and CD8+, leading to their activation and proliferation. Conventional antigens presented by MHCII activate 0.0001-0.001% T cells, whereas bispecific polypeptides, such as SEB, stimulate 2-20% of all T cells (Fraser and Proft, 2008, *Immunology Reviews*, 225:226-43; Arcus et al., 2000, *Journal of Molecular Biology*, 299(1):157-68). Therefore, SEB was used as a proof-of-concept molecule to develop a strategy to activate and expand CAR T cells in vivo, however, the approach and reagents described herein achieve this aim in a more controlled manner with minimal toxicity.

Figure 5:
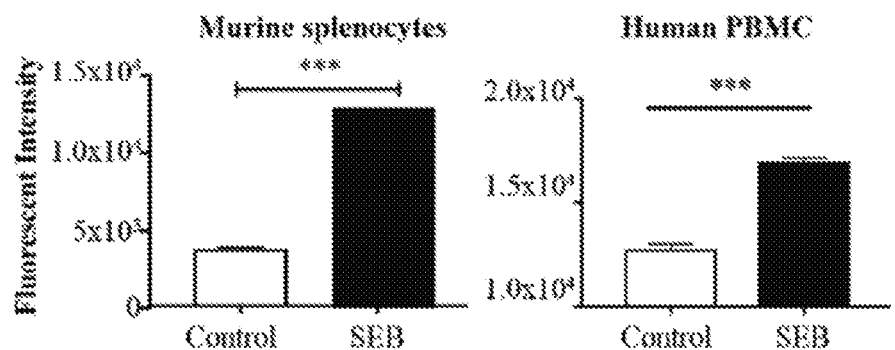
FIG. 5 shows that bispecific polypeptide Staphylococcus Enterotoxin B (SEB) mediates T cell expansion and IFN-γ secretion. (A) A graphical representation of T cell proliferations (y-axis) against splenocytes from a B6 mouse or human PBMC in the presence or absence of SEB (x-axis) (B) A graphical representation of IFN-γ secretion (y-axis) against splenocytes from a B6 mouse or human PBMC in the presence or absence of SEB (x-axis). (C) A graphical representation of the percentage of TCR-Vβ8$^+$ cells in the spleens of mice bearing established E0771-Her2 mammary tumors after 48 hours in the presence or absence of SEB (x-axis). *p<0.05, ***p<0.001 (student t-test).
Figure 5:
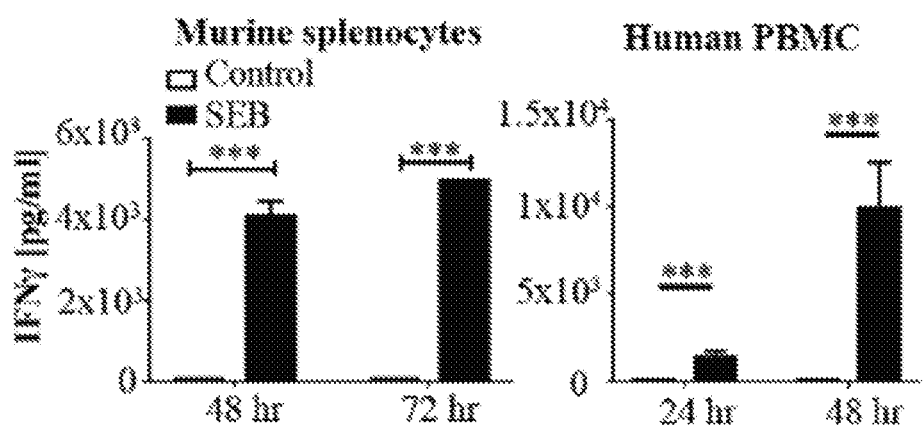
Figure 5:
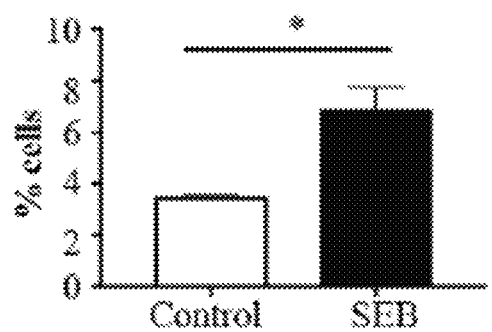

After incubation with SEB, mouse and human T cell expanded to a significantly greater extent (FIG. 5A) and secreted higher amounts of IFN-γ when SEB was present (FIG. 5B). When SEB was injected in mice bearing established E0771-Her2 breast cancers, the percentages of TCR-Vβ8+ (one of the TCRβ types for SEB engagement) cells in the spleen was significantly higher than the untreated group (FIG. 5C).

Figure 6:
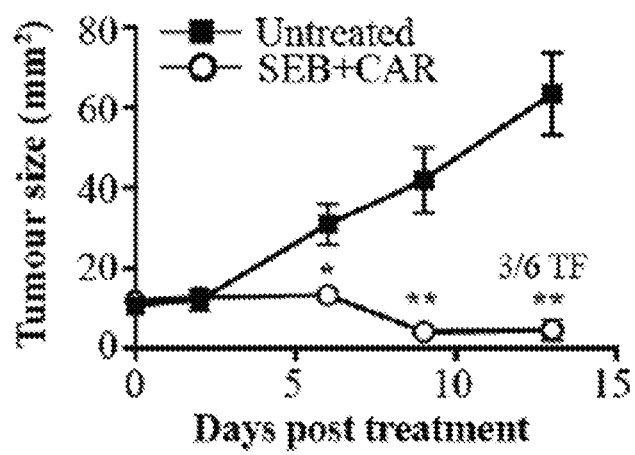
FIG. 6 shows the anti-tumour efficacy of CAR T cells is enhanced by the co-administration of SEB in vivo. (A) A graphical representation of tumour size (mm$^2$; y-axis) against time (days post-treatment; x-axis) in mice bearing established E0771-Her2 breast cancer. (B) A graphical representation of tumour size (mm$^2$; y-axis) against time (days post-treatment; x-axis) in mice bearing established 24JK-Her2 breast cancer. (C) A graphical representation of tumour size (mm$^2$; y-axis) against time (days post-treatment; x-axis) in mice bearing established MC38-Her2 breast cancer. Error bars: SEM. *p<0.05, **p<0.01 (student t-test). (D) A graphical representation of tumour size (mm$^2$; y-axis) against time (days post-treatment; x-axis) in mice bearing established E0771-Her2 breast cancer, including mice receiving just SEB alone or CAR T cells alone. Unless stated, significance was compared between untreated and SEB+CAR groups.
Figure 6:
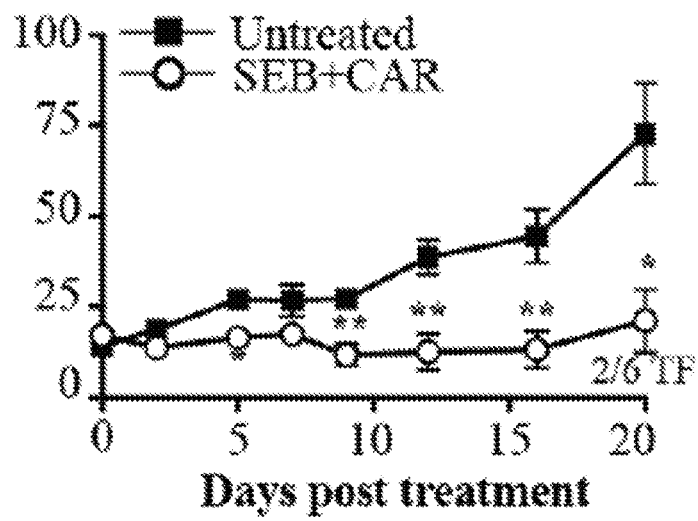
Figure 6:
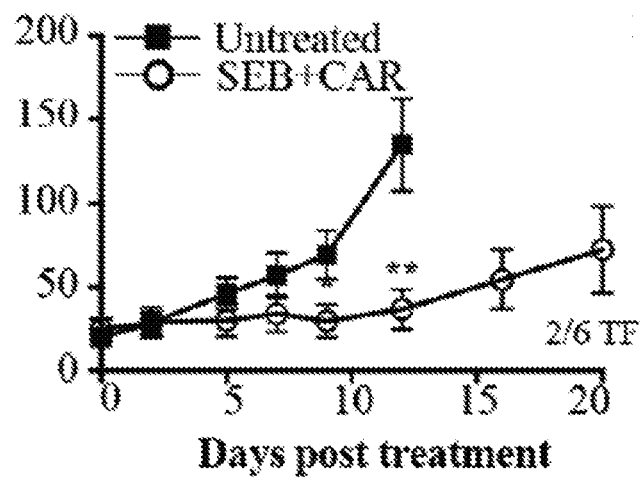
Figure 6:
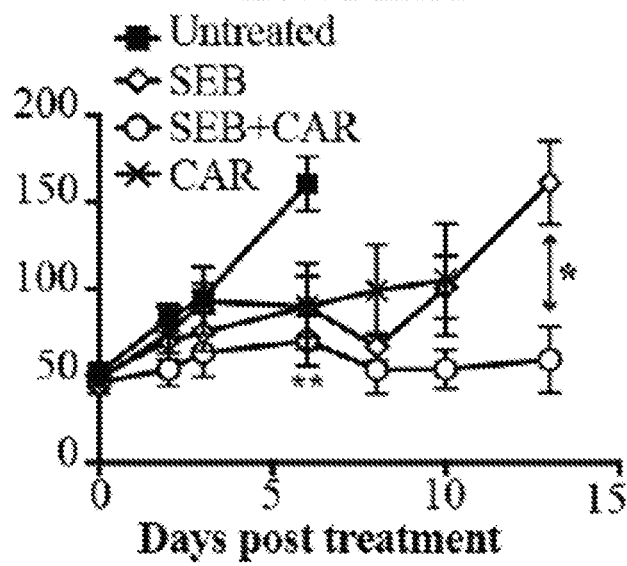

Surprisingly, tumour growth was significantly inhibited in all three murine models following the adoptive transfer of CAR T cells and two doses of SEB, with 30-50% of the mice becoming tumour-free and gaining long-term survival (FIG. 6). Tumours were inhibited to a significantly greater degree in mice receiving the combination of CAR T cells and SEB, when compared to mice that received only CAR T cells or SEB alone.

Figure 7:
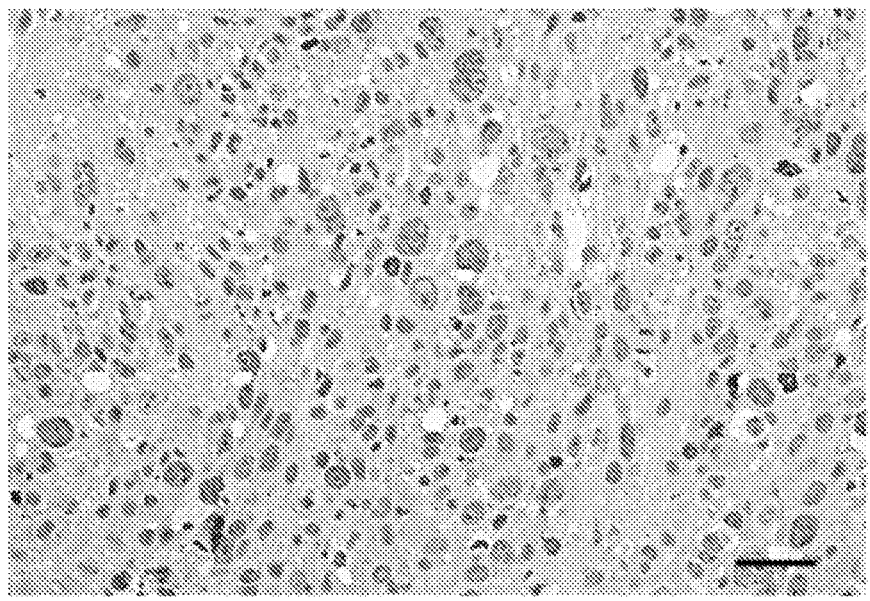
FIG. 7 shows that the infiltration of CAR T cells to tumors is enhanced by co-administration of SEB. A photographic representation of cells stained with CD8 in the (A) absence, or (B) presence of SEB. In CAR+SEB the dark staining represents infiltrating CAR T cells (i.e., CD8+). Scale bar=50 µm.
Figure 7:
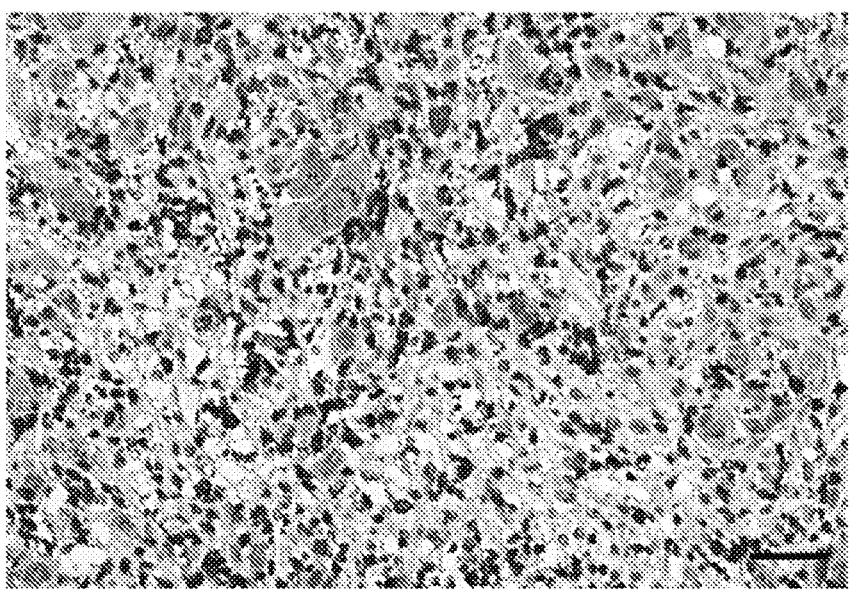

The suppression of the tumours was associated with a >10 fold increase in CAR T cell infiltration into the tumour sites (FIG. 7). It is estimated that the number of CAR T cells per dose that was of the correct Vβ type for engagement of SEB was approximately $2\times10^5$ (10% of all the CAR T cells transferred). The high degree of tumour inhibition without toxicity, observed with such a low effective dose of CAR T cells in an immunocompetent model represents a significant and unexpected result when compared to other known effective doses for CAR T cells, and suggests that even greater efficacy should be possible if the engagement of CAR T cells with APCs occurs in a non-MHC-restricted or non-Vβ-restricted manner.

Activation and Expansion of CAR T Cells by BEATs

Figure 8:
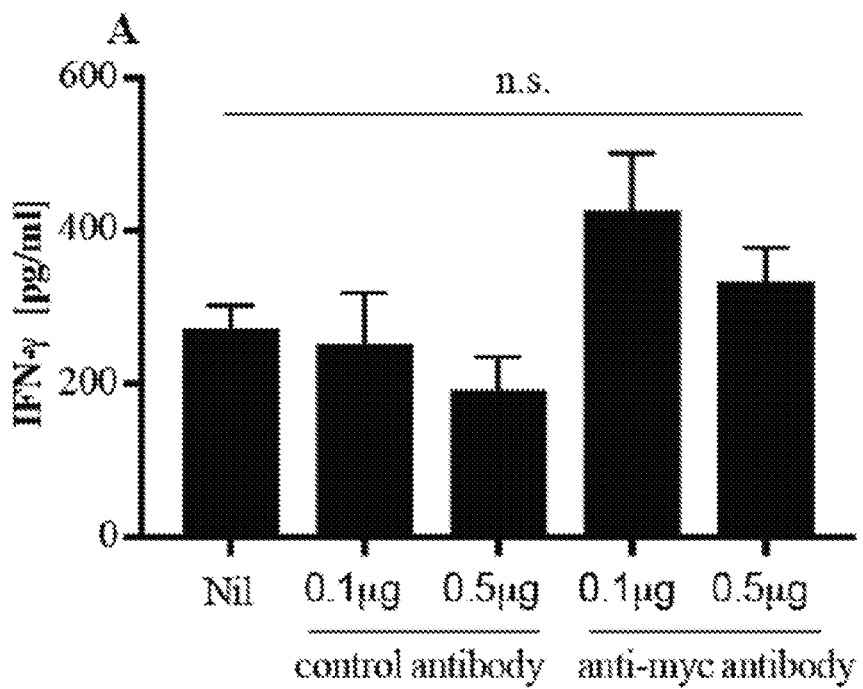
FIG. 8 shows that binding of CAR-specific binding domain does not interfere with CAR-mediated T cell function. (A) A graphical representation of IFN-γ secretion (pg/mL; y-axis) of CAR T cells incubated with E0771-Her2 cells and control or anti-myc antibodies (y-axis). (B) A graphical representation of cytotoxicity (% killing; y-axis) of CAR T cells co-cultured with E0771-Her2 cells in the presence or absence of anti-myc antibody (x-axis).
Figure 8:
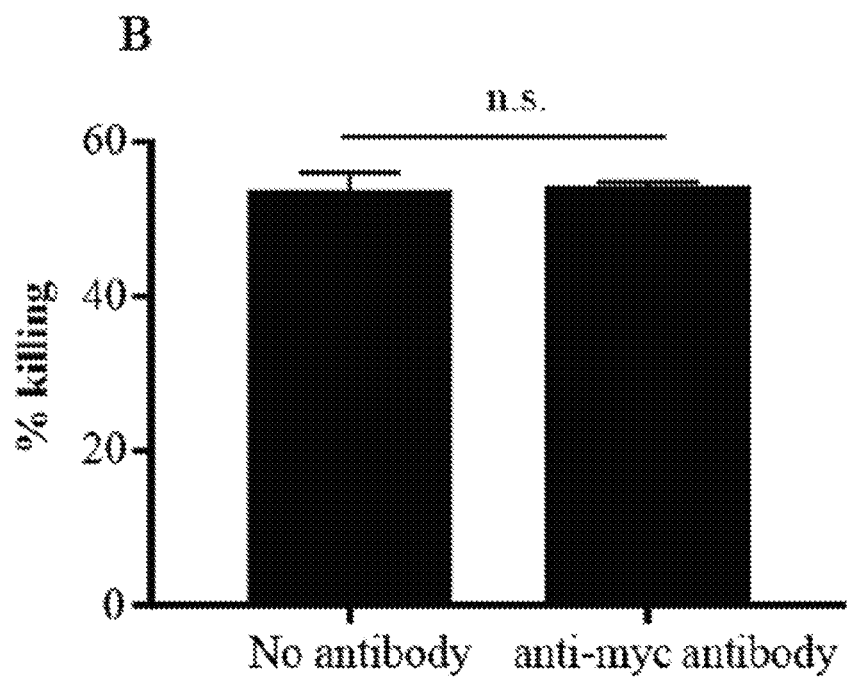
Figure 9:
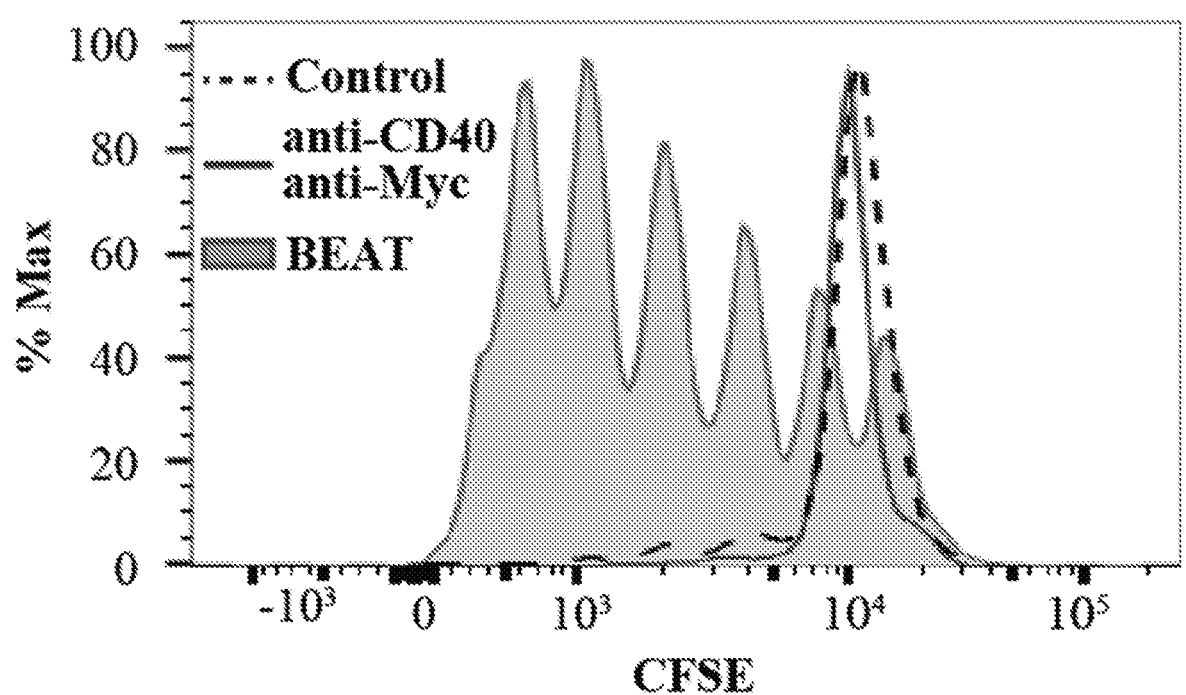
FIG. 9 shows that a bispecific polypeptide (i.e., BEAT) promotes CAR T cell proliferation in vitro. A graphical representation of cell number of splenocytes from transgenic CAR mice labelled with CSFE and incubated with BEAT (anti-CD40/anti-myc) or a mixture of anti-CD40 and anti-myc antibodies for 72 hours.

Importantly, it was confirmed that binding of anti-myc to CAR T cells does not interfere with CAR-mediated T cell function (FIG. 8). Furthermore, it was also demonstrated that the chemically conjugated bispecific polypeptide greatly enhanced CAR T cell proliferation in vitro (FIG. 9). In contrast, the combination of the two single antibodies at the same molar concentration did not mediate CAR T cell proliferation. These data suggest that the bispecific polypeptide can engage APCs with CAR T cells, and that this engagement leads to enhanced CAR T cell production.

BEATs Mediate CAR T Cell Activation and Proliferation

Three examples of BEATs were generated by chemically conjugating an antibody specific for myc-tag (present in the CAR) to an antibody specific for either CD40, PD-L2 or Clec9a, which are expressed on various subsets of APCs. Mouse CAR T cells were incubated with mouse splenocytes (as a source of APCs) in the presence or absence of a BEAT. T cells lacking expression of a CAR were used as controls. Incubation of CAR T cells with APCs in the presence of unconjugated antibodies were also used as controls.

Figure 10:
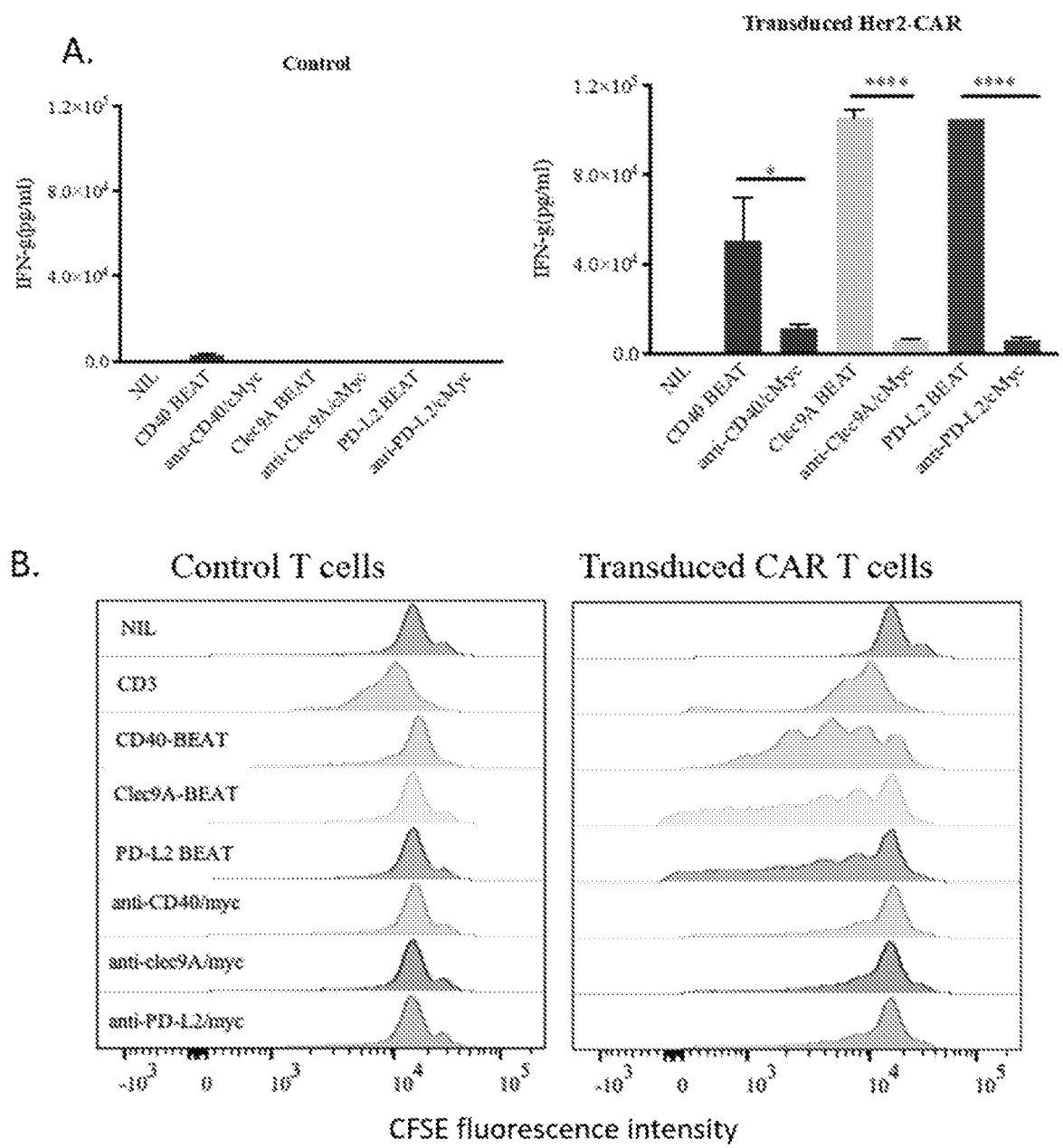
FIG. 10 shows that BEATs mediate CAR T cell activation and proliferation. Three examples of BEATs were generated by chemically conjugating an antibody specific for myc-tag (present in the CAR) to an antibody specific for either CD40, PD-L2 or Clec9a, which are expressed on various subsets of APCs. Mouse CAR T cells were incubated with mouse splenocytes (as a source of APCs) in the presence or absence of a BEAT. T cells lacking expression of a CAR were used as controls. Incubation of CAR T cells with APCs in the presence of unconjugated antibodies (as listed) were also used as controls. (A) CAR T cells (right panel), but not control T cells (left panel), secrete IFN-γ in the presence of each BEAT. (B) CAR T cells were loaded with the fluorescent dye CFSE and incubated with APCs in the presence or absence of each alternate BEAT. The extent of proliferation is evident from a reduction in fluorescence intensity of transduced CAR T cells (right panel) compared to control non-transduced T cells (left panel).

The results shown in FIG. 10 demonstrate that CAR T cells but not control T cells secrete IFN-γ in the presence of each BEAT. (FIG. 10A).

CAR T cells were loaded with the fluorescent dye CFSE and incubated with APCs in the presence or absence of each alternate BEAT. The extent of proliferation is evident from a reduction in fluorescence intensity of transduced CAR T cells compared to control non-transduced T cells (FIG. 10B)

Together, these results demonstrate that BEATs can activate CAR T cells and induce their proliferation. In addition, it shows that a variety of APC molecules and APC subsets can be used as BEAT targets.

A CD40-myc BEAT Enables Eradication of E0771-Her2 Breast Cancer in Mice

Her2-transgenic mice bearing established subcutaneous E0771-Her2 tumors were treated with CAR T cells ($2\times10^6$, i.v.) and/or a BEAT specific for myc-CD40 (36 µg on Day 0, i.p.). Other mouse groups received unconjugated anti-myc and anti-CD40 antibodies, or were left untreated (Control).

Figure 11:
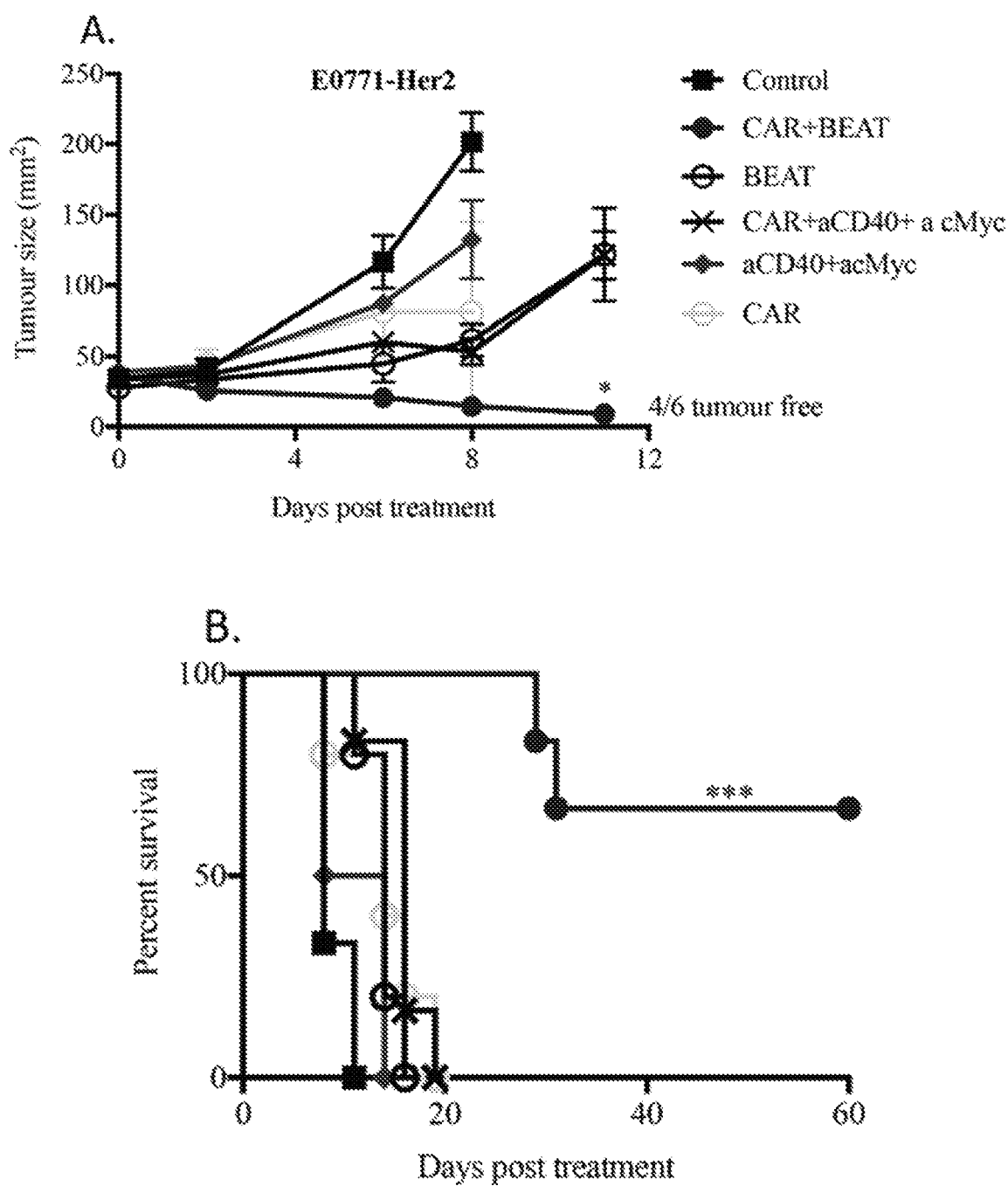
FIG. 11 shows a CD40-myc BEAT enables eradication of E0771-Her2 breast cancer in mice. Her2-transgenic mice bearing established subcutaneous E0771-Her2 tumors were treated, as listed, with CAR T cells ($2 \times 10^6$, i.v.) and/or a BEAT specific for myc-CD40 (36 µg on Day 0, i.p.). Other mouse groups received unconjugated anti-myc and anti-CD40 antibodies, or were left untreated (Control). (A) Tumor growth and (B) Mouse survival. Data representative of 3 independent experiments with 6 mice per group. *$p<0.05$, ***$p<0.001$ Unpaired student t-test.

The results in FIG. 11 show tumor growth and mouse survival following administration of BEATs in conjunction with CAR T cells. The data demonstrate the ability of the CD40-myc BEAT to enable CAR T cell-mediated eradication of established breast cancer tumors in immunocompetent mice that express Her2 in normal breast and brain.

A CD40-myc BEAT Enables Accumulation of T Cells in Tumors

Mice bearing subcutaneous E0771-Her2 tumors received anti-HER2 CAR T cells ($2\times10^6$, i.v.) together with a CD40-myc BEAT (36 µg on Day 0, i.p). Other mice received CAR T cells or BEAT alone or were left untreated (Control).

On day 7 after the start of treatment, tumors were taken, dissociated, stained to detect CD8+ T cells and analyzed using flow cytometry. Data representative of 3 individual mice per group. Tumors were formalin fixed, sectioned and stained with DAPI (blue) and anti-CD8 (brown). Images representative of 3 sections are shown from mice receiving the treatments listed.

Figure 12:
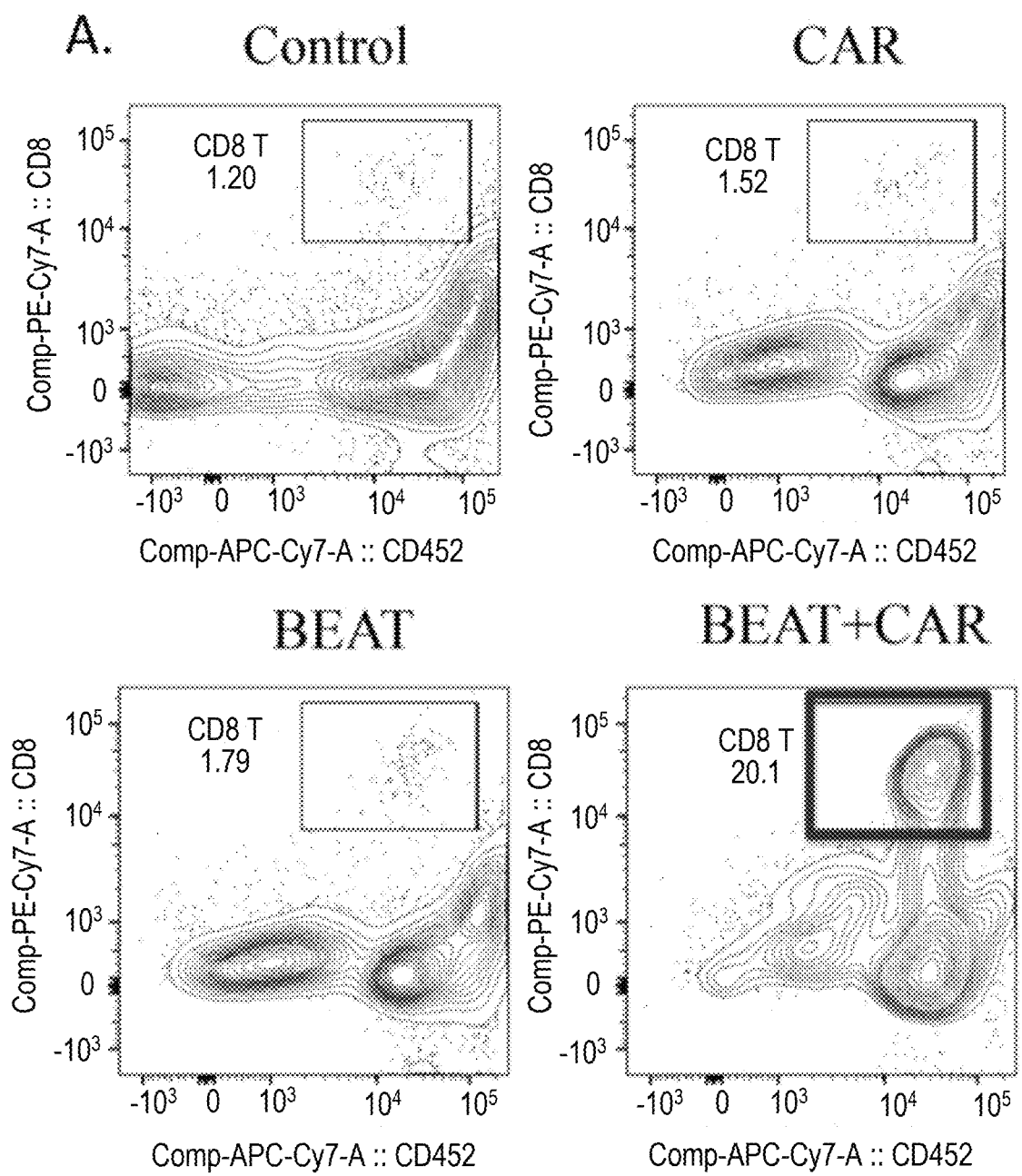
FIG. 12 shows a CD40-myc BEAT enables accumulation of T cells in tumors. Mice bearing subcutaneous E0771-Her2 tumors received anti-HER2 CAR T cells ($2 \times 10^6$, i.v.) together with a CD40-myc BEAT (36 µg on Day 0, i.p). Other mice received CAR T cells or BEAT alone or were left untreated (Control). (A) On Day 7 after the start of treatment tumors were taken, dissociated, stained to detect CD8+ T cells and analyzed using flow cytometry. Data representative of 3 individual mice per group. (B) Tumors were formalin fixed, sectioned and stained with DAPI (blue) and anti-CD8 (brown). Images representative of 3 sections are shown from mice receiving the treatments listed.
Figure 12:
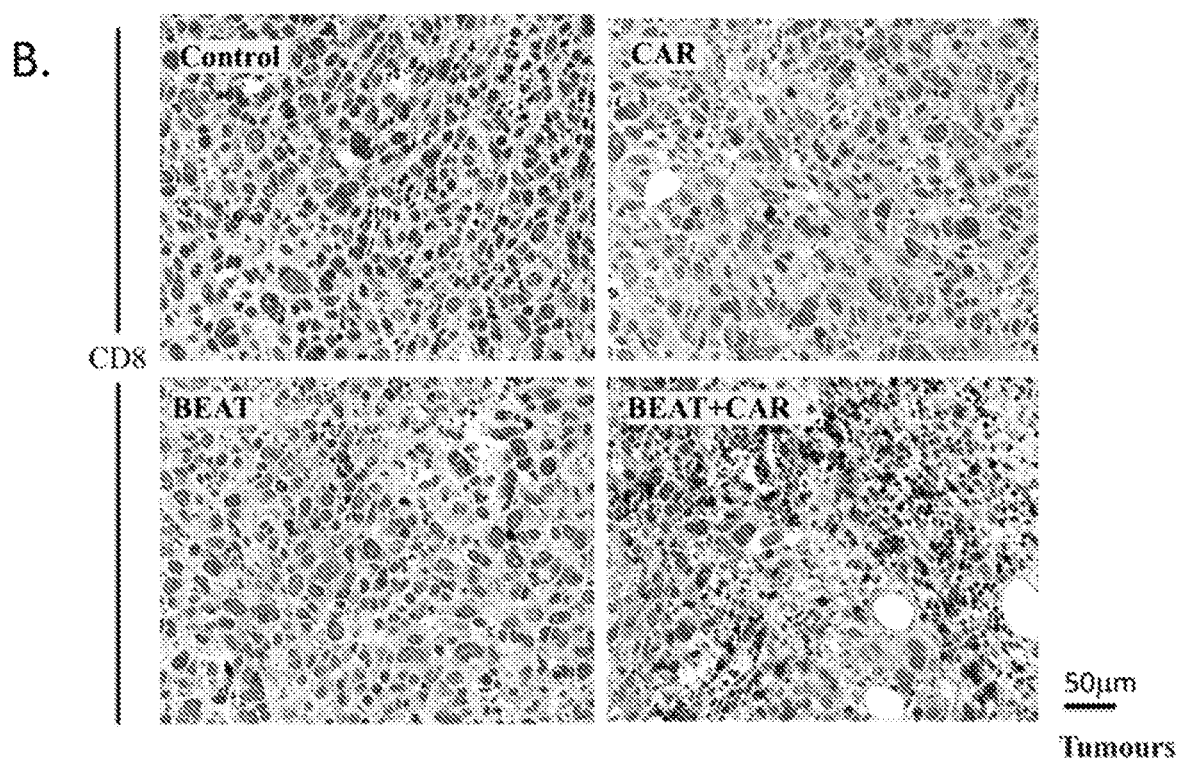

The results, shown in FIG. 12, demonstrate the ability of BEATs to enable CAR T cells to accumulate in tumors to a much greater degree than in the absence of BEAT.

CAR T Cells Persist Long Term in Mice

Spleens were taken from long-term (>200 days) surviving mice following eradication of E0771-Her2 tumors by CAR T cells+CD40-myc BEAT or from naïve mice, and stained with anti-myc and CD8 to detect CAR T cells. Data representative of 3 mice.

Figure 13:
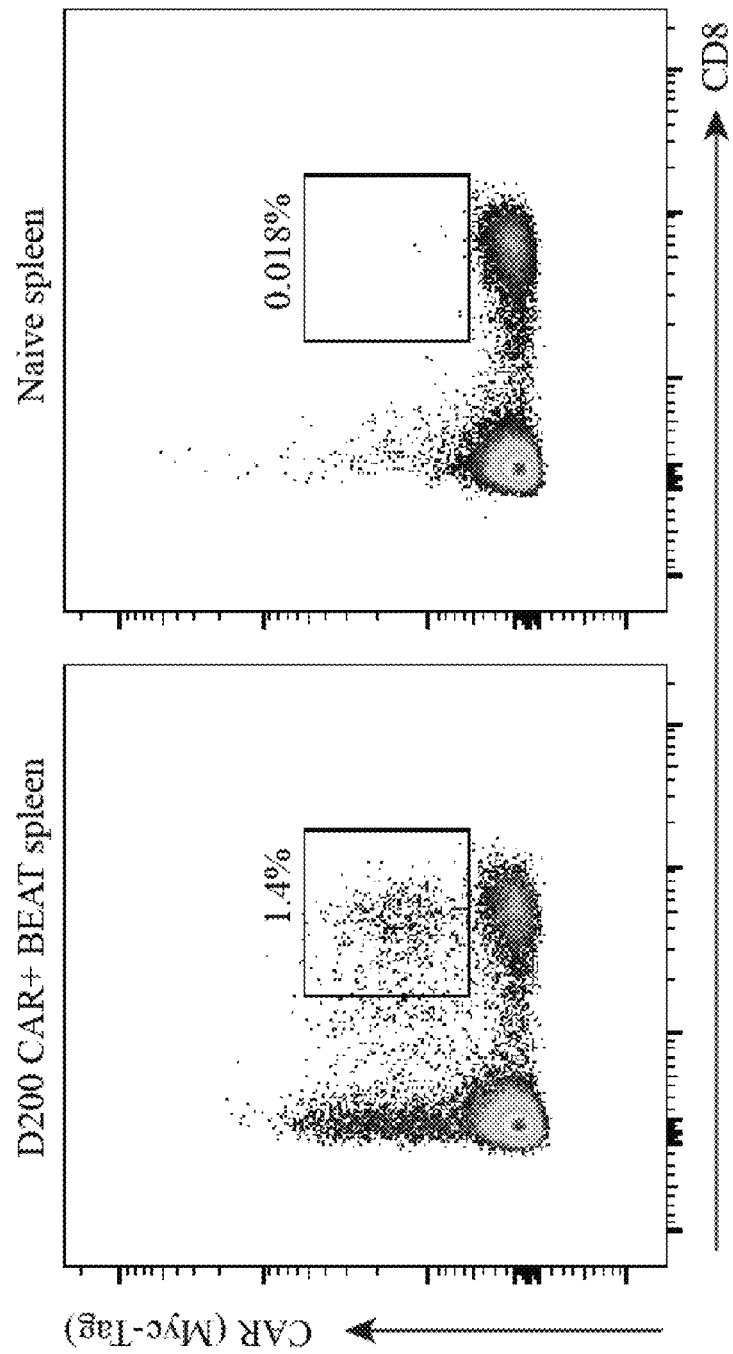
FIG. 13 shows CAR T cells persist long term in mice. Spleens were taken from long-term (>200 days) surviving mice following eradication of E0771-Her2 tumors by CAR T cells+CD40-myc BEAT (left panel) or from naïve mice (right panel), and stained with anti-myc and CD8 to detect CAR T cells. Data representative of 3 mice.

The data shown in FIG. 13 demonstrate the ability of a BEAT to enable long-term persistence of CAR T cells in mice, suggesting mice would be protected from tumor rechallenge.

Figure 14:
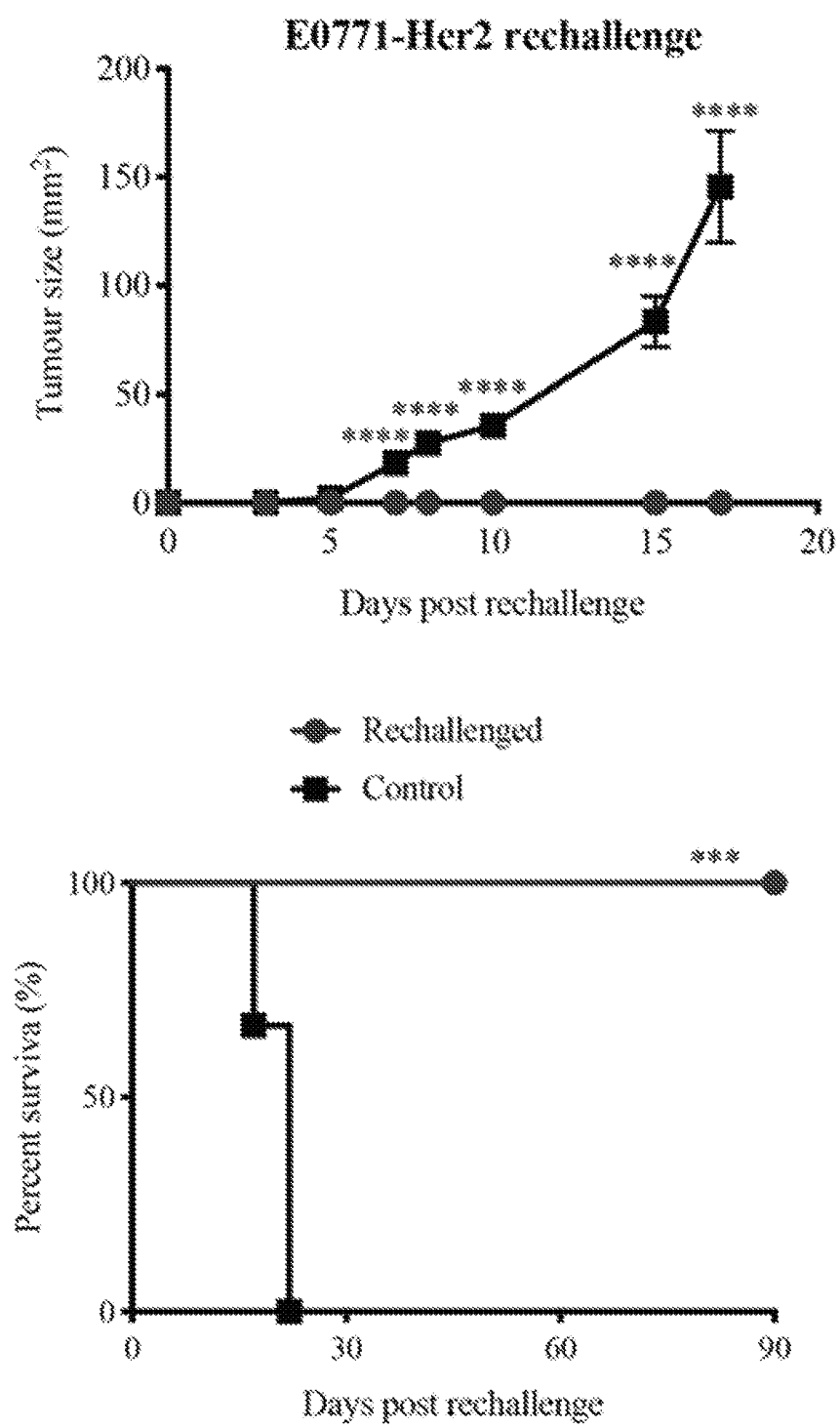
FIG. 14 shows mice that rejected Her2-positive tumors following CAR T cell+BEAT therapy are completely resistant to rechallenge with Her2-positive tumors. Long-term surviving mice that had eradicated subcutaneous E0771-Her2 tumors, mediated by Her2-specific CAR T cells and CD40-myc BEAT, were rechallenged subcutaneously on the opposite flank with the same Her2-positive tumor cells ($5 \times 10^5$). Tumor growth (upper panel) and mouse survival (lower panel). Tumor growth is depicted in naïve mice as a control. (8 mice in the rechallenged group and 6 mice in the control *$p<0.001$, **$p<0.0001$).

Mice That Rejected Her2-Positive Tumors Following CAR T Cell+BEAT Therapy are Completely Resistant to Rechallenge with Her2-Positive Tumors Long-term surviving mice that had eradicated subcutaneous E0771-Her2 tumors, mediated by Her2-specific CAR T cells and CD40-myc BEAT, were rechallenged subcutaneously on the opposite flank with the same Her2-positive tumor cells ($5\times10^5$). Tumor growth (upper panel) and mouse survival (lower panel) are shown in FIG. 14. Tumor growth is depicted in naïve mice as a control. (8 mice in the rechallenged group and 6 mice in the control group. *$p<0.001$, **$p<0.0001$).

These data support a conclusion that persisting (engrafted) CAR T cells, following CAR T+BEAT therapy, are able to react against subsequent relapse of Her2-positive tumors.

Figure 15:
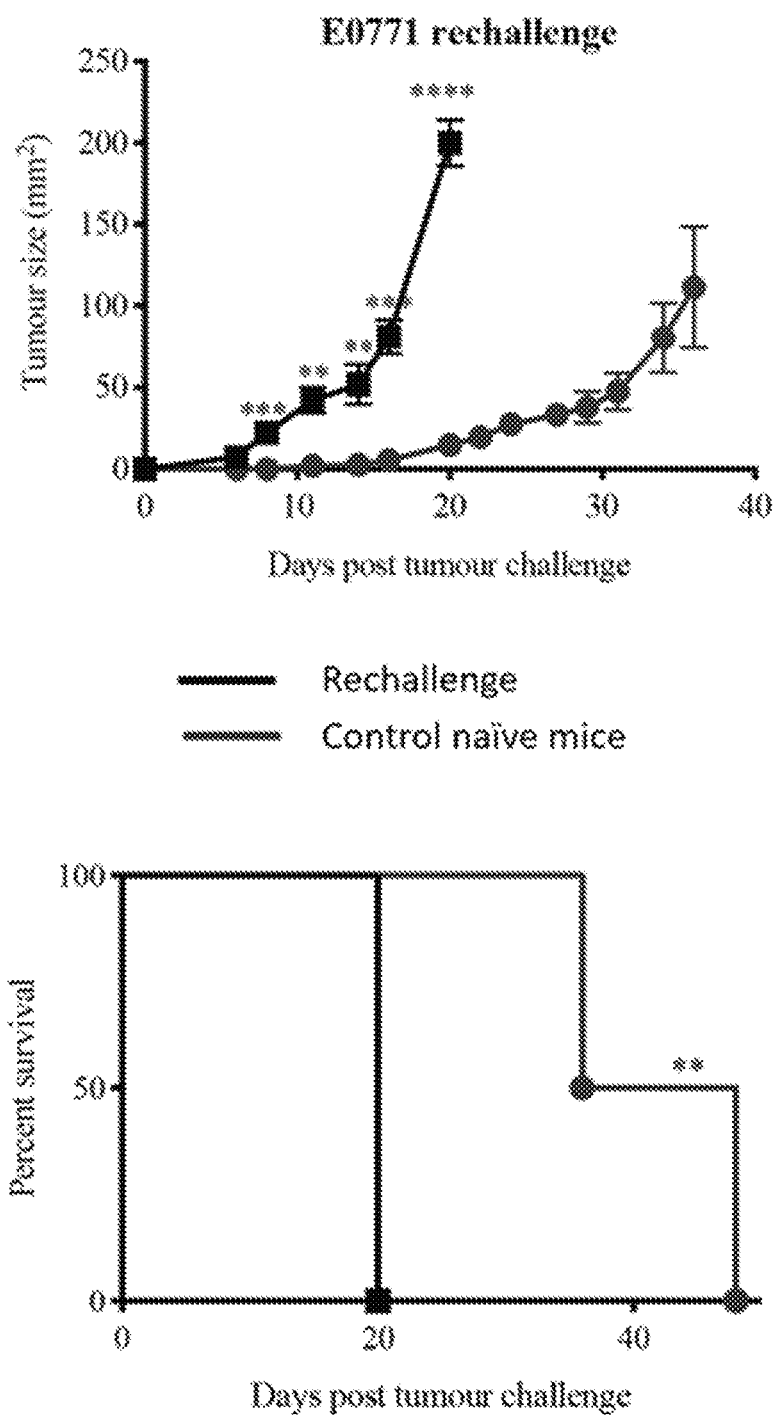
FIG. 15 shows Her2-negative tumor growth is inhibited in mice that had rejected Her2-positive tumors mediated by CAR T cells and BEAT therapy. Mice that had previously rejected E0771-Her2 tumors following Her2-specific CAR T cells+CD40-myc BEAT, were rechallenged in the opposite flank with E0771 lacking Her2 expression ($5 \times 10^5$ cells). Tumor growth in naïve mice is presented as a control. Tumor growth (upper panel) and mouse survival (lower panel). (15 mice in the rechallenged group and 5 mice in the control group. $p<0.01$, *$p<0.001$, ****$p<0.0001$).

Her2-Negative Tumor Growth is Inhibited in Mice That had Rejected Her2-Positive Tumors Mediated by CAR T Cells and BEAT Therapy Mice that had previously rejected E0771-Her2 tumors following Her2-specific CAR T cells+CD40-myc BEAT, were rechallenged in the opposite flank with E0771 lacking Her2 expression ($5\times10^5$ cells). Tumor growth in naïve mice is presented as a control. Tumor growth (upper panel) and mouse survival (lower panel) are shown in FIG. 15 (4 mice in the rechallenged group and 5 mice in the control group. $p<0.01$, *$p<0.001$, ****$p<0.0001$).

These data indicate that CAR T cell+BEAT therapy induces epitope spreading, whereby T cells of other specificities, different from Her2, have been induced and which can participate in anti-tumor activity.

Anti-Her2 CAR T Cells Combined with a CD40-myc Conjugated BEAT Inhibit Growth of MC38-Her2 Colon Cancer in Mice Mice bearing established subcutaneous MC38-Her2 tumors were treated with anti-Her2 CAR T cells ($2\times10^6$, i.v.) and CD40-myc BEAT (36 µg on Day 0). Other groups of mice received various treatments of CAR T cells or antibodies alone (as listed) or remained untreated (Control). (6 mice per group, except BEAT+CAR group has 7 mice. **$p<0.01$).

Figure 16:
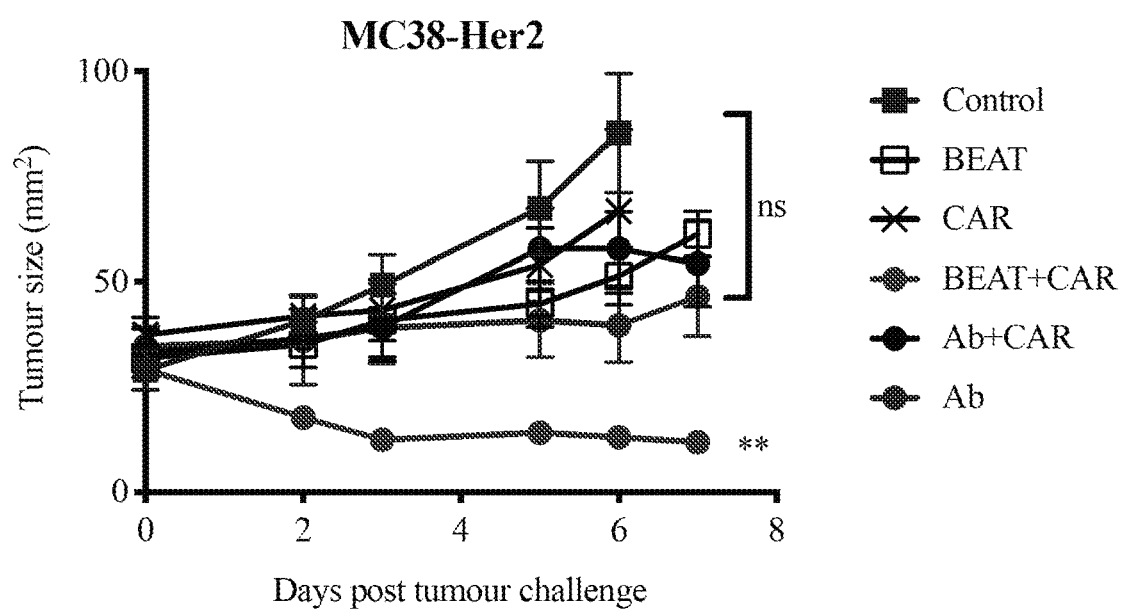
FIG. 16 shows Anti-Her2 CAR T cells combined with a CD40-myc conjugated BEAT inhibit growth of MC38-Her2 colon cancer in mice. Mice bearing established subcutaneous MC38-Her2 tumors were treated with anti-Her2 CAR T cells ($2 \times 10^6$, i.v.) and CD40-myc BEAT (36 µg on Day 0). Other groups of mice received various treatments of CAR T cells or antibodies alone (as listed) or remained untreated (Control). 6 mice per group, except BEAT+CAR group had 7 mice. **$p<0.01$).

The results, shown in FIG. 16, indicate that tumor types other than breast cancer can be controlled using CAR T cells+BEAT.

PD-L2-myc and Clec9a BEAT Conjugates Enable CAR T Cell Inhibition of Tumor Growth BEATs specific for the APC-expressed molecules PD-L2 or Clec9a were prepared by chemical conjugation of the monoclonal antibody to the anti-myc antibody. Mice bearing established subcutaneous E0771-Her2 tumors received the listed treatments, or were left untreated (Control). (3-6 mice per group. *$p<0.05$, **$p<0.01$).

Figure 17:
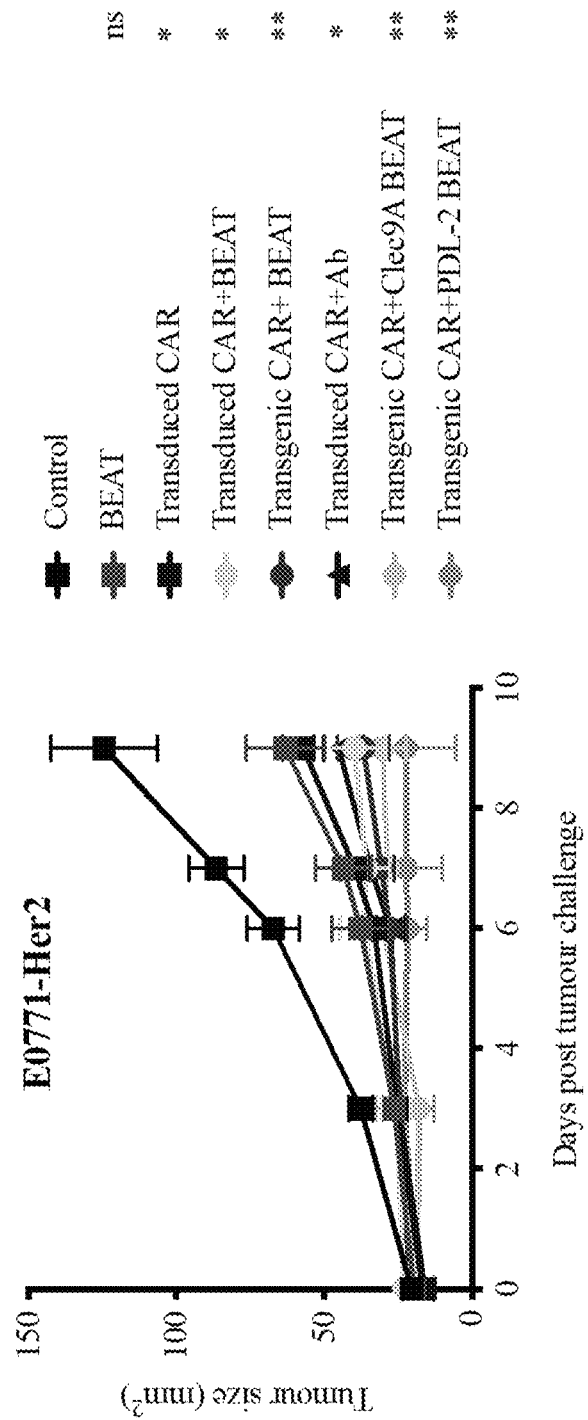
FIG. 17 shows PD-L2-myc and Clec9a BEAT conjugates enable CAR T cell inhibition of tumor growth. BEATs specific for the APC-expressed molecules PD-L2 or Clec9a were prepared by chemical conjugation of the monoclonal antibody to the anti-myc antibody. Mice bearing established subcutaneous E0771-Her2 tumors received the listed treatments, or were left untreated (Control). (3-6 mice per group. *$p<0.05$, **$p<0.01$).

The results, shown in FIG. 17, demonstrate that BEATs specific for several different molecules found on a variety of APC subsets can enhance CAR T cell responses against tumors in mice.

A Recombinant Human CD40-myc BEAT Mediates Proliferation of Human CAR T Cells

CAR T cells were generated from human peripheral blood using retroviral transduction of a Her2-specific CAR. CAR T cells ($2\times10^5$/ml) were labelled with CFSE and incubated for 5 days, with or without a chemically conjugated- or recombinant-CD40-myc BEAT (conjugated 3 µg/ml, recombinant 0.5 µg/ml), in the presence of 5 Gy irradiated CTV-labelled human blood leukocytes, as a source of APCs. T cells transduced with an empty vector served as controls. Cells were analyzed using flow cytometry.

Figure 18:
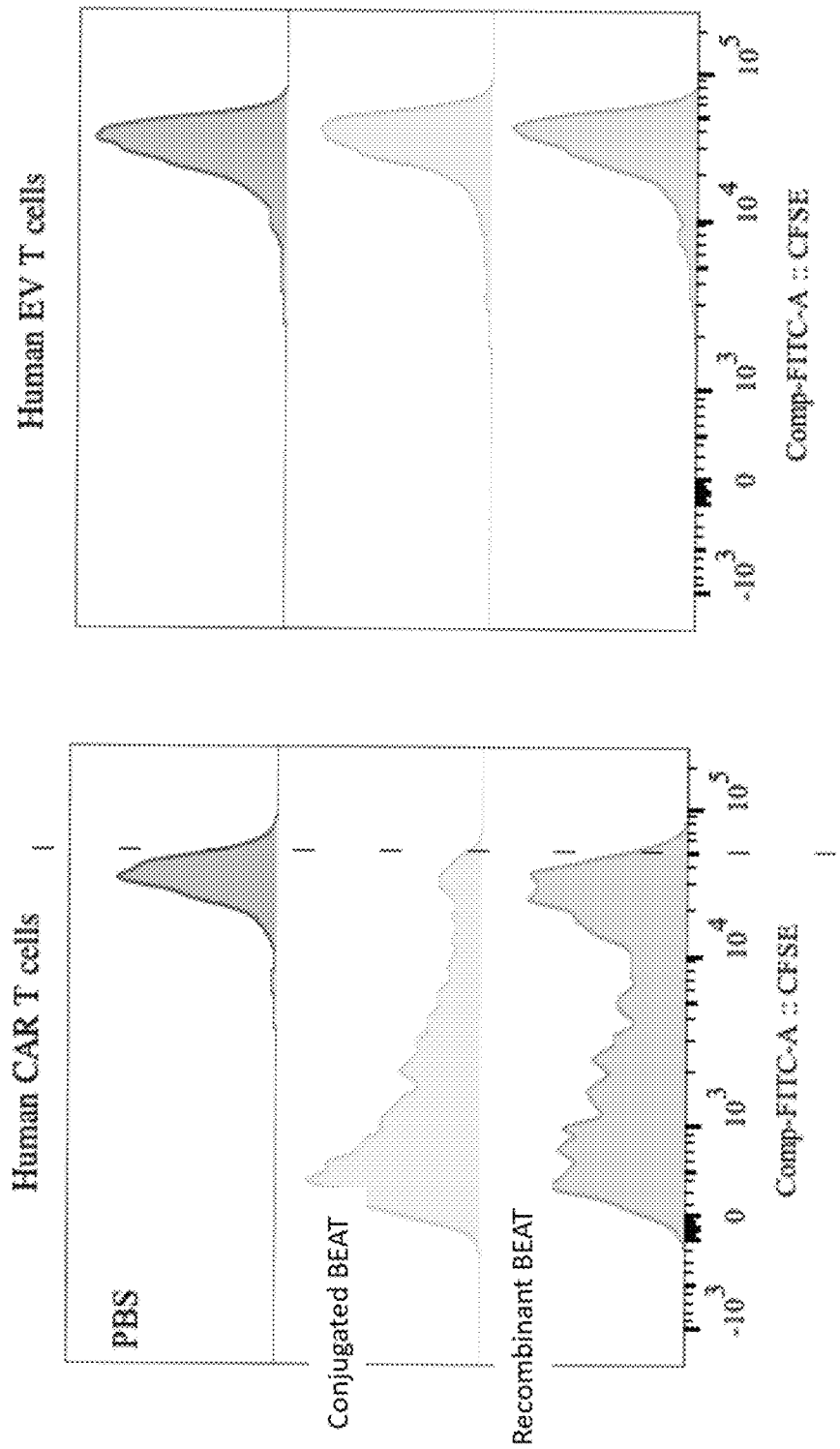
FIG. 18 shows a recombinant human CD40-myc BEAT mediates proliferation of human CAR T cells. CAR T cells were generated from human peripheral blood using retroviral transduction of a Her2-specific CAR. CAR T cells ($2 \times 10^5$/ml) were labelled with CFSE and incubated for 5 days, with or without a chemically conjugated- or recombinant-CD40-myc BEAT (conjugated 3 µg/ml, recombinant 0.5 µg/ml), in the presence of 5 Gy irradiated CTV-labelled human blood leukocytes, as a source of APCs (Left panel). T cells transduced with an empty vector served as controls (Right panel). Cells were analyzed using flow cytometry.

The results, shown in FIG. 18, demonstrate that BEATs using an anti-human CD40 linked to anti-myc can mediate human CAR T cell proliferation. It further demonstrates that a recombinant BEAT is similarly effective as a chemically conjugated BEAT at mediating CAR T cell proliferation.

A Recombinant Human CD40-myc BEAT Enhances IFN-γ Secretion From CAR T Cells

Human CAR T cells were generated from peripheral blood using a retroviral vector encoding an anti-Her2 CAR. CAR T cells were incubated with human blood leukocytes as a source of APCs for 5 days in the presence or absence of chemically- or recombinantly-prepared CD40-myc BEAT. Anti-CD3 was included in some culture wells as a positive control. Supernatants were taken and analyzed for IFN-γ using ELISA.

Figure 19:
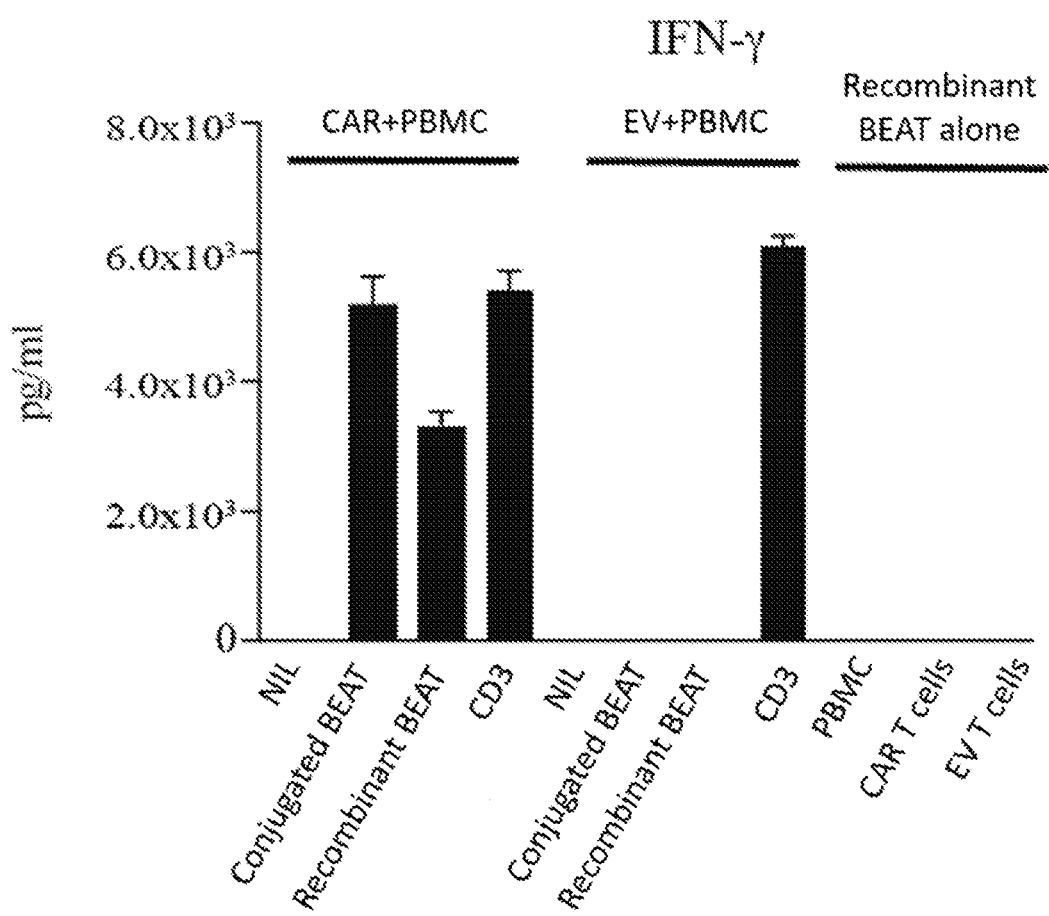
FIG. 19 shows a recombinant human CD40-myc BEAT enhances IFN-γ secretion from CAR T cells. Human CAR T cells were generated from peripheral blood using a retroviral vector encoding an anti-Her2 CAR. CAR T cells were incubated with human blood leukocytes as a source of APCs for 5 days in the presence or absence of chemically- or recombinantly-prepared CD40-myc BEAT. Anti-CD3 was included in some culture wells as a positive control. Supernatants were taken and analyzed for IFN-γ using ELISA.

As shown in FIG. 19, recombinant BEAT can activate human CAR T cells to secrete IFN-γ.

Human CAR T Cells Combined With a Conjugated Human BEAT Inhibit Tumor Growth in Mice Nod-SCID-gamma (NSG) mice, bearing established subcutaneous MDA-MB-231 human breast tumors, received CAR T cells with or without a conjugated human CD40-myc BEAT (36 µg on Day 0, i.p.). Human blood-derived leukocytes ($1\times10^6$) were also delivered intravenously to serve as a source of APCs. One group of mice remained untreated as a control. (5 mice per group, *$p<0.05$, $p<0.01$, *$p<0.001$, student t test)

Figure 20:
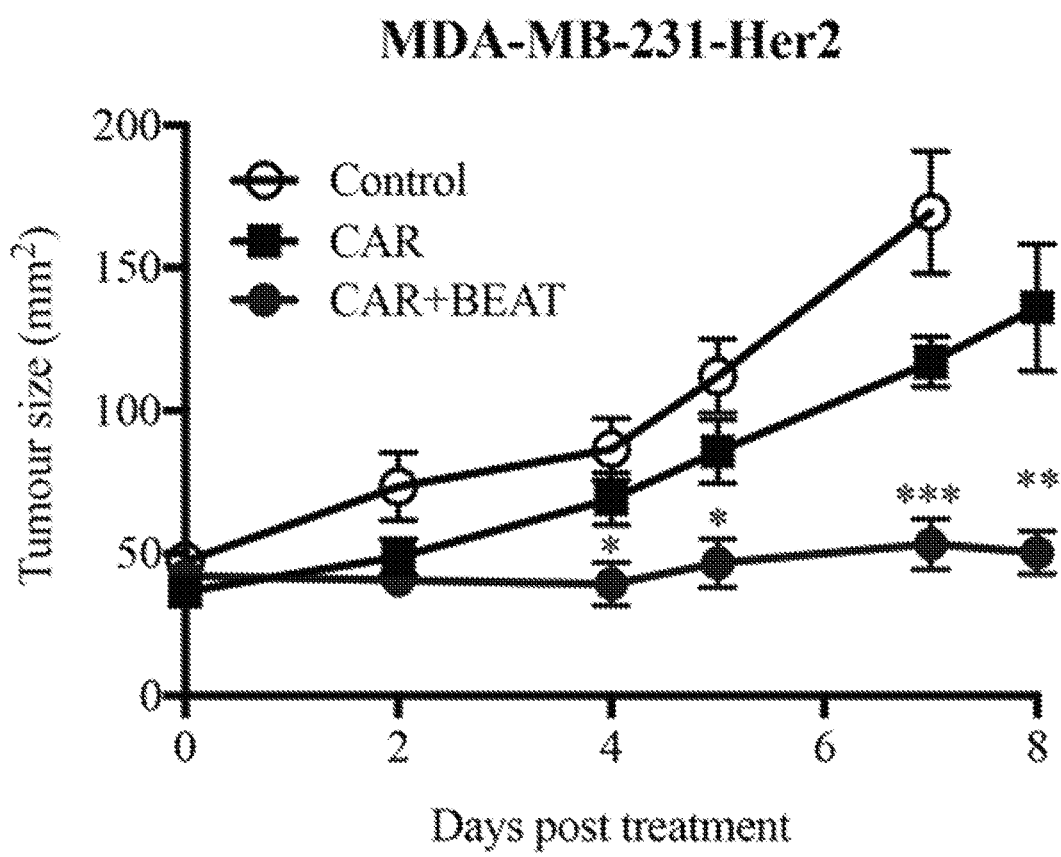
FIG. 20 shows human CAR T cells combined with a conjugated human BEAT inhibit tumor growth in mice. Nod-SCID-gamma (NSG) mice, bearing established subcutaneous MDA-MB-231 human breast tumors, received CAR T cells with or without a conjugated human CD40-myc BEAT (36 µg on Day 0, i.p.). Human blood-derived leukocytes ($1 \times 10^6$) were also delivered intravenously to serve as a source of APCs. One group of mice remained untreated as a control. (5 mice per group, *$p<0.05$, $p<0.01$, *$p<0.001$, student t test).

The data, as shown in FIG. 20, demonstrate the ability of a BEAT to boost the efficacy of human CAR T cells against human cancer established in mice.

BEATs Specific for a Range of Antigens Located in a Variety of Positions within CARs Can Induce Responses From CAR T Cells The ability of BEATs specific for a range of antigens within CARs was assessed by generating CARs with antigens (i.e., affinity tags) incorporated at different locations within the CAR. In particular, a carcinoembryonic antigen (CEA)-specific CAR was prepared incorporating a myc antigen located centrally in the CAR, and a Her2-FLAG CAR was prepared incorporating a FLAG antigen within the amino terminus of the CAR.

$5\times10^5$ mouse CAR T cells bearing the CEA-myc CAR or the Her2-FLAG CAR were incubated with $5\times10^5$ CD40-positive mouse splenocytes (as a source of APCs) in the presence or absence of BEATs specific for the APC-expressed molecule CD40 prepared by chemical conjugation of the monoclonal antibody to the anti-myc antibody (BEAT1; as described elsewhere herein), or BEATs specific for the APC-expressed molecule CD40 prepared by chemical conjugation of the monoclonal antibody to the anti-FLAG antibody (BEATS). Untransduced splenocytes were used as controls. Incubation of CAR T cells with APCs in the presence of unconjugated antibodies were also used as controls. Secretion of IFN-γ was determined by ELISA at 72 hours post co-culture.

Figure 21:
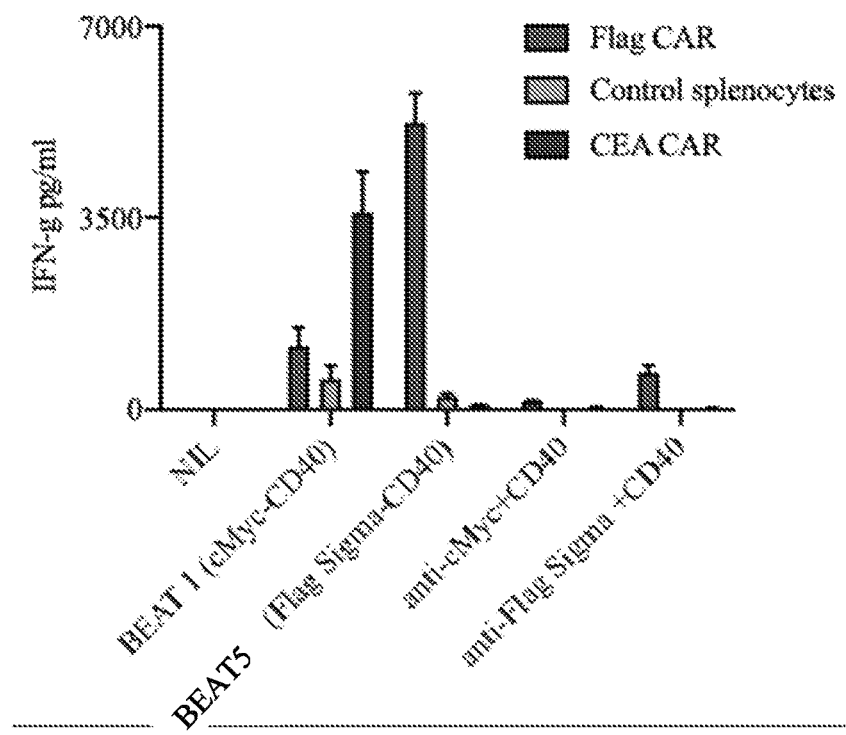
FIG. 21 shows that BEATs can induce responses from: T cells expressing CARs specific for a range of tumour antigens and from T cells expressing CARs comprising different antigens located in different positions within the CAR. T cells bearing a CAR for binding the tumour antigen CEA, and having a myc tag (CEA-myc CAR) secreted more IFN-γ (pg/mL; y-axis) when incubated with mouse splenocytes and a BEAT having a first binding domain for binding myc and a second binding domain for binding CD40. T cells bearing a CAR for binding the tumour antigen Her2, and having a—FLAG-tag located at the N terminus of the CAR (Her2-FLAG CAR) also secreted more IFN-γ when incubated with mouse splenocytes and a BEAT having a first binding domain for binding FLAG and a second binding domain for binding CD40. A BEAT specific for FLAG and CD40 also induced IFN-γ secretion from Her2-FLAG CAR T cells in the presence of CD40-expressing splenocytes.

The results shown in FIG. 21 demonstrate that CEA-myc CAR T cells secreted IFN-γ in the presence of BEAT1 when compared to the controls. Similarly, Her2-FLAG CAR T cells secreted IFN-γ in the presence of BEATS when compared to the controls.

These results demonstrate that BEATs have broad application in improving the efficacy of CAR T cell therapy. Firstly, BEATs have been demonstrated to induce responses from CAR T cells, wherein the CAR T cell is directed to different tumour associated antigens.

Secondly, BEATs have been demonstrated to induce responses from T cells when the CAR T cell is used in the context of cancers occurring in different tissue types.

The broad utility of BEATs is further demonstrated by the fact that it is possible to modify the design of BEATs in order to increase the efficacy of a variety of different CAR architectures in the context of CAR T therapy. For example, the results presented herein demonstrate that BEATs can be designed to bind to different antigens on a CAR and retain the ability to induce responses from CAR T cells. Thus, a variety of antigens within the CAR can be used as BEAT targets.

Importantly, it has also been demonstrated that the location of the antigen on the CAR can be varied without significantly affecting the efficacy of the BEAT. More specifically, a centrally located myc-tag (i.e., Her2-myc and CEA-myc CARs) and an N-terminally located FLAG epitope (i.e., Her2-FLAG CAR) proved to both be useful binding targets for BEATs. These data further demonstrate that antigens located at various positions within the CAR are effective for inducing CAR T cell responses.

CONCLUSION

The results presented herein demonstrate that BEATs can be designed and tailored to be used in conjunction with a wide range of different CAR architectures in order to increase the efficacy of CAR T therapy.

The bispecific polypeptides (i.e., BEATs) generated in this study have been demonstrated to be effective in activating and expanding CAR T cells through engagement of APCs. Further, BEATs have been demonstrated to be effective when targeting variety of tumour antigens and/or a variety of different antigens at different positions within the CAR. This approach is particularly advantageous over other methods of supporting T cell therapies as there is no restriction on MHC haplotype.

The pharmacokinetics of the BEATs advantageously enables a higher degree of control over CAR T cells by inducing activation and expansion "on demand", thereby balancing the requirements of anti-tumour efficacy while controlling toxicity against normal tissues, which has not been achieved with other methods of CAR T cell support, such as vaccines.

---

The invention claimed is:

1. A method of treating a solid tumor in a subject, the method comprising:
administering to a subject in need thereof:
(i) an immune cell expressing a chimeric antigen receptor (CAR) that binds to an antigen on the tumor; and
(ii) a bispecific polypeptide comprising a 1st binding domain and a 2nd binding domain, wherein the 1st binding domain specifically binds to an antigen expressed on an endogenous professional antigen presenting cell (APC) of the subject, wherein the endogenous professional APC is not a tumor cell; and wherein the 2nd binding domain specifically binds to an affinity tag on the CAR of the immune cell,
thereby treating the solid tumor in the subject,
wherein the antigen expressed on said endogenous professional antigen presenting cell is:
(i) not an antigen on the tumor;
(ii) not an antigen that is a tumor-associated antigen on the tumor; or
(iii) not differentially expressed by the tumor compared to a non-tumor cell of the same tissue type.

2. The method of claim 1, wherein the 1st binding domain binds to an antigen that is not overexpressed by the tumor compared to a non-tumor cell of the same tissue type.

3. The method of claim 1, wherein the 1st binding domain binds to an antigen on an endogenous professional APC that is expressed at a higher level by the APC than the antigen is expressed by the tumor.

4. The method of claim 1, wherein the immune cell is selected from the group consisting of a T cell, a NK cell, a cytotoxic T lymphocyte, a TIL and a regulatory T cell.

5. The method of claim 1, wherein the immune cell is a T cell.

6. The method of claim 1, wherein the immune cell is derived from an autologous cell.

7. The method of claim 1, wherein the immune cell is derived from an allogeneic cell.

8. The method of claim 1, wherein the bispecific polypeptide stimulates the activation and expansion of the immune cell in a MHC-haplotype independent manner.

9. The method of claim 1, wherein the endogenous professional APC of the subject is a dendritic cell or a macrophage.

10. The method of claim 1, wherein the endogenous professional APC of the subject is a dendritic cell.

11. The method of claim 1, wherein the affinity tag on the CAR is selected from a c-myc tag, FLAG-tag, HA-tag, His-tag, S-tag, SBP-tag, Strep-tag, eXACT-tag, GST-tag, MBP-tag or GFP-tag.

12. The method of claim 1, wherein the 1st binding domain binds to an antigen on the endogenous professional APC selected from: CD40, Clec9a, MHCII, PD-L1, PD-L2, galectin, CD11c, CD19 and CD83.

13. The method of claim 1, wherein the solid tumor is a breast tumor, a pancreatic tumor, colon tumor, or lung tumor.

14. A method of treating a solid tumor in a subject, the method comprising:
administering to a subject in need thereof:
(i) a CAR-T cell, wherein the CAR-T cells comprises a CAR that binds to an antigen on the tumor; and
(ii) a bispecific polypeptide comprising a 1st binding domain and a 2nd binding domain, wherein the 1st binding domain specifically binds to an antigen expressed on an endogenous professional antigen presenting cell (APC) of the subject; wherein the endogenous professional APC is a dendritic cell and is not a tumor cell; and wherein the 2nd binding domain specifically binds to an affinity tag on the CAR of the immune cell,
thereby treating the solid tumor in the subject,
wherein the antigen expressed on said endogenous professional antigen presenting cell is:
(i) not an antigen on the tumor;
(ii) not an antigen that is a tumor-associated antigen on the tumor; or
(iii) not differentially expressed by the tumor compared to a non-tumor cell of the same tissue type.

15. The method of claim 14, wherein the 1st binding domain binds to an antigen that is not a tumor-associated antigen on the tumor cell.

16. The method of claim 14, wherein the 1st binding domain binds to an antigen that is not overexpressed by the tumor cell compared to a non-tumor cell of the same tissue type or is not differentially expressed by the tumor compared to a non-tumor cell of the same tissue type.

* * * * *

SEQUENCE LISTING

```
<160> NUMBER OF SEQ ID NOS: 26

<210> SEQ ID NO 1
<211> LENGTH: 747
<212> TYPE: DNA
<213> ORGANISM: Artificial Sequence
<220> FEATURE:
<223> OTHER INFORMATION: Anti-CD40 scFv
<220> FEATURE:
<221> NAME/KEY: CDS
<222> LOCATION: (1)..(747)

<400> SEQUENCE: 1 atg gag gtg cag gtg gtg gag tct gat gga ggc tta gtg cag cct gga        48
Met Glu Val Gln Val Val Glu Ser Asp Gly Gly Leu Val Gln Pro Gly
1               5                   10                  15 agg tcc cta aaa ctc ccc tgt gca gcc tca gga ttc act ttc agt gac        96
Arg Ser Leu Lys Leu Pro Cys Ala Ala Ser Gly Phe Thr Phe Ser Asp
            20                  25                  30 tat tac atg gcc tgg gtc cgc cag gct cca acg aag ggg ctg gag tgg       144
Tyr Tyr Met Ala Trp Val Arg Gln Ala Pro Thr Lys Gly Leu Glu Trp
        35                  40                  45 gtc gca agc att agt tat gat ggt agt agc act tac tat cga gac tcc       192
Val Ala Ser Ile Ser Tyr Asp Gly Ser Ser Thr Tyr Tyr Arg Asp Ser
    50                  55                  60 gtg aag ggc cga ttc act atc tcc aga gat aat gca aaa agc acc cta       240
Val Lys Gly Arg Phe Thr Ile Ser Arg Asp Asn Ala Lys Ser Thr Leu
65                  70                  75                  80 tac ctg caa atg gac agt ctg agg tct gag gac acg gcc act tat tac       288
Tyr Leu Gln Met Asp Ser Leu Arg Ser Glu Asp Thr Ala Thr Tyr Tyr
                85                  90                  95 tgc gga aga cac agt agc tac ttt gat tac tgg ggc caa gga gtc atg       336
Cys Gly Arg His Ser Ser Tyr Phe Asp Tyr Trp Gly Gln Gly Val Met
            100                 105                 110 gtc aca gtc tcc tca ggt gga ggc ggt tca ggc gga ggt ggc tct ggc       384
Val Thr Val Ser Ser Gly Gly Gly Gly Ser Gly Gly Gly Gly Ser Gly
        115                 120                 125 ggt ggc gga tcg gac act gta ctg acc cag tct cct gct ttg gct gtg       432
Gly Gly Gly Ser Asp Thr Val Leu Thr Gln Ser Pro Ala Leu Ala Val
    130                 135                 140
```

-continued

```
tct cca gga gag agg gtt acc atc tcc tgt agg gcc agt gac agt gtc    480
Ser Pro Gly Glu Arg Val Thr Ile Ser Cys Arg Ala Ser Asp Ser Val
145                 150                 155                 160 agt aca ctt atg cac tgg tac caa cag aaa cca gga cag caa ccc aaa    528
Ser Thr Leu Met His Trp Tyr Gln Gln Lys Pro Gly Gln Gln Pro Lys
                165                 170                 175 ctc ctc atc tat cta gca tca cac cta gaa tct ggg gtc cct gcc agg    576
Leu Leu Ile Tyr Leu Ala Ser His Leu Glu Ser Gly Val Pro Ala Arg
            180                 185                 190 ttc agt ggc agt ggg tct ggg aca gac ttc acc ctc acc att gat cct    624
Phe Ser Gly Ser Gly Ser Gly Thr Asp Phe Thr Leu Thr Ile Asp Pro
        195                 200                 205 gtg gag gct gat gac act gca acc tat tac tgt cag cag agt tgg aat    672
Val Glu Ala Asp Asp Thr Ala Thr Tyr Tyr Cys Gln Gln Ser Trp Asn
    210                 215                 220 gat ccg tgg acg ttc ggt gga ggc acc aag ctg gaa ttg aaa aat ggg    720
Asp Pro Trp Thr Phe Gly Gly Gly Thr Lys Leu Glu Leu Lys Asn Gly
225                 230                 235                 240 gcc gtc gag cac cac cac cac cac cac                                747
Ala Val Glu His His His His His His
                245
```

<210> SEQ ID NO 2
<211> LENGTH: 249
<212> TYPE: PRT
<213> ORGANISM: Artificial Sequence
<220> FEATURE:
<223> OTHER INFORMATION: Synthetic Construct

<400> SEQUENCE: 2

```
Met Glu Val Gln Val Val Glu Ser Asp Gly Gly Leu Val Gln Pro Gly
1               5                   10                  15

Arg Ser Leu Lys Leu Pro Cys Ala Ala Ser Gly Phe Thr Phe Ser Asp
            20                  25                  30

Tyr Tyr Met Ala Trp Val Arg Gln Ala Pro Thr Lys Gly Leu Glu Trp
        35                  40                  45

Val Ala Ser Ile Ser Tyr Asp Gly Ser Ser Thr Tyr Tyr Arg Asp Ser
    50                  55                  60

Val Lys Gly Arg Phe Thr Ile Ser Arg Asp Asn Ala Lys Ser Thr Leu
65                  70                  75                  80

Tyr Leu Gln Met Asp Ser Leu Arg Ser Glu Asp Thr Ala Thr Tyr Tyr
                85                  90                  95

Cys Gly Arg His Ser Ser Tyr Phe Asp Tyr Trp Gly Gln Gly Val Met
            100                 105                 110

Val Thr Val Ser Ser Gly Gly Gly Gly Ser Gly Gly Gly Gly Ser Gly
        115                 120                 125

Gly Gly Gly Ser Asp Thr Val Leu Thr Gln Ser Pro Ala Leu Ala Val
    130                 135                 140

Ser Pro Gly Glu Arg Val Thr Ile Ser Cys Arg Ala Ser Asp Ser Val
145                 150                 155                 160

Ser Thr Leu Met His Trp Tyr Gln Gln Lys Pro Gly Gln Gln Pro Lys
                165                 170                 175

Leu Leu Ile Tyr Leu Ala Ser His Leu Glu Ser Gly Val Pro Ala Arg
            180                 185                 190

Phe Ser Gly Ser Gly Ser Gly Thr Asp Phe Thr Leu Thr Ile Asp Pro
        195                 200                 205

Val Glu Ala Asp Asp Thr Ala Thr Tyr Tyr Cys Gln Gln Ser Trp Asn
    210                 215                 220
```

```
Asp Pro Trp Thr Phe Gly Gly Gly Thr Lys Leu Glu Leu Lys Asn Gly
225                 230                 235                 240

Ala Val Glu His His His His His His
                245
```

<210> SEQ ID NO 3
<211> LENGTH: 621
<212> TYPE: DNA
<213> ORGANISM: Artificial Sequence
<220> FEATURE:
<223> OTHER INFORMATION: Anti-MHCII scFv
<220> FEATURE:
<221> NAME/KEY: CDS
<222> LOCATION: (1)..(621)

<400> SEQUENCE: 3

```
gag gtg cag ctt cag gag tca gga cct ggc ctt gtg aaa ccc tca cag      48
Glu Val Gln Leu Gln Glu Ser Gly Pro Gly Leu Val Lys Pro Ser Gln
1               5                   10                  15 tca ctc tcc ctc acc tgt tct gtc act gct tac ttc atc act agt aat      96
Ser Leu Ser Leu Thr Cys Ser Val Thr Ala Tyr Phe Ile Thr Ser Asn
            20                  25                  30 tac tgg gcc tgg atc cgg aag ttc cca gga aat aaa atg gag tgg atg     144
Tyr Trp Ala Trp Ile Arg Lys Phe Pro Gly Asn Lys Met Glu Trp Met
        35                  40                  45 gga cac ata acc tac agt ggt tac act acc tac aat cca tct ctc aaa     192
Gly His Ile Thr Tyr Ser Gly Tyr Thr Thr Tyr Asn Pro Ser Leu Lys
    50                  55                  60 agt cga atc tcc att act aga gac aca tcg agg aat cag ttc ttc ctc     240
Ser Arg Ile Ser Ile Thr Arg Asp Thr Ser Arg Asn Gln Phe Phe Leu
65                  70                  75                  80 cag ttg aac tct gta act act gag gac aca gcc act tat tac tgt gca     288
Gln Leu Asn Ser Val Thr Thr Glu Asp Thr Ala Thr Tyr Tyr Cys Ala
                85                  90                  95 aga ggt gga ggc ggt tca ggc gga ggt ggc tct ggc ggt ggc gga tcg     336
Arg Gly Gly Gly Gly Ser Gly Gly Gly Ser Gly Gly Gly Gly Ser
            100                 105                 110 aac att gta atg acc caa tct ccc aaa tcc atg tcc atg tca gta gga     384
Asn Ile Val Met Thr Gln Ser Pro Lys Ser Met Ser Met Ser Val Gly
        115                 120                 125 gag agg gtc acc ttg acc tgc aag gcc agt gag aat gtg gtt act tat     432
Glu Arg Val Thr Leu Thr Cys Lys Ala Ser Glu Asn Val Val Thr Tyr
    130                 135                 140 gtt tcc tgg tat caa cag aaa cca gag cag tct cct aaa ctg ctg ata     480
Val Ser Trp Tyr Gln Gln Lys Pro Glu Gln Ser Pro Lys Leu Leu Ile
145                 150                 155                 160 tac ggg gca tcc aac cgg tac act ggg gtc ccc gat cgc ttc aca ggc     528
Tyr Gly Ala Ser Asn Arg Tyr Thr Gly Val Pro Asp Arg Phe Thr Gly
                165                 170                 175 agt gga tct gca aca gat ttc act ctg acc atc agc agt gtg cag gct     576
Ser Gly Ser Ala Thr Asp Phe Thr Leu Thr Ile Ser Ser Val Gln Ala
            180                 185                 190 gaa gac ctt gca gat tat cac tgt gga cag ggt tac agc tat ccg         621
Glu Asp Leu Ala Asp Tyr His Cys Gly Gln Gly Tyr Ser Tyr Pro
        195                 200                 205
```

<210> SEQ ID NO 4
<211> LENGTH: 207
<212> TYPE: PRT
<213> ORGANISM: Artificial Sequence
<220> FEATURE:
<223> OTHER INFORMATION: Synthetic Construct

<400> SEQUENCE: 4

```
Glu Val Gln Leu Gln Glu Ser Gly Pro Gly Leu Val Lys Pro Ser Gln
1               5                   10                  15

Ser Leu Ser Leu Thr Cys Ser Val Thr Ala Tyr Phe Ile Thr Ser Asn
            20                  25                  30

Tyr Trp Ala Trp Ile Arg Lys Phe Pro Gly Asn Lys Met Glu Trp Met
        35                  40                  45

Gly His Ile Thr Tyr Ser Gly Tyr Thr Thr Tyr Asn Pro Ser Leu Lys
    50                  55                  60

Ser Arg Ile Ser Ile Thr Arg Asp Thr Ser Arg Asn Gln Phe Phe Leu
65                  70                  75                  80

Gln Leu Asn Ser Val Thr Thr Glu Asp Thr Ala Thr Tyr Tyr Cys Ala
                85                  90                  95

Arg Gly Gly Gly Gly Ser Gly Gly Gly Ser Gly Gly Gly Gly Ser
            100                 105                 110

Asn Ile Val Met Thr Gln Ser Pro Lys Ser Met Ser Met Ser Val Gly
            115                 120                 125

Glu Arg Val Thr Leu Thr Cys Lys Ala Ser Glu Asn Val Val Thr Tyr
130                 135                 140

Val Ser Trp Tyr Gln Gln Lys Pro Glu Gln Ser Pro Lys Leu Leu Ile
145                 150                 155                 160

Tyr Gly Ala Ser Asn Arg Tyr Thr Gly Val Pro Asp Arg Phe Thr Gly
                165                 170                 175

Ser Gly Ser Ala Thr Asp Phe Thr Leu Thr Ile Ser Ser Val Gln Ala
            180                 185                 190

Glu Asp Leu Ala Asp Tyr His Cys Gly Gln Gly Tyr Ser Tyr Pro
        195                 200                 205
```

<210> SEQ ID NO 5
<211> LENGTH: 777
<212> TYPE: DNA
<213> ORGANISM: Artificial Sequence
<220> FEATURE:
<223> OTHER INFORMATION: Anti-CD3 2C11 scFv
<220> FEATURE:
<221> NAME/KEY: CDS
<222> LOCATION: (1)..(777)

<400> SEQUENCE: 5

```
atg gag aca gac aca ctc ctg cta tgg gta ctg ctg ctc tgg gtt cca      48
Met Glu Thr Asp Thr Leu Leu Leu Trp Val Leu Leu Leu Trp Val Pro
1               5                   10                  15 ggt tcc act ggt gac gag gtg cag ctg gtg gag tct ggg gga ggc ttg      96
Gly Ser Thr Gly Asp Glu Val Gln Leu Val Glu Ser Gly Gly Gly Leu
            20                  25                  30 gtg cag cct gga aag tcc ctg aaa ctc tcc tgt gag gcc tct gga ttc     144
Val Gln Pro Gly Lys Ser Leu Lys Leu Ser Cys Glu Ala Ser Gly Phe
        35                  40                  45 acc ttc agc ggc tat ggc atg cac tgg gtc cgc cag gct cca ggg agg     192
Thr Phe Ser Gly Tyr Gly Met His Trp Val Arg Gln Ala Pro Gly Arg
    50                  55                  60 ggg ctg gag tcg gtc gca tac att act agt agt agt att aat atc aaa     240
Gly Leu Glu Ser Val Ala Tyr Ile Thr Ser Ser Ser Ile Asn Ile Lys
65                  70                  75                  80 tat gct gac gct gtg aaa ggc cgg ttc acc gtc tcc aga gac aat gcc     288
Tyr Ala Asp Ala Val Lys Gly Arg Phe Thr Val Ser Arg Asp Asn Ala
                85                  90                  95
```

|  |  |
|---|---|
| aag aac tta ctg ttt cta caa atg aac att ctc aag tct gag gac aca<br>Lys Asn Leu Leu Phe Leu Gln Met Asn Ile Leu Lys Ser Glu Asp Thr<br>            100                 105                 110 | 336 |
| gcc atg tac tac tgt gca aga ttc gac tgg gac aaa aat tac tgg ggc<br>Ala Met Tyr Tyr Cys Ala Arg Phe Asp Trp Asp Lys Asn Tyr Trp Gly<br>        115                 120                 125 | 384 |
| caa gga acc atg gtc acc gtc tcc tca ggt gga ggc ggt tca ggc gga<br>Gln Gly Thr Met Val Thr Val Ser Ser Gly Gly Gly Gly Ser Gly Gly<br>    130                 135                 140 | 432 |
| ggt ggc tct ggc ggt ggc gga tcg gac atc cag atg acc cag tct cca<br>Gly Gly Ser Gly Gly Gly Gly Ser Asp Ile Gln Met Thr Gln Ser Pro<br>145                 150                 155                 160 | 480 |
| tca tca ctg cct gcc tcc ctg gga gac aga gtc act atc aat tgt cag<br>Ser Ser Leu Pro Ala Ser Leu Gly Asp Arg Val Thr Ile Asn Cys Gln<br>                165                 170                 175 | 528 |
| gcc agt cag gac att agc aat tat tta aac tgg tac cag cag aaa cca<br>Ala Ser Gln Asp Ile Ser Asn Tyr Leu Asn Trp Tyr Gln Gln Lys Pro<br>            180                 185                 190 | 576 |
| ggg aaa gct cct aag ctc ctg atc tat tat aca aat aaa ttg gca gat<br>Gly Lys Ala Pro Lys Leu Leu Ile Tyr Tyr Thr Asn Lys Leu Ala Asp<br>        195                 200                 205 | 624 |
| gga gtc cca tca agg ttc agt ggc agt ggt tct ggg aga gat tct tct<br>Gly Val Pro Ser Arg Phe Ser Gly Ser Gly Ser Gly Arg Asp Ser Ser<br>    210                 215                 220 | 672 |
| ttc act atc agc agc ctg gaa tcc gaa gat att gga tct tat tac tgt<br>Phe Thr Ile Ser Ser Leu Glu Ser Glu Asp Ile Gly Ser Tyr Tyr Cys<br>225                 230                 235                 240 | 720 |
| caa cag tat tat aac tat ccg tgg acg ttc gga cct ggc acc aag ctg<br>Gln Gln Tyr Tyr Asn Tyr Pro Trp Thr Phe Gly Pro Gly Thr Lys Leu<br>                245                 250                 255 | 768 |
| gaa atc aaa<br>Glu Ile Lys | 777 |

<210> SEQ ID NO 6
<211> LENGTH: 259
<212> TYPE: PRT
<213> ORGANISM: Artificial Sequence
<220> FEATURE:
<223> OTHER INFORMATION: Synthetic Construct

<400> SEQUENCE: 6

Met Glu Thr Asp Thr Leu Leu Leu Trp Val Leu Leu Leu Trp Val Pro
1               5                   10                  15

Gly Ser Thr Gly Asp Glu Val Gln Leu Val Glu Ser Gly Gly Gly Leu
            20                  25                  30

Val Gln Pro Gly Lys Ser Leu Lys Leu Ser Cys Glu Ala Ser Gly Phe
        35                  40                  45

Thr Phe Ser Gly Tyr Gly Met His Trp Val Arg Gln Ala Pro Gly Arg
    50                  55                  60

Gly Leu Glu Ser Val Ala Tyr Ile Thr Ser Ser Ser Ile Asn Ile Lys
65                  70                  75                  80

Tyr Ala Asp Ala Val Lys Gly Arg Phe Thr Val Ser Arg Asp Asn Ala
                85                  90                  95

Lys Asn Leu Leu Phe Leu Gln Met Asn Ile Leu Lys Ser Glu Asp Thr
            100                 105                 110

Ala Met Tyr Tyr Cys Ala Arg Phe Asp Trp Asp Lys Asn Tyr Trp Gly
        115                 120                 125

Gln Gly Thr Met Val Thr Val Ser Ser Gly Gly Gly Gly Ser Gly Gly
    130                 135                 140

```
Gly Gly Ser Gly Gly Gly Ser Asp Ile Gln Met Thr Gln Ser Pro
145                 150                 155                 160

Ser Ser Leu Pro Ala Ser Leu Gly Asp Arg Val Thr Ile Asn Cys Gln
            165                 170                 175

Ala Ser Gln Asp Ile Ser Asn Tyr Leu Asn Trp Tyr Gln Lys Pro
        180                 185                 190

Gly Lys Ala Pro Lys Leu Leu Ile Tyr Tyr Thr Asn Lys Leu Ala Asp
        195                 200                 205

Gly Val Pro Ser Arg Phe Ser Gly Ser Gly Arg Asp Ser Ser
        210                 215                 220

Phe Thr Ile Ser Ser Leu Glu Ser Glu Asp Ile Gly Ser Tyr Tyr Cys
225                 230                 235                 240

Gln Gln Tyr Tyr Asn Tyr Pro Trp Thr Phe Gly Pro Gly Thr Lys Leu
            245                 250                 255

Glu Ile Lys
```

<210> SEQ ID NO 7
<211> LENGTH: 762
<212> TYPE: DNA
<213> ORGANISM: Artificial Sequence
<220> FEATURE:
<223> OTHER INFORMATION: Anti-c-myc scFv
<220> FEATURE:
<221> NAME/KEY: CDS
<222> LOCATION: (1)..(762)

<400> SEQUENCE: 7

```
atg gag gtg cac ctg gtg gag tct ggg gga gac tta gtg aag cct gga     48
Met Glu Val His Leu Val Glu Ser Gly Gly Asp Leu Val Lys Pro Gly
1               5                   10                  15 ggg tcc ctg aaa ctc tcc tgt gca gcc tct gga ttc act ttc agt cac     96
Gly Ser Leu Lys Leu Ser Cys Ala Ala Ser Gly Phe Thr Phe Ser His
                20                  25                  30 tat ggc atg tct tgg gtt cgc cag act cca gac aag agg ctg gag tgg    144
Tyr Gly Met Ser Trp Val Arg Gln Thr Pro Asp Lys Arg Leu Glu Trp
            35                  40                  45 gtc gca acc att ggt agt cgt ggt act tac acc cac tat cca gac agt    192
Val Ala Thr Ile Gly Ser Arg Gly Thr Tyr Thr His Tyr Pro Asp Ser
        50                  55                  60 gtg aag gga cga ttc acc atc tcc aga gac aat gac aag aac gcc ctg    240
Val Lys Gly Arg Phe Thr Ile Ser Arg Asp Asn Asp Lys Asn Ala Leu
65                  70                  75                  80 tac ctg caa atg aac agt ctg aag tct gaa gac aca gcc atg tat tac    288
Tyr Leu Gln Met Asn Ser Leu Lys Ser Glu Asp Thr Ala Met Tyr Tyr
                85                  90                  95 tgt gca aga aga agt gaa ttt tat tac tac ggt aat acc tac tat tac    336
Cys Ala Arg Arg Ser Glu Phe Tyr Tyr Tyr Gly Asn Thr Tyr Tyr Tyr
            100                 105                 110 tct gct atg gac tac tgg ggt caa gga gcc tca gtc acc gtc tcc tca    384
Ser Ala Met Asp Tyr Trp Gly Gln Gly Ala Ser Val Thr Val Ser Ser
        115                 120                 125 ggt gga ggc ggt tca ggc gga ggt ggc tct ggc ggt ggc gga tcg gac    432
Gly Gly Gly Gly Ser Gly Gly Gly Ser Gly Gly Gly Gly Ser Asp
        130                 135                 140 att gtg ctg acc caa tct cca gct tct ttg gct gta tct cta gga cag    480
Ile Val Leu Thr Gln Ser Pro Ala Ser Leu Ala Val Ser Leu Gly Gln
145                 150                 155                 160 agg gcc acc atc tcc tgc aga gcc agc gaa agt gtt gat aat tat ggc    528
Arg Ala Thr Ile Ser Cys Arg Ala Ser Glu Ser Val Asp Asn Tyr Gly
```

```
                   165                 170                 175
ttt agt ttt atg aac tgg ttc caa cag aaa cca gga cag cca ccc aaa      576
Phe Ser Phe Met Asn Trp Phe Gln Gln Lys Pro Gly Gln Pro Pro Lys
            180                 185                 190 ctc ctc atc tat gct ata tcc aac cga gga tcc ggg gtc cct gcc agg      624
Leu Leu Ile Tyr Ala Ile Ser Asn Arg Gly Ser Gly Val Pro Ala Arg
        195                 200                 205 ttt agt ggc agt ggg tct ggg aca gac ttc agc ctc aac atc cat cct      672
Phe Ser Gly Ser Gly Ser Gly Thr Asp Phe Ser Leu Asn Ile His Pro
    210                 215                 220 gta gag gag gat gat cct gca atg tat ttc tgt cag caa act aag gag      720
Val Glu Glu Asp Asp Pro Ala Met Tyr Phe Cys Gln Gln Thr Lys Glu
225                 230                 235                 240 gtt ccg tgg acg ttc ggt gga ggc acc aag ctg gaa atc aaa              762
Val Pro Trp Thr Phe Gly Gly Gly Thr Lys Leu Glu Ile Lys
                245                 250

<210> SEQ ID NO 8
<211> LENGTH: 254
<212> TYPE: PRT
<213> ORGANISM: Artificial Sequence
<220> FEATURE:
<223> OTHER INFORMATION: Synthetic Construct

<400> SEQUENCE: 8

Met Glu Val His Leu Val Glu Ser Gly Gly Asp Leu Val Lys Pro Gly
1               5                   10                  15

Gly Ser Leu Lys Leu Ser Cys Ala Ala Ser Gly Phe Thr Phe Ser His
            20                  25                  30

Tyr Gly Met Ser Trp Val Arg Gln Thr Pro Asp Lys Arg Leu Glu Trp
        35                  40                  45

Val Ala Thr Ile Gly Ser Arg Gly Thr Tyr Thr His Tyr Pro Asp Ser
    50                  55                  60

Val Lys Gly Arg Phe Thr Ile Ser Arg Asp Asn Asp Lys Asn Ala Leu
65                  70                  75                  80

Tyr Leu Gln Met Asn Ser Leu Lys Ser Glu Asp Thr Ala Met Tyr Tyr
                85                  90                  95

Cys Ala Arg Arg Ser Glu Phe Tyr Tyr Tyr Gly Asn Thr Tyr Tyr Tyr
            100                 105                 110

Ser Ala Met Asp Tyr Trp Gly Gln Gly Ala Ser Val Thr Val Ser Ser
        115                 120                 125

Gly Gly Gly Gly Ser Gly Gly Gly Ser Gly Gly Gly Gly Ser Asp
    130                 135                 140

Ile Val Leu Thr Gln Ser Pro Ala Ser Leu Ala Val Ser Leu Gly Gln
145                 150                 155                 160

Arg Ala Thr Ile Ser Cys Arg Ala Ser Glu Ser Val Asp Asn Tyr Gly
                165                 170                 175

Phe Ser Phe Met Asn Trp Phe Gln Gln Lys Pro Gly Gln Pro Pro Lys
            180                 185                 190

Leu Leu Ile Tyr Ala Ile Ser Asn Arg Gly Ser Gly Val Pro Ala Arg
        195                 200                 205

Phe Ser Gly Ser Gly Ser Gly Thr Asp Phe Ser Leu Asn Ile His Pro
    210                 215                 220

Val Glu Glu Asp Asp Pro Ala Met Tyr Phe Cys Gln Gln Thr Lys Glu
225                 230                 235                 240

Val Pro Trp Thr Phe Gly Gly Gly Thr Lys Leu Glu Ile Lys
                245                 250
```

<210> SEQ ID NO 9
<211> LENGTH: 15
<212> TYPE: DNA
<213> ORGANISM: Artificial Sequence
<220> FEATURE:
<223> OTHER INFORMATION: Linker 1
<220> FEATURE:
<221> NAME/KEY: CDS
<222> LOCATION: (1)..(15)

<400> SEQUENCE: 9

```
ggt gga ggc ggt tca                                              15
Gly Gly Gly Gly Ser
1               5
```

<210> SEQ ID NO 10
<211> LENGTH: 5
<212> TYPE: PRT
<213> ORGANISM: Artificial Sequence
<220> FEATURE:
<223> OTHER INFORMATION: Synthetic Construct

<400> SEQUENCE: 10

```
Gly Gly Gly Gly Ser
1               5
```

<210> SEQ ID NO 11
<211> LENGTH: 45
<212> TYPE: DNA
<213> ORGANISM: Artificial Sequence
<220> FEATURE:
<223> OTHER INFORMATION: Linker 2
<220> FEATURE:
<221> NAME/KEY: CDS
<222> LOCATION: (1)..(45)

<400> SEQUENCE: 11

```
ggt gga ggc ggt tca ggc gga ggt ggc tct ggc ggt ggc gga tcg      45
Gly Gly Gly Gly Ser Gly Gly Gly Gly Ser Gly Gly Gly Gly Ser
1               5                  10                  15
```

<210> SEQ ID NO 12
<211> LENGTH: 15
<212> TYPE: PRT
<213> ORGANISM: Artificial Sequence
<220> FEATURE:
<223> OTHER INFORMATION: Synthetic Construct

<400> SEQUENCE: 12

```
Gly Gly Gly Gly Ser Gly Gly Gly Gly Ser Gly Gly Gly Gly Ser
1               5                  10                  15
```

<210> SEQ ID NO 13
<211> LENGTH: 90
<212> TYPE: DNA
<213> ORGANISM: Artificial Sequence
<220> FEATURE:
<223> OTHER INFORMATION: Linker 3
<220> FEATURE:
<221> NAME/KEY: CDS
<222> LOCATION: (1)..(90)

<400> SEQUENCE: 13

```
ggt gga ggc ggt tca ggc gga ggt ggc tct ggc ggt ggc gga tcg ggt  48
Gly Gly Gly Gly Ser Gly Gly Gly Gly Ser Gly Gly Gly Gly Ser Gly
1               5                  10                  15 gga ggc ggt tca ggc gga ggt ggc tct ggc ggt ggc gga tcg           90
```

```
Gly Gly Gly Ser Gly Gly Gly Ser Gly Gly Gly Ser
            20              25              30

<210> SEQ ID NO 14
<211> LENGTH: 30
<212> TYPE: PRT
<213> ORGANISM: Artificial Sequence
<220> FEATURE:
<223> OTHER INFORMATION: Synthetic Construct

<400> SEQUENCE: 14

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser
            20              25              30

<210> SEQ ID NO 15
<211> LENGTH: 1524
<212> TYPE: DNA
<213> ORGANISM: Artificial Sequence
<220> FEATURE:
<223> OTHER INFORMATION: BEAT 1 CD40/c-myc-tag
<220> FEATURE:
<221> NAME/KEY: CDS
<222> LOCATION: (1)..(1524)

<400> SEQUENCE: 15 atg gag gtg cac ctg gtg gag tct ggg gga gac tta gtg aag cct gga         48
Met Glu Val His Leu Val Glu Ser Gly Gly Asp Leu Val Lys Pro Gly
1               5                   10                  15 ggg tcc ctg aaa ctc tcc tgt gca gcc tct gga ttc act ttc agt cac         96
Gly Ser Leu Lys Leu Ser Cys Ala Ala Ser Gly Phe Thr Phe Ser His
            20                  25                  30 tat ggc atg tct tgg gtt cgc cag act cca gac aag agg ctg gag tgg        144
Tyr Gly Met Ser Trp Val Arg Gln Thr Pro Asp Lys Arg Leu Glu Trp
        35                  40                  45 gtc gca acc att ggt agt cgt ggt act tac acc cac tat cca gac agt        192
Val Ala Thr Ile Gly Ser Arg Gly Thr Tyr Thr His Tyr Pro Asp Ser
    50                  55                  60 gtg aag gga cga ttc acc atc tcc aga gac aat gac aag aac gcc ctg        240
Val Lys Gly Arg Phe Thr Ile Ser Arg Asp Asn Asp Lys Asn Ala Leu
65                  70                  75                  80 tac ctg caa atg aac agt ctg aag tct gaa gac aca gcc atg tat tac        288
Tyr Leu Gln Met Asn Ser Leu Lys Ser Glu Asp Thr Ala Met Tyr Tyr
                85                  90                  95 tgt gca aga aga agt gaa ttt tat tac tac ggt aat acc tac tat tac        336
Cys Ala Arg Arg Ser Glu Phe Tyr Tyr Tyr Gly Asn Thr Tyr Tyr Tyr
            100                 105                 110 tct gct atg gac tac tgg ggt caa gga gcc tca gtc acc gtc tcc tca        384
Ser Ala Met Asp Tyr Trp Gly Gln Gly Ala Ser Val Thr Val Ser Ser
        115                 120                 125 ggt gga ggc ggt tca ggc gga ggt ggc tct ggc ggt ggc gga tcg gac        432
Gly Gly Gly Gly Ser Gly Gly Gly Gly Ser Gly Gly Gly Gly Ser Asp
    130                 135                 140 att gtg ctg acc caa tct cca gct tct ttg gct gta tct cta gga cag        480
Ile Val Leu Thr Gln Ser Pro Ala Ser Leu Ala Val Ser Leu Gly Gln
145                 150                 155                 160 agg gcc acc atc tcc tgc aga gcc agc gaa agt gtt gat aat tat ggc        528
Arg Ala Thr Ile Ser Cys Arg Ala Ser Glu Ser Val Asp Asn Tyr Gly
                165                 170                 175 ttt agt ttt atg aac tgg ttc caa cag aaa cca gga cag cca ccc aaa        576
Phe Ser Phe Met Asn Trp Phe Gln Gln Lys Pro Gly Gln Pro Pro Lys
            180                 185                 190
```

| | | |
|---|---|---|
| ctc ctc atc tat gct ata tcc aac cga gga tcc ggg gtc cct gcc agg<br>Leu Leu Ile Tyr Ala Ile Ser Asn Arg Gly Ser Gly Val Pro Ala Arg<br>195 200 205 | | 624 |
| ttt agt ggc agt ggg tct ggg aca gac ttc agc ctc aac atc cat cct<br>Phe Ser Gly Ser Gly Ser Gly Thr Asp Phe Ser Leu Asn Ile His Pro<br>210 215 220 | | 672 |
| gta gag gag gat gat cct gca atg tat ttc tgt cag caa act aag gag<br>Val Glu Glu Asp Asp Pro Ala Met Tyr Phe Cys Gln Gln Thr Lys Glu<br>225 230 235 240 | | 720 |
| gtt ccg tgg acg ttc ggt gga ggc acc aag ctg gaa atc aaa ggt gga<br>Val Pro Trp Thr Phe Gly Gly Gly Thr Lys Leu Glu Ile Lys Gly Gly<br>245 250 255 | | 768 |
| ggc ggt tca atg gag gtg cag gtg gtg gag tct gat gga ggc tta gtg<br>Gly Gly Ser Met Glu Val Gln Val Val Glu Ser Asp Gly Gly Leu Val<br>260 265 270 | | 816 |
| cag cct gga agg tcc cta aaa ctc ccc tgt gca gcc tca gga ttc act<br>Gln Pro Gly Arg Ser Leu Lys Leu Pro Cys Ala Ala Ser Gly Phe Thr<br>275 280 285 | | 864 |
| ttc agt gac tat tac atg gcc tgg gtc cgc cag gct cca acg aag ggg<br>Phe Ser Asp Tyr Tyr Met Ala Trp Val Arg Gln Ala Pro Thr Lys Gly<br>290 295 300 | | 912 |
| ctg gag tgg gtc gca agc att agt tat gat ggt agt agc act tac tat<br>Leu Glu Trp Val Ala Ser Ile Ser Tyr Asp Gly Ser Ser Thr Tyr Tyr<br>305 310 315 320 | | 960 |
| cga gac tcc gtg aag ggc cga ttc act atc tcc aga gat aat gca aaa<br>Arg Asp Ser Val Lys Gly Arg Phe Thr Ile Ser Arg Asp Asn Ala Lys<br>325 330 335 | | 1008 |
| agc acc cta tac ctg caa atg gac agt ctg agg tct gag gac acg gcc<br>Ser Thr Leu Tyr Leu Gln Met Asp Ser Leu Arg Ser Glu Asp Thr Ala<br>340 345 350 | | 1056 |
| act tat tac tgc gga aga cac agt agc tac ttt gat tac tgg ggc caa<br>Thr Tyr Tyr Cys Gly Arg His Ser Ser Tyr Phe Asp Tyr Trp Gly Gln<br>355 360 365 | | 1104 |
| gga gtc atg gtc aca gtc tcc tca ggt gga ggc ggt tca ggc gga ggt<br>Gly Val Met Val Thr Val Ser Ser Gly Gly Gly Gly Ser Gly Gly Gly<br>370 375 380 | | 1152 |
| ggc tct ggc ggt ggc gga tcg gac act gta ctg acc cag tct cct gct<br>Gly Ser Gly Gly Gly Gly Ser Asp Thr Val Leu Thr Gln Ser Pro Ala<br>385 390 395 400 | | 1200 |
| ttg gct gtg tct cca gga gag agg gtt acc atc tcc tgt agg gcc agt<br>Leu Ala Val Ser Pro Gly Glu Arg Val Thr Ile Ser Cys Arg Ala Ser<br>405 410 415 | | 1248 |
| gac agt gtc agt aca ctt atg cac tgg tac caa cag aaa cca gga cag<br>Asp Ser Val Ser Thr Leu Met His Trp Tyr Gln Gln Lys Pro Gly Gln<br>420 425 430 | | 1296 |
| caa ccc aaa ctc ctc atc tat cta gca tca cac cta gaa tct ggg gtc<br>Gln Pro Lys Leu Leu Ile Tyr Leu Ala Ser His Leu Glu Ser Gly Val<br>435 440 445 | | 1344 |
| cct gcc agg ttc agt ggc agt ggg tct ggg aca gac ttc acc ctc acc<br>Pro Ala Arg Phe Ser Gly Ser Gly Ser Gly Thr Asp Phe Thr Leu Thr<br>450 455 460 | | 1392 |
| att gat cct gtg gag gct gat gac act gca acc tat tac tgt cag cag<br>Ile Asp Pro Val Glu Ala Asp Asp Thr Ala Thr Tyr Tyr Cys Gln Gln<br>465 470 475 480 | | 1440 |
| agt tgg aat gat ccg tgg acg ttc ggt gga ggc acc aag ctg gaa ttg<br>Ser Trp Asn Asp Pro Trp Thr Phe Gly Gly Gly Thr Lys Leu Glu Leu<br>485 490 495 | | 1488 |
| aaa aat ggg gcc gtc gag cac cac cac cac cac cac<br>Lys Asn Gly Ala Val Glu His His His His His His | | 1524 |

<210> SEQ ID NO 16
<211> LENGTH: 508
<212> TYPE: PRT
<213> ORGANISM: Artificial Sequence
<220> FEATURE:
<223> OTHER INFORMATION: Synthetic Construct

<400> SEQUENCE: 16

```
Met Glu Val His Leu Val Glu Ser Gly Gly Asp Leu Val Lys Pro Gly
1               5                   10                  15

Gly Ser Leu Lys Leu Ser Cys Ala Ala Ser Gly Phe Thr Phe Ser His
            20                  25                  30

Tyr Gly Met Ser Trp Val Arg Gln Thr Pro Asp Lys Arg Leu Glu Trp
        35                  40                  45

Val Ala Thr Ile Gly Ser Arg Gly Thr Tyr Thr His Tyr Pro Asp Ser
    50                  55                  60

Val Lys Gly Arg Phe Thr Ile Ser Arg Asp Asn Asp Lys Asn Ala Leu
65                  70                  75                  80

Tyr Leu Gln Met Asn Ser Leu Lys Ser Glu Asp Thr Ala Met Tyr Tyr
                85                  90                  95

Cys Ala Arg Arg Ser Glu Phe Tyr Tyr Gly Asn Thr Tyr Tyr Tyr
            100                 105                 110

Ser Ala Met Asp Tyr Trp Gly Gln Gly Ala Ser Val Thr Val Ser Ser
        115                 120                 125

Gly Gly Gly Gly Ser Gly Gly Gly Gly Gly Gly Ser Asp
    130                 135                 140

Ile Val Leu Thr Gln Ser Pro Ala Ser Leu Ala Val Ser Leu Gly Gln
145                 150                 155                 160

Arg Ala Thr Ile Ser Cys Arg Ala Ser Glu Ser Val Asp Asn Tyr Gly
                165                 170                 175

Phe Ser Phe Met Asn Trp Phe Gln Gln Lys Pro Gly Gln Pro Pro Lys
            180                 185                 190

Leu Leu Ile Tyr Ala Ile Ser Asn Arg Gly Ser Gly Val Pro Ala Arg
        195                 200                 205

Phe Ser Gly Ser Gly Ser Gly Thr Asp Phe Ser Leu Asn Ile His Pro
    210                 215                 220

Val Glu Glu Asp Asp Pro Ala Met Tyr Phe Cys Gln Gln Thr Lys Glu
225                 230                 235                 240

Val Pro Trp Thr Phe Gly Gly Gly Thr Lys Leu Glu Ile Lys Gly Gly
                245                 250                 255

Gly Gly Ser Met Glu Val Gln Val Val Glu Ser Asp Gly Gly Leu Val
            260                 265                 270

Gln Pro Gly Arg Ser Leu Lys Leu Pro Cys Ala Ala Ser Gly Phe Thr
        275                 280                 285

Phe Ser Asp Tyr Tyr Met Ala Trp Val Arg Gln Ala Pro Thr Lys Gly
    290                 295                 300

Leu Glu Trp Val Ala Ser Ile Ser Tyr Asp Gly Ser Ser Thr Tyr Tyr
305                 310                 315                 320

Arg Asp Ser Val Lys Gly Arg Phe Thr Ile Ser Arg Asp Asn Ala Lys
                325                 330                 335

Ser Thr Leu Tyr Leu Gln Met Asp Ser Leu Arg Ser Glu Asp Thr Ala
            340                 345                 350

Thr Tyr Tyr Cys Gly Arg His Ser Ser Tyr Phe Asp Tyr Trp Gly Gln
```

```
              355                 360                 365
Gly Val Met Val Thr Val Ser Ser Gly Gly Gly Ser Gly Gly Gly
        370                 375                 380

Gly Ser Gly Gly Gly Ser Asp Thr Val Leu Thr Gln Ser Pro Ala
385                 390                 395                 400

Leu Ala Val Ser Pro Gly Glu Arg Val Thr Ile Ser Cys Arg Ala Ser
                405                 410                 415

Asp Ser Val Ser Thr Leu Met His Trp Tyr Gln Gln Lys Pro Gly Gln
            420                 425                 430

Gln Pro Lys Leu Leu Ile Tyr Leu Ala Ser His Leu Glu Ser Gly Val
        435                 440                 445

Pro Ala Arg Phe Ser Gly Ser Gly Ser Gly Thr Asp Phe Thr Leu Thr
    450                 455                 460

Ile Asp Pro Val Glu Ala Asp Asp Thr Ala Thr Tyr Tyr Cys Gln Gln
465                 470                 475                 480

Ser Trp Asn Asp Pro Trp Thr Phe Gly Gly Gly Thr Lys Leu Glu Leu
                485                 490                 495

Lys Asn Gly Ala Val Glu His His His His His His
            500                 505

<210> SEQ ID NO 17
<211> LENGTH: 1401
<212> TYPE: DNA
<213> ORGANISM: Artificial Sequence
<220> FEATURE:
<223> OTHER INFORMATION: BEAT 2 MHCII-c-myc-tag
<220> FEATURE:
<221> NAME/KEY: CDS
<222> LOCATION: (1)..(1398)

<400> SEQUENCE: 17 atg gag gtg cac ctg gtg gag tct ggg gga gac tta gtg aag cct gga      48
Met Glu Val His Leu Val Glu Ser Gly Gly Asp Leu Val Lys Pro Gly
1               5                   10                  15 ggg tcc ctg aaa ctc tcc tgt gca gcc tct gga ttc act ttc agt cac      96
Gly Ser Leu Lys Leu Ser Cys Ala Ala Ser Gly Phe Thr Phe Ser His
            20                  25                  30 tat ggc atg tct tgg gtt cgc cag act cca gac aag agg ctg gag tgg     144
Tyr Gly Met Ser Trp Val Arg Gln Thr Pro Asp Lys Arg Leu Glu Trp
        35                  40                  45 gtc gca acc att ggt agt cgt ggt act tac acc cac tat cca gac agt     192
Val Ala Thr Ile Gly Ser Arg Gly Thr Tyr Thr His Tyr Pro Asp Ser
    50                  55                  60 gtg aag gga cga ttc acc atc tcc aga gac aat gac aag aac gcc ctg     240
Val Lys Gly Arg Phe Thr Ile Ser Arg Asp Asn Asp Lys Asn Ala Leu
65                  70                  75                  80 tac ctg caa atg aac agt ctg aag tct gaa gac aca gcc atg tat tac     288
Tyr Leu Gln Met Asn Ser Leu Lys Ser Glu Asp Thr Ala Met Tyr Tyr
                85                  90                  95 tgt gca aga aga agt gaa ttt tat tac tac ggt aat acc tac tat tac     336
Cys Ala Arg Arg Ser Glu Phe Tyr Tyr Tyr Gly Asn Thr Tyr Tyr Tyr
            100                 105                 110 tct gct atg gac tac tgg ggt caa gga gcc tca gtc acc gtc tcc tca     384
Ser Ala Met Asp Tyr Trp Gly Gln Gly Ala Ser Val Thr Val Ser Ser
        115                 120                 125 ggt gga ggc ggt tca ggc gga ggt ggc tct ggc ggt ggc gga tcg gac     432
Gly Gly Gly Gly Ser Gly Gly Gly Gly Ser Gly Gly Gly Gly Ser Asp
    130                 135                 140 att gtg ctg acc caa tct cca gct tct ttg gct gta tct cta gga cag     480
Ile Val Leu Thr Gln Ser Pro Ala Ser Leu Ala Val Ser Leu Gly Gln
```

```
Ile Val Leu Thr Gln Ser Pro Ala Ser Leu Ala Val Ser Leu Gly Gln
145                 150                 155                 160 agg gcc acc atc tcc tgc aga gcc agc gaa agt gtt gat aat tat ggc    528
Arg Ala Thr Ile Ser Cys Arg Ala Ser Glu Ser Val Asp Asn Tyr Gly
                165                 170                 175 ttt agt ttt atg aac tgg ttc caa cag aaa cca gga cag cca ccc aaa    576
Phe Ser Phe Met Asn Trp Phe Gln Gln Lys Pro Gly Gln Pro Pro Lys
            180                 185                 190 ctc ctc atc tat gct ata tcc aac cga gga tcc ggg gtc cct gcc agg    624
Leu Leu Ile Tyr Ala Ile Ser Asn Arg Gly Ser Gly Val Pro Ala Arg
        195                 200                 205 ttt agt ggc agt ggg tct ggg aca gac ttc agc ctc aac atc cat cct    672
Phe Ser Gly Ser Gly Ser Gly Thr Asp Phe Ser Leu Asn Ile His Pro
    210                 215                 220 gta gag gag gat gat cct gca atg tat ttc tgt cag caa act aag gag    720
Val Glu Glu Asp Asp Pro Ala Met Tyr Phe Cys Gln Gln Thr Lys Glu
225                 230                 235                 240 gtt ccg tgg acg ttc ggt gga ggc acc aag ctg gaa atc aaa ggt gga    768
Val Pro Trp Thr Phe Gly Gly Gly Thr Lys Leu Glu Ile Lys Gly Gly
                245                 250                 255 ggc ggt tca gag gtg cag ctt cag gag tca gga cct ggc ctt gtg aaa    816
Gly Gly Ser Glu Val Gln Leu Gln Glu Ser Gly Pro Gly Leu Val Lys
            260                 265                 270 ccc tca cag tca ctc tcc ctc acc tgt tct gtc act gct tac ttc atc    864
Pro Ser Gln Ser Leu Ser Leu Thr Cys Ser Val Thr Ala Tyr Phe Ile
        275                 280                 285 act agt aat tac tgg gcc tgg atc cgg aag ttc cca gga aat aaa atg    912
Thr Ser Asn Tyr Trp Ala Trp Ile Arg Lys Phe Pro Gly Asn Lys Met
    290                 295                 300 gag tgg atg gga cac ata acc tac agt ggt tac act acc tac aat cca    960
Glu Trp Met Gly His Ile Thr Tyr Ser Gly Tyr Thr Thr Tyr Asn Pro
305                 310                 315                 320 tct ctc aaa agt cga atc tcc att act aga gac aca tcg agg aat cag    1008
Ser Leu Lys Ser Arg Ile Ser Ile Thr Arg Asp Thr Ser Arg Asn Gln
                325                 330                 335 ttc ttc ctc cag ttg aac tct gta act act gag gac aca gcc act tat    1056
Phe Phe Leu Gln Leu Asn Ser Val Thr Thr Glu Asp Thr Ala Thr Tyr
            340                 345                 350 tac tgt gca aga ggt gga ggt tca ggc gga ggt ggc tct ggc ggt        1104
Tyr Cys Ala Arg Gly Gly Gly Ser Gly Gly Gly Gly Ser Gly Gly
        355                 360                 365 ggc gga tcg aac att gta atg acc caa tct ccc aaa tcc atg tcc atg    1152
Gly Gly Ser Asn Ile Val Met Thr Gln Ser Pro Lys Ser Met Ser Met
370                 375                 380 tca gta gga gag agg gtc acc ttg acc tgc aag gcc agt gag aat gtg    1200
Ser Val Gly Glu Arg Val Thr Leu Thr Cys Lys Ala Ser Glu Asn Val
385                 390                 395                 400 gtt act tat gtt tcc tgg tat caa cag aaa cca gag cag tct cct aaa    1248
Val Thr Tyr Val Ser Trp Tyr Gln Gln Lys Pro Glu Gln Ser Pro Lys
                405                 410                 415 ctg ctg ata tac ggg gca tcc aac cgg tac act ggg gtc ccc gat cgc    1296
Leu Leu Ile Tyr Gly Ala Ser Asn Arg Tyr Thr Gly Val Pro Asp Arg
            420                 425                 430 ttc aca ggc agt gga tct gca aca gat ttc act ctg acc atc agc agt    1344
Phe Thr Gly Ser Gly Ser Ala Thr Asp Phe Thr Leu Thr Ile Ser Ser
        435                 440                 445 gtg cag gct gaa gac ctt gca gat tat cac tgt gga cag ggt tac agc    1392
Val Gln Ala Glu Asp Leu Ala Asp Tyr His Cys Gly Gln Gly Tyr Ser
    450                 455                 460
```

```
tat ccg taa                                                             1401
Tyr Pro
465
```

<210> SEQ ID NO 18
<211> LENGTH: 466
<212> TYPE: PRT
<213> ORGANISM: Artificial Sequence
<220> FEATURE:
<223> OTHER INFORMATION: Synthetic Construct

<400> SEQUENCE: 18

```
Met Glu Val His Leu Val Glu Ser Gly Gly Asp Leu Val Lys Pro Gly
1               5                   10                  15

Gly Ser Leu Lys Leu Ser Cys Ala Ala Ser Gly Phe Thr Phe Ser His
            20                  25                  30

Tyr Gly Met Ser Trp Val Arg Gln Thr Pro Asp Lys Arg Leu Glu Trp
        35                  40                  45

Val Ala Thr Ile Gly Ser Arg Gly Thr Tyr Thr His Tyr Pro Asp Ser
    50                  55                  60

Val Lys Gly Arg Phe Thr Ile Ser Arg Asp Asn Asp Lys Asn Ala Leu
65                  70                  75                  80

Tyr Leu Gln Met Asn Ser Leu Lys Ser Glu Asp Thr Ala Met Tyr Tyr
                85                  90                  95

Cys Ala Arg Arg Ser Glu Phe Tyr Tyr Tyr Gly Asn Thr Tyr Tyr Tyr
            100                 105                 110

Ser Ala Met Asp Tyr Trp Gly Gln Gly Ala Ser Val Thr Val Ser Ser
        115                 120                 125

Gly Gly Gly Gly Ser Gly Gly Gly Ser Gly Gly Gly Gly Ser Asp
    130                 135                 140

Ile Val Leu Thr Gln Ser Pro Ala Ser Leu Ala Val Ser Leu Gly Gln
145                 150                 155                 160

Arg Ala Thr Ile Ser Cys Arg Ala Ser Glu Ser Val Asp Asn Tyr Gly
                165                 170                 175

Phe Ser Phe Met Asn Trp Phe Gln Gln Lys Pro Gly Gln Pro Pro Lys
            180                 185                 190

Leu Leu Ile Tyr Ala Ile Ser Asn Arg Gly Ser Gly Val Pro Ala Arg
        195                 200                 205

Phe Ser Gly Ser Gly Ser Gly Thr Asp Phe Ser Leu Asn Ile His Pro
    210                 215                 220

Val Glu Glu Asp Asp Pro Ala Met Tyr Phe Cys Gln Gln Thr Lys Glu
225                 230                 235                 240

Val Pro Trp Thr Phe Gly Gly Gly Thr Lys Leu Glu Ile Lys Gly Gly
                245                 250                 255

Gly Gly Ser Glu Val Gln Leu Gln Glu Ser Gly Pro Gly Leu Val Lys
            260                 265                 270

Pro Ser Gln Ser Leu Ser Leu Thr Cys Ser Val Thr Ala Tyr Phe Ile
        275                 280                 285

Thr Ser Asn Tyr Trp Ala Trp Ile Arg Lys Phe Pro Gly Asn Lys Met
    290                 295                 300

Glu Trp Met Gly His Ile Thr Tyr Ser Gly Tyr Thr Thr Tyr Asn Pro
305                 310                 315                 320

Ser Leu Lys Ser Arg Ile Ser Ile Thr Arg Asp Thr Ser Arg Asn Gln
                325                 330                 335

Phe Phe Leu Gln Leu Asn Ser Val Thr Thr Glu Asp Thr Ala Thr Tyr
            340                 345                 350
```

```
Tyr Cys Ala Arg Gly Gly Gly Ser Gly Gly Gly Ser Gly Gly
            355                 360                 365

Gly Gly Ser Asn Ile Val Met Thr Gln Ser Pro Lys Ser Met Ser Met
    370                 375                 380

Ser Val Gly Glu Arg Val Thr Leu Thr Cys Lys Ala Ser Glu Asn Val
385                 390                 395                 400

Val Thr Tyr Val Ser Trp Tyr Gln Gln Lys Pro Glu Gln Ser Pro Lys
                405                 410                 415

Leu Leu Ile Tyr Gly Ala Ser Asn Arg Tyr Thr Gly Val Pro Asp Arg
            420                 425                 430

Phe Thr Gly Ser Gly Ser Ala Thr Asp Phe Thr Leu Thr Ile Ser Ser
        435                 440                 445

Val Gln Ala Glu Asp Leu Ala Asp Tyr His Cys Gly Gln Gly Tyr Ser
    450                 455                 460

Tyr Pro
465
```

<210> SEQ ID NO 19
<211> LENGTH: 1542
<212> TYPE: DNA
<213> ORGANISM: Artificial Sequence
<220> FEATURE:
<223> OTHER INFORMATION: BEAT 3 CD40-anti-CD3
<220> FEATURE:
<221> NAME/KEY: CDS
<222> LOCATION: (1)..(1539)

<400> SEQUENCE: 19

```
atg gag aca gac aca ctc ctg cta tgg gta ctg ctg ctc tgg gtt cca       48
Met Glu Thr Asp Thr Leu Leu Leu Trp Val Leu Leu Leu Trp Val Pro
1               5                   10                  15 ggt tcc act ggt gac gag gtg cag ctg gtg gag tct ggg gga ggc ttg       96
Gly Ser Thr Gly Asp Glu Val Gln Leu Val Glu Ser Gly Gly Gly Leu
            20                  25                  30 gtg cag cct gga aag tcc ctg aaa ctc tcc tgt gag gcc tct gga ttc      144
Val Gln Pro Gly Lys Ser Leu Lys Leu Ser Cys Glu Ala Ser Gly Phe
        35                  40                  45 acc ttc agc ggc tat ggc atg cac tgg gtc cgc cag gct cca ggg agg      192
Thr Phe Ser Gly Tyr Gly Met His Trp Val Arg Gln Ala Pro Gly Arg
    50                  55                  60 ggg ctg gag tcg gtc gca tac att act agt agt agt att aat atc aaa      240
Gly Leu Glu Ser Val Ala Tyr Ile Thr Ser Ser Ser Ile Asn Ile Lys
65                  70                  75                  80 tat gct gac gct gtg aaa ggc cgg ttc acc gtc tcc aga gac aat gcc      288
Tyr Ala Asp Ala Val Lys Gly Arg Phe Thr Val Ser Arg Asp Asn Ala
                85                  90                  95 aag aac tta ctg ttt cta caa atg aac att ctc aag tct gag gac aca      336
Lys Asn Leu Leu Phe Leu Gln Met Asn Ile Leu Lys Ser Glu Asp Thr
            100                 105                 110 gcc atg tac tac tgt gca aga ttc gac tgg gac aaa aat tac tgg ggc      384
Ala Met Tyr Tyr Cys Ala Arg Phe Asp Trp Asp Lys Asn Tyr Trp Gly
        115                 120                 125 caa gga acc atg gtc acc gtc tcc tca ggt gga ggc ggt tca ggc gga      432
Gln Gly Thr Met Val Thr Val Ser Ser Gly Gly Gly Gly Ser Gly Gly
    130                 135                 140 ggt ggc tct ggc ggt ggc gga tcg gac atc cag atg acc cag tct cca      480
Gly Gly Ser Gly Gly Gly Gly Ser Asp Ile Gln Met Thr Gln Ser Pro
145                 150                 155                 160 tca tca ctg cct gcc tcc ctg gga gac aga gtc act atc aat tgt cag      528
```

```
                Ser Ser Leu Pro Ala Ser Leu Gly Asp Arg Val Thr Ile Asn Cys Gln
                            165             170                 175 gcc agt cag gac att agc aat tat tta aac tgg tac cag cag aaa cca          576
Ala Ser Gln Asp Ile Ser Asn Tyr Leu Asn Trp Tyr Gln Gln Lys Pro
            180                 185                 190 ggg aaa gct cct aag ctc ctg atc tat tat aca aat aaa ttg gca gat          624
Gly Lys Ala Pro Lys Leu Leu Ile Tyr Tyr Thr Asn Lys Leu Ala Asp
            195                 200                 205 gga gtc cca tca agg ttc agt ggc agt ggt tct ggg aga gat tct tct          672
Gly Val Pro Ser Arg Phe Ser Gly Ser Gly Ser Gly Arg Asp Ser Ser
            210                 215                 220 ttc act atc agc agc ctg gaa tcc gaa gat att gga tct tat tac tgt          720
Phe Thr Ile Ser Ser Leu Glu Ser Glu Asp Ile Gly Ser Tyr Tyr Cys
225                 230                 235                 240 caa cag tat tat aac tat ccg tgg acg ttc gga cct ggc acc aag ctg          768
Gln Gln Tyr Tyr Asn Tyr Pro Trp Thr Phe Gly Pro Gly Thr Lys Leu
            245                 250                 255 gaa atc aaa ggt gga ggc ggt tca atg gag gtg cag gtg gtg gag tct          816
Glu Ile Lys Gly Gly Gly Gly Ser Met Glu Val Gln Val Val Glu Ser
            260                 265                 270 gat gga ggc tta gtg cag cct gga agg tcc cta aaa ctc ccc tgt gca          864
Asp Gly Gly Leu Val Gln Pro Gly Arg Ser Leu Lys Leu Pro Cys Ala
            275                 280                 285 gcc tca gga ttc act ttc agt gac tat tac atg gcc tgg gtc cgc cag          912
Ala Ser Gly Phe Thr Phe Ser Asp Tyr Tyr Met Ala Trp Val Arg Gln
            290                 295                 300 gct cca acg aag ggg ctg gag tgg gtc gca agc att agt tat gat ggt          960
Ala Pro Thr Lys Gly Leu Glu Trp Val Ala Ser Ile Ser Tyr Asp Gly
305                 310                 315                 320 agt agc act tac tat cga gac tcc gtg aag ggc cga ttc act atc tcc         1008
Ser Ser Thr Tyr Tyr Arg Asp Ser Val Lys Gly Arg Phe Thr Ile Ser
            325                 330                 335 aga gat aat gca aaa agc acc cta tac ctg caa atg gac agt ctg agg         1056
Arg Asp Asn Ala Lys Ser Thr Leu Tyr Leu Gln Met Asp Ser Leu Arg
            340                 345                 350 tct gag gac acg gcc act tat tac tgc gga aga cac agt agc tac ttt         1104
Ser Glu Asp Thr Ala Thr Tyr Tyr Cys Gly Arg His Ser Ser Tyr Phe
            355                 360                 365 gat tac tgg ggc caa gga gtc atg gtc aca gtc tcc tca ggt gga ggc         1152
Asp Tyr Trp Gly Gln Gly Val Met Val Thr Val Ser Ser Gly Gly Gly
            370                 375                 380 ggt tca ggc gga ggt ggc tct ggc ggt ggc gga tcg gac act gta ctg         1200
Gly Ser Gly Gly Gly Gly Ser Gly Gly Gly Gly Ser Asp Thr Val Leu
385                 390                 395                 400 acc cag tct cct gct ttg gct gtg tct cca gga gag agg gtt acc atc         1248
Thr Gln Ser Pro Ala Leu Ala Val Ser Pro Gly Glu Arg Val Thr Ile
            405                 410                 415 tcc tgt agg gcc agt gac agt gtc agt aca ctt atg cac tgg tac caa         1296
Ser Cys Arg Ala Ser Asp Ser Val Ser Thr Leu Met His Trp Tyr Gln
            420                 425                 430 cag aaa cca gga cag caa ccc aaa ctc ctc atc tat cta gca tca cac         1344
Gln Lys Pro Gly Gln Gln Pro Lys Leu Leu Ile Tyr Leu Ala Ser His
            435                 440                 445 cta gaa tct ggg gtc cct gcc agg ttc agt ggc agt ggg tct ggg aca         1392
Leu Glu Ser Gly Val Pro Ala Arg Phe Ser Gly Ser Gly Ser Gly Thr
            450                 455                 460 gac ttc acc ctc acc att gat cct gtg gag gct gat gac act gca acc         1440
Asp Phe Thr Leu Thr Ile Asp Pro Val Glu Ala Asp Asp Thr Ala Thr
465                 470                 475                 480
```

-continued

```
tat tac tgt cag cag agt tgg aat gat ccg tgg acg ttc ggt gga ggc    1488
Tyr Tyr Cys Gln Gln Ser Trp Asn Asp Pro Trp Thr Phe Gly Gly Gly
            485                 490                 495 acc aag ctg gaa ttg aaa aat ggg gcc gtc gag cac cac cac cac cac    1536
Thr Lys Leu Glu Leu Lys Asn Gly Ala Val Glu His His His His His
        500                 505                 510 cac tga                                                             1542
His
```

<210> SEQ ID NO 20
<211> LENGTH: 513
<212> TYPE: PRT
<213> ORGANISM: Artificial Sequence
<220> FEATURE:
<223> OTHER INFORMATION: Synthetic Construct

<400> SEQUENCE: 20

```
Met Glu Thr Asp Thr Leu Leu Leu Trp Val Leu Leu Leu Trp Val Pro
1               5                   10                  15

Gly Ser Thr Gly Asp Glu Val Gln Leu Val Glu Ser Gly Gly Gly Leu
            20                  25                  30

Val Gln Pro Gly Lys Ser Leu Lys Leu Ser Cys Glu Ala Ser Gly Phe
        35                  40                  45

Thr Phe Ser Gly Tyr Gly Met His Trp Val Arg Gln Ala Pro Gly Arg
    50                  55                  60

Gly Leu Glu Ser Val Ala Tyr Ile Thr Ser Ser Ile Asn Ile Lys
65                  70                  75                  80

Tyr Ala Asp Ala Val Lys Gly Arg Phe Thr Val Ser Arg Asp Asn Ala
                85                  90                  95

Lys Asn Leu Leu Phe Leu Gln Met Asn Ile Leu Lys Ser Glu Asp Thr
            100                 105                 110

Ala Met Tyr Tyr Cys Ala Arg Phe Asp Trp Asp Lys Asn Tyr Trp Gly
        115                 120                 125

Gln Gly Thr Met Val Thr Val Ser Ser Gly Gly Gly Ser Gly Gly
    130                 135                 140

Gly Gly Ser Gly Gly Gly Ser Asp Ile Gln Met Thr Gln Ser Pro
145                 150                 155                 160

Ser Ser Leu Pro Ala Ser Leu Gly Asp Arg Val Thr Ile Asn Cys Gln
                165                 170                 175

Ala Ser Gln Asp Ile Ser Asn Tyr Leu Asn Trp Tyr Gln Gln Lys Pro
            180                 185                 190

Gly Lys Ala Pro Lys Leu Leu Ile Tyr Tyr Thr Asn Lys Leu Ala Asp
        195                 200                 205

Gly Val Pro Ser Arg Phe Ser Gly Ser Gly Ser Gly Arg Asp Ser Ser
    210                 215                 220

Phe Thr Ile Ser Ser Leu Glu Ser Glu Asp Ile Gly Ser Tyr Tyr Cys
225                 230                 235                 240

Gln Gln Tyr Tyr Asn Tyr Pro Trp Thr Phe Gly Pro Gly Thr Lys Leu
                245                 250                 255

Glu Ile Lys Gly Gly Gly Gly Ser Met Glu Val Gln Val Val Glu Ser
            260                 265                 270

Asp Gly Gly Leu Val Gln Pro Gly Arg Ser Leu Lys Leu Pro Cys Ala
        275                 280                 285

Ala Ser Gly Phe Thr Phe Ser Asp Tyr Tyr Met Ala Trp Val Arg Gln
    290                 295                 300

Ala Pro Thr Lys Gly Leu Glu Trp Val Ala Ser Ile Ser Tyr Asp Gly
```

-continued

```
                305                 310                 315                 320
        Ser Ser Thr Tyr Tyr Arg Asp Ser Val Lys Gly Arg Phe Thr Ile Ser
                        325                 330                 335

Arg Asp Asn Ala Lys Ser Thr Leu Tyr Leu Gln Met Asp Ser Leu Arg
                        340                 345                 350

Ser Glu Asp Thr Ala Thr Tyr Tyr Cys Gly Arg His Ser Ser Tyr Phe
                        355                 360                 365

Asp Tyr Trp Gly Gln Gly Val Met Val Thr Val Ser Ser Gly Gly Gly
                        370                 375                 380

Gly Ser Gly Gly Gly Ser Gly Gly Gly Ser Asp Thr Val Leu
        385                 390                 395                 400

Thr Gln Ser Pro Ala Leu Ala Val Ser Pro Gly Glu Arg Val Thr Ile
                            405                 410                 415

Ser Cys Arg Ala Ser Asp Ser Val Ser Thr Leu Met His Trp Tyr Gln
                            420                 425                 430

Gln Lys Pro Gly Gln Gln Pro Lys Leu Leu Ile Tyr Leu Ala Ser His
                        435                 440                 445

Leu Glu Ser Gly Val Pro Ala Arg Phe Ser Gly Ser Gly Ser Gly Thr
        450                 455                 460

Asp Phe Thr Leu Thr Ile Asp Pro Val Glu Ala Asp Asp Thr Ala Thr
        465                 470                 475                 480

Tyr Tyr Cys Gln Gln Ser Trp Asn Asp Pro Trp Thr Phe Gly Gly Gly
                        485                 490                 495

Thr Lys Leu Glu Leu Lys Asn Gly Ala Val Glu His His His His
                        500                 505                 510

His
```

```
<210> SEQ ID NO 21
<211> LENGTH: 1413
<212> TYPE: DNA
<213> ORGANISM: Artificial Sequence
<220> FEATURE:
<223> OTHER INFORMATION: BEAT 4 MHCII-anti-CD3
<220> FEATURE:
<221> NAME/KEY: CDS
<222> LOCATION: (1)..(1413)

<400> SEQUENCE: 21
```

| | | | | | | | | | | | | | | | | |
|---|---|---|---|---|---|---|---|---|---|---|---|---|---|---|---|---|
| atg | gag | aca | gac | aca | ctc | ctg | cta | tgg | gta | ctg | ctg | ctc | tgg | gtt | cca | 48 |
| Met | Glu | Thr | Asp | Thr | Leu | Leu | Leu | Trp | Val | Leu | Leu | Leu | Trp | Val | Pro | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggt | tcc | act | ggt | gac | gag | gtg | cag | ctg | gtg | gag | tct | ggg | gga | ggc | ttg | 96 |
| Gly | Ser | Thr | Gly | Asp | Glu | Val | Gln | Leu | Val | Glu | Ser | Gly | Gly | Gly | Leu | |
| | | | 20 | | | | | 25 | | | | | 30 | | | |

| | | | | | | | | | | | | | | | | |
|---|---|---|---|---|---|---|---|---|---|---|---|---|---|---|---|---|
| gtg | cag | cct | gga | aag | tcc | ctg | aaa | ctc | tcc | tgt | gag | gcc | tct | gga | ttc | 144 |
| Val | Gln | Pro | Gly | Lys | Ser | Leu | Lys | Leu | Ser | Cys | Glu | Ala | Ser | Gly | Phe | |
| | | | | 35 | | | | | 40 | | | | | 45 | | |

| | | | | | | | | | | | | | | | | |
|---|---|---|---|---|---|---|---|---|---|---|---|---|---|---|---|---|
| acc | ttc | agc | ggc | tat | ggc | atg | cac | tgg | gtc | cgc | cag | gct | cca | ggg | agg | 192 |
| Thr | Phe | Ser | Gly | Tyr | Gly | Met | His | Trp | Val | Arg | Gln | Ala | Pro | Gly | Arg | |
| | | | 50 | | | | | 55 | | | | | 60 | | | |

| | | | | | | | | | | | | | | | | |
|---|---|---|---|---|---|---|---|---|---|---|---|---|---|---|---|---|
| ggg | ctg | gag | tcg | gtc | gca | tac | att | act | agt | agt | agt | att | aat | atc | aaa | 240 |
| Gly | Leu | Glu | Ser | Val | Ala | Tyr | Ile | Thr | Ser | Ser | Ser | Ile | Asn | Ile | Lys | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| tat | gct | gac | gct | gtg | aaa | ggc | cgg | ttc | acc | gtc | tcc | aga | gac | aat | gcc | 288 |
| Tyr | Ala | Asp | Ala | Val | Lys | Gly | Arg | Phe | Thr | Val | Ser | Arg | Asp | Asn | Ala | |
| | | | | 85 | | | | | 90 | | | | | 95 | | |

| | | | | | | | | | | | | | | | | |
|---|---|---|---|---|---|---|---|---|---|---|---|---|---|---|---|---|
| aag | aac | tta | ctg | ttt | cta | caa | atg | aac | att | ctc | aag | tct | gag | gac | aca | 336 |
| Lys | Asn | Leu | Leu | Phe | Leu | Gln | Met | Asn | Ile | Leu | Lys | Ser | Glu | Asp | Thr | |

-continued

|     |     | 100 |     |     | 105 |     |     |     | 110 |     |     |     |     |     |
|-----|-----|-----|-----|-----|-----|-----|-----|-----|-----|-----|-----|-----|-----|-----|
| gcc | atg | tac | tac | tgt | gca | aga | ttc | gac | tgg | gac | aaa | aat | tac | tgg | ggc | 384 |
| Ala | Met | Tyr | Tyr | Cys | Ala | Arg | Phe | Asp | Trp | Asp | Lys | Asn | Tyr | Trp | Gly |
|     |     | 115 |     |     |     | 120 |     |     |     | 125 |     |     |     |     |     |

| caa | gga | acc | atg | gtc | acc | gtc | tcc | tca | ggt | gga | ggc | ggt | tca | ggc | gga | 432 |
| Gln | Gly | Thr | Met | Val | Thr | Val | Ser | Ser | Gly | Gly | Gly | Gly | Ser | Gly | Gly |
|     | 130 |     |     |     |     | 135 |     |     |     | 140 |     |     |     |     |     |

| ggt | ggc | tct | ggc | ggt | ggc | gga | tcg | gac | atc | cag | atg | acc | cag | tct | cca | 480 |
| Gly | Gly | Ser | Gly | Gly | Gly | Gly | Ser | Asp | Ile | Gln | Met | Thr | Gln | Ser | Pro |
| 145 |     |     |     | 150 |     |     |     |     | 155 |     |     |     |     | 160 |     |

| tca | tca | ctg | cct | gcc | tcc | ctg | gga | gac | aga | gtc | act | atc | aat | tgt | cag | 528 |
| Ser | Ser | Leu | Pro | Ala | Ser | Leu | Gly | Asp | Arg | Val | Thr | Ile | Asn | Cys | Gln |
|     |     |     |     | 165 |     |     |     |     | 170 |     |     |     |     | 175 |     |

| gcc | agt | cag | gac | att | agc | aat | tat | tta | aac | tgg | tac | cag | cag | aaa | cca | 576 |
| Ala | Ser | Gln | Asp | Ile | Ser | Asn | Tyr | Leu | Asn | Trp | Tyr | Gln | Gln | Lys | Pro |
|     |     |     | 180 |     |     |     |     | 185 |     |     |     |     | 190 |     |     |

| ggg | aaa | gct | cct | aag | ctc | ctg | atc | tat | tat | aca | aat | aaa | ttg | gca | gat | 624 |
| Gly | Lys | Ala | Pro | Lys | Leu | Leu | Ile | Tyr | Tyr | Thr | Asn | Lys | Leu | Ala | Asp |
|     |     |     | 195 |     |     |     |     | 200 |     |     |     |     | 205 |     |     |

| gga | gtc | cca | tca | agg | ttc | agt | ggc | agt | ggt | tct | ggg | aga | gat | tct | tct | 672 |
| Gly | Val | Pro | Ser | Arg | Phe | Ser | Gly | Ser | Gly | Ser | Gly | Arg | Asp | Ser | Ser |
|     | 210 |     |     |     |     | 215 |     |     |     |     | 220 |     |     |     |     |

| ttc | act | atc | agc | agc | ctg | gaa | tcc | gaa | gat | att | gga | tct | tat | tac | tgt | 720 |
| Phe | Thr | Ile | Ser | Ser | Leu | Glu | Ser | Glu | Asp | Ile | Gly | Ser | Tyr | Tyr | Cys |
| 225 |     |     |     |     | 230 |     |     |     |     | 235 |     |     |     |     | 240 |

| caa | cag | tat | tat | aac | tat | ccg | tgg | acg | ttc | gga | cct | ggc | acc | aag | ctg | 768 |
| Gln | Gln | Tyr | Tyr | Asn | Tyr | Pro | Trp | Thr | Phe | Gly | Pro | Gly | Thr | Lys | Leu |
|     |     |     |     | 245 |     |     |     |     | 250 |     |     |     |     | 255 |     |

| gaa | atc | aaa | ggt | gga | ggc | ggt | tca | gag | gtg | cag | ctt | cag | gag | tca | gga | 816 |
| Glu | Ile | Lys | Gly | Gly | Gly | Gly | Ser | Glu | Val | Gln | Leu | Gln | Glu | Ser | Gly |
|     |     |     | 260 |     |     |     |     | 265 |     |     |     |     | 270 |     |     |

| cct | ggc | ctt | gtg | aaa | ccc | tca | cag | tca | ctc | tcc | ctc | acc | tgt | tct | gtc | 864 |
| Pro | Gly | Leu | Val | Lys | Pro | Ser | Gln | Ser | Leu | Ser | Leu | Thr | Cys | Ser | Val |
|     |     | 275 |     |     |     |     | 280 |     |     |     |     | 285 |     |     |     |

| act | gct | tac | ttc | atc | act | agt | aat | tac | tgg | gcc | tgg | atc | cgg | aag | ttc | 912 |
| Thr | Ala | Tyr | Phe | Ile | Thr | Ser | Asn | Tyr | Trp | Ala | Trp | Ile | Arg | Lys | Phe |
|     | 290 |     |     |     |     | 295 |     |     |     |     | 300 |     |     |     |     |

| cca | gga | aat | aaa | atg | gag | tgg | atg | gga | cac | ata | acc | tac | agt | ggt | tac | 960 |
| Pro | Gly | Asn | Lys | Met | Glu | Trp | Met | Gly | His | Ile | Thr | Tyr | Ser | Gly | Tyr |
| 305 |     |     |     | 310 |     |     |     |     | 315 |     |     |     |     | 320 |     |

| act | acc | tac | aat | cca | tct | ctc | aaa | agt | cga | atc | tcc | att | act | aga | gac | 1008 |
| Thr | Thr | Tyr | Asn | Pro | Ser | Leu | Lys | Ser | Arg | Ile | Ser | Ile | Thr | Arg | Asp |
|     |     |     |     | 325 |     |     |     |     | 330 |     |     |     |     | 335 |     |

| aca | tcg | agg | aat | cag | ttc | ttc | ctc | cag | ttg | aac | tct | gta | act | act | gag | 1056 |
| Thr | Ser | Arg | Asn | Gln | Phe | Phe | Leu | Gln | Leu | Asn | Ser | Val | Thr | Thr | Glu |
|     |     |     | 340 |     |     |     |     | 345 |     |     |     |     | 350 |     |     |

| gac | aca | gcc | act | tat | tac | tgt | gca | aga | ggt | gga | ggc | ggt | tca | ggc | gga | 1104 |
| Asp | Thr | Ala | Thr | Tyr | Tyr | Cys | Ala | Arg | Gly | Gly | Gly | Gly | Ser | Gly | Gly |
|     |     | 355 |     |     |     |     | 360 |     |     |     |     | 365 |     |     |     |

| ggt | ggc | tct | ggc | ggt | ggc | gga | tcg | aac | att | gta | atg | acc | caa | tct | ccc | 1152 |
| Gly | Gly | Ser | Gly | Gly | Gly | Gly | Ser | Asn | Ile | Val | Met | Thr | Gln | Ser | Pro |
|     | 370 |     |     |     |     | 375 |     |     |     |     | 380 |     |     |     |     |

| aaa | tcc | atg | tcc | atg | tca | gta | gga | gag | agg | gtc | acc | ttg | acc | tgc | aag | 1200 |
| Lys | Ser | Met | Ser | Met | Ser | Val | Gly | Glu | Arg | Val | Thr | Leu | Thr | Cys | Lys |
| 385 |     |     |     | 390 |     |     |     |     | 395 |     |     |     |     | 400 |     |

| gcc | agt | gag | aat | gtg | gtt | act | tat | gtt | tcc | tgg | tat | caa | cag | aaa | cca | 1248 |
| Ala | Ser | Glu | Asn | Val | Val | Thr | Tyr | Val | Ser | Trp | Tyr | Gln | Gln | Lys | Pro |
|     |     |     |     | 405 |     |     |     |     | 410 |     |     |     |     | 415 |     |

| gag | cag | tct | cct | aaa | ctg | ctg | ata | tac | ggg | gca | tcc | aac | cgg | tac | act | 1296 |

```
Glu Gln Ser Pro Lys Leu Leu Ile Tyr Gly Ala Ser Asn Arg Tyr Thr
                420                 425                 430 ggg gtc ccc gat cgc ttc aca ggc agt gga tct gca aca gat ttc act    1344
Gly Val Pro Asp Arg Phe Thr Gly Ser Gly Ser Ala Thr Asp Phe Thr
                435                 440                 445 ctg acc atc agc agt gtg cag gct gaa gac ctt gca gat tat cac tgt    1392
Leu Thr Ile Ser Ser Val Gln Ala Glu Asp Leu Ala Asp Tyr His Cys
            450                 455                 460 gga cag ggt tac agc tat ccg                                        1413
Gly Gln Gly Tyr Ser Tyr Pro
465                 470
```

<210> SEQ ID NO 22
<211> LENGTH: 471
<212> TYPE: PRT
<213> ORGANISM: Artificial Sequence
<220> FEATURE:
<223> OTHER INFORMATION: Synthetic Construct

<400> SEQUENCE: 22

```
Met Glu Thr Asp Thr Leu Leu Leu Trp Val Leu Leu Leu Trp Val Pro
1               5                   10                  15

Gly Ser Thr Gly Asp Glu Val Gln Leu Val Glu Ser Gly Gly Gly Leu
            20                  25                  30

Val Gln Pro Gly Lys Ser Leu Lys Leu Ser Cys Glu Ala Ser Gly Phe
        35                  40                  45

Thr Phe Ser Gly Tyr Gly Met His Trp Val Arg Gln Ala Pro Gly Arg
    50                  55                  60

Gly Leu Glu Ser Val Ala Tyr Ile Thr Ser Ser Ile Asn Ile Lys
65                  70                  75                  80

Tyr Ala Asp Ala Val Lys Gly Arg Phe Thr Val Ser Arg Asp Asn Ala
                85                  90                  95

Lys Asn Leu Leu Phe Leu Gln Met Asn Ile Leu Lys Ser Glu Asp Thr
            100                 105                 110

Ala Met Tyr Tyr Cys Ala Arg Phe Asp Trp Asp Lys Asn Tyr Trp Gly
        115                 120                 125

Gln Gly Thr Met Val Thr Val Ser Ser Gly Gly Gly Gly Ser Gly Gly
    130                 135                 140

Gly Gly Ser Gly Gly Gly Ser Asp Ile Gln Met Thr Gln Ser Pro
145                 150                 155                 160

Ser Ser Leu Pro Ala Ser Leu Gly Asp Arg Val Thr Ile Asn Cys Gln
                165                 170                 175

Ala Ser Gln Asp Ile Ser Asn Tyr Leu Asn Trp Tyr Gln Gln Lys Pro
            180                 185                 190

Gly Lys Ala Pro Lys Leu Leu Ile Tyr Tyr Thr Asn Lys Leu Ala Asp
        195                 200                 205

Gly Val Pro Ser Arg Phe Ser Gly Ser Gly Ser Gly Arg Asp Ser Ser
    210                 215                 220

Phe Thr Ile Ser Ser Leu Glu Ser Glu Asp Ile Gly Ser Tyr Tyr Cys
225                 230                 235                 240

Gln Gln Tyr Tyr Asn Tyr Pro Trp Thr Phe Gly Pro Gly Thr Lys Leu
                245                 250                 255

Glu Ile Lys Gly Gly Gly Gly Ser Glu Val Gln Leu Gln Glu Ser Gly
            260                 265                 270

Pro Gly Leu Val Lys Pro Ser Gln Ser Leu Ser Leu Thr Cys Ser Val
        275                 280                 285
```

```
Thr Ala Tyr Phe Ile Thr Ser Asn Tyr Trp Ala Trp Ile Arg Lys Phe
        290                 295                 300
Pro Gly Asn Lys Met Glu Trp Met Gly His Ile Thr Tyr Ser Gly Tyr
305                 310                 315                 320
Thr Thr Tyr Asn Pro Ser Leu Lys Ser Arg Ile Ser Ile Thr Arg Asp
                325                 330                 335
Thr Ser Arg Asn Gln Phe Phe Leu Gln Leu Asn Ser Val Thr Thr Glu
            340                 345                 350
Asp Thr Ala Thr Tyr Tyr Cys Ala Arg Gly Gly Gly Ser Gly Gly
        355                 360                 365
Gly Gly Ser Gly Gly Gly Ser Asn Ile Val Met Thr Gln Ser Pro
370                 375                 380
Lys Ser Met Ser Met Ser Val Gly Glu Arg Val Thr Leu Thr Cys Lys
385                 390                 395                 400
Ala Ser Glu Asn Val Val Thr Tyr Val Ser Trp Tyr Gln Gln Lys Pro
                405                 410                 415
Glu Gln Ser Pro Lys Leu Leu Ile Tyr Gly Ala Ser Asn Arg Tyr Thr
            420                 425                 430
Gly Val Pro Asp Arg Phe Thr Gly Ser Gly Ser Ala Thr Asp Phe Thr
        435                 440                 445
Leu Thr Ile Ser Ser Val Gln Ala Glu Asp Leu Ala Asp Tyr His Cys
    450                 455                 460
Gly Gln Gly Tyr Ser Tyr Pro
465                 470

<210> SEQ ID NO 23
<211> LENGTH: 5497
<212> TYPE: DNA
<213> ORGANISM: Artificial Sequence
<220> FEATURE:
<223> OTHER INFORMATION: BEAT 1 vector

<400> SEQUENCE: 23
gaattaattc ataccagatc accgaaaact gtcctccaaa tgtgtccccc tcacactccc      60
aaattcgcgg gcttctgctc ttagaccact ctaccctatt ccccacactc accggagcca     120
aagccgcggc ccttccgttt ctttgctttt gaaagacccc acccgtaggt ggcaagctag     180
cttaagtaac gccactttgc aaggcatgga aaaatacata actgagaata ggaaagttca     240
gatcaaggtc aggaacaaag aaacagctga ataccaaaca ggatatctgt ggtaagcggt     300
tcctgccccg gctcagggcc aagaacagat gagacagctg agtgatgggc caaacaggat     360
atctgtggta agcagttcct gccccggctc ggggccaaga acagatggtc cccagatgcg     420
gtccagccct cagcagtttc tagtgaatca tcagatgttt ccagggtgcc ccaaggacct     480
gaaaatgacc ctgtacctta tttgaactaa ccaatcagtt cgcttctcgc ttctgttcgc     540
gcgcttccgc tctccgagct caataaaaga gcccacaacc cctcactcgg cgcgccagtc     600
ttccgataga ctgcgtcgcc cgggtacccg tattcccaat aaagcctctt gctgtttgca     660
tccgaatcgt ggtctcgctg ttccttggga gggtctcctc tgagtgattg actacccacg     720
acggggggtct ttcatttggg ggctcgtccg ggatttggag accccccgccc agggaccacc     780
gacccaccac cgggaggtaa gctggccagc aacctatctg tgtctgtccg attgtctagt     840
gtctatgttt gatgttatgc gcctgcgtct gtactagtta gctaactagc tctgtatctg     900
gcggaccccgt ggtggaactg acgagttctg aacacccggc cgcaacccag ggagacgtcc     960
cagggacttt gggggccgtt tttgtggccc gacctgagga agggagtcga tgtggaatcc    1020
```

```
gaccccgtca ggatatgtgg ttctggtagg agacgagaac ctaaaacagt tcccgcctcc    1080
gtctgaattt ttgctttcgg tttggaaccg aagccgcgcg tcttgtctgc tgcagcatcg    1140
ttctgtgttg tctctgtctg actgtgtttc tgtatttgtc tgaaaattag ggccagactg    1200
ttaccactcc cttaagtttg accttaggtc actggaaaga tgtcgagcgg atcgctcaca    1260
accagtcggt agatgtcaag aagagacgtt gggttacctt ctgctctgca gaatggccaa    1320
cctttaacgt cggatggccg cgagacggca cctttaaccg agacctcatc acccaggtta    1380
agatcaaggt cttttcacct ggcccgcatg gacacccaga ccaggtcccc tacatcgtga    1440
cctgggaagc cttggctttt gaccccctc cctgggtcaa gccctttgta caccctaagc    1500
ctccgcctcc tcttcctcca tccgccccgt ctctcccccct tgaacctcct cgttcgaccc    1560
cgcctcgatc ctcccttat ccagcccca ctccttctct aggcgccgga attccggccg    1620
tgacaagagt tactaacagc ccctctctcc aagctcactt acaggctctc tacttagtcc    1680
agcacgaagt ctggagacct ctggcggcag cctaccaaga caactggac cgaccggtgg    1740 tacctcaccc ttaccgagtc ggcgacacag tgtgggtccg ccgacaccag actaagaacc    1800
tagaacctcg ctggaaagga ccttacacag tcctgcagac caccccacc gccctcaaag    1860 tagacggcat cgcagcttgg atacacgccg cccacgtgaa ggctgccgac cccggggtg    1920 gaccatctct agactgacgc ggccgcccac cgaggtgcac ctggtggagt ctggggaga    1980 cttagtgaag cctggagggt ccctgaaact ctcctgtgca gcctctggat tcactttcag    2040
tcactatggc atgtcttggg ttcgccagac tccagacaag aggctggagt gggtcgcaac    2100
cattggtagt cgtggtactt acacccacta tccagacagt gtgaagggac gattcaccat    2160
ctccagagac aatgcaaga acgccctgta cctgcaaatg aacagtctga agtctgaaga    2220
cacagccatg tattactgtg caagaagaag tgaattttat tactacggta atacctacta    2280
ttactctgct atggactact ggggtcaagg agcctcagtc accgtctcct caggtggagg    2340
cggttcaggc ggaggtggct ctggcggtgg cggatcggac attgtgctga cccaatctcc    2400
agcttctttg gctgtatctc taggacagag ggccaccatc tcctgcagag ccagcgaaag    2460
tgttgataat tatggctta gttttatgaa ctggttccaa cagaaaccag acagccacc    2520 caaactcctc atctatgcta tatccaaccg aggatccggg gtccctgcca ggtttagtgg    2580
cagtgggtct gggacagact tcagcctcaa catccatcct gtagaggagg atgatcctgc    2640
aatgtatttc tgtcagcaaa ctaaggaggt tccgtggacg ttcggtggag gcaccaagct    2700
ggaaatcaaa ggtggaggcg gttcaatgga ggtgcaggtg gtggagtctg atggaggctt    2760
agtgcagcct ggaaggtccc taaaactccc ctgtgcagcc tcaggattca ctttcagtga    2820
ctattacatg gcctgggtcc gccaggctcc aacgaagggg ctggagtggg tcgcaagcat    2880
tagttatgat ggtagtagca cttactatcg agactccgtg aagggccgat tcactatctc    2940
cagagataat gcaaaagca ccctatacct gcaaatggac agtctgaggt ctgaggacac    3000
ggccacttat tactgcggaa gacacagtag ctactttgat tactggggcc aaggagtcat    3060
ggtcacagtc tcctcaggtg gaggcggttc aggcggaggt ggctctggcg gtggcggatc    3120
ggacactgta ctgacccagt ctcctgcttt ggctgtgtct ccaggagaga gggttaccat    3180
ctcctgtagg gccagtgaca gtgtcagtac acttatgcac tggtaccaac agaaaccagg    3240
acagcaaccc aaactcctca tctatctagc atcacaccta gaatctgggg tccctgccag    3300
gttcagtggc agtgggtctg ggacagactt caccctcacc attgatcctg tggaggctga    3360
```

```
tgacactgca acctattact gtcagcagag ttggaatgat ccgtggacgt tcggtggagg    3420
caccaagctg gaattgaaaa atggggccgt cgagcaccac caccaccacc actgagtcga    3480
ggatcaattc cgcccctctc cctcccccc  cctaacgtt  actggccgaa gccgcttgga    3540
ataaggccgg tgtgcgtttg tctatatgtt attttccacc atattgccgt cttttggcaa    3600
tgtgagggcc cggaaacctg gccctgtctt cttgacgagc attcctaggg gtctttcccc    3660
tctcgccaaa ggaatgcaag gtctgttgaa tgtcgtgaag gaagcagttc ctctggaagc    3720
ttcttgaaga caaacaacgt ctgtagcgac cctttgcagg cagcggaacc ccccacctgg    3780
cgacaggtgc ctctgcggcc aaaagccacg tgtataagat acacctgcaa aggcggcaca    3840
accccagtgc cacgttgtga gttggatagt tgtggaaaga gtcaaatggc tctcctcaag    3900
cgtattcaac aaggggctga aggatgccca aaggtaccc  cattgtatgg gatctgatct    3960
ggggcctcgg tgcacatgct ttacatgtgt ttagtcgagg ttaaaaaacg tctaggcccc    4020
ccgaaccacg gggacgtggt tttcctttga aaaacacgat aataccatga ttgaacaaga    4080
tggattgcac gcaggttctc cggccgcttg ggtggagagg ctattcggct atgactgggc    4140
acaacagaca atcggctgct ctgatgccgc cgtgttccgg ctgtcagcgc aggggcgccc    4200
ggttcttttt gtcaagaccg acctgtccgg tgccctgaat gaactgcagg acgaggcagc    4260
gcggctatcg tggctggcca cgacgggcgt tccttgcgca gctgtgctcg acgttgtcac    4320
tgaagcggga agggactggc tgctattggg cgaagtgccg gggcaggatc tcctgtcatc    4380
tcaccttgct cctgccgaga aagtatccat catggctgat gcaatgcggc ggctgcatac    4440
gcttgatccg gctacctgcc cattcgacca ccaagcgaaa catcgcatcg agcgagcacg    4500
tactcggatg gaagccggtc ttgtcgatca ggatgatctg gacgaagagc atcaggggct    4560
cgcgccagcc gaactgttcg ccaggctcaa ggcgcgcatg cccgacggcg aggatctcgt    4620
cgtgacccat ggcgatgcct gcttgccgaa tatcatggtg aaaatggcc  gcttttctgg    4680 attcatcgac tgtggccggc tgggtgtggc ggaccgctat caggacatag cgttggctac    4740
ccgtgatatt gctgaagagc ttggcggcga atgggctgac cgcttcctcg tgctttacgg    4800
tatcgccgct cccgattcgc agcgcatcgc cttctatcgc cttcttgacg agttcttctg    4860
agcgggactc tggggatccg ataaaataaa agattttatt tagtctccag aaaaagggggg    4920 gaatgaaaga ccccacctgt aggtttggca agctagctta agtaacgcca ttttgcaagg    4980
catggaaaaa tacataactg agaatagaga agttcagatc aaggtcagga acagatggaa    5040
cagctgaata tgggccaaac aggatatctg tggtaagcag ttcctgcccc ggctcagggc    5100
caagaacaga tggaacagct gaatatgggc caaacaggat atctgtggta agcagttcct    5160
gccccggctc agggccaaga acagatggtc cccagatgcg gtccagccct cagcagtttc    5220
tagagaacca tcagatgttt ccagggtgcc ccaaggacct gaaatgaccc tgtgccttat    5280
ttgaactaac caatcagttc gcttctcgct tctgttcgcg cgcttctgct ccccgagctc    5340
aataaaagag cccacaaccc ctcactcggg gcgccagtcc tccgattgac tgagtcgccc    5400
gggtacccgt gtatccaata aaccctcttg cagttgcatc cgacttgtgg tctcgctgtt    5460
ccttgggagg gtctcctctg agtgattgac tacccgt                             5497
```

<210> SEQ ID NO 24
<211> LENGTH: 5368
<212> TYPE: DNA
<213> ORGANISM: Artificial Sequence
<220> FEATURE:
<223> OTHER INFORMATION: BEAT 2 vector

<400> SEQUENCE: 24

```
gaattaattc ataccagatc accgaaaact gtcctccaaa tgtgtccccc tcacactccc        60
aaattcgcgg gcttctgctc ttagaccact ctaccctatt ccccacactc accggagcca       120
aagccgcggc ccttccgttt cttgctttt gaaagacccc acccgtaggt ggcaagctag        180
cttaagtaac gccactttgc aaggcatgga aaatacata actgagaata ggaaagttca       240
gatcaaggtc aggaacaaag aaacagctga ataccaaaca ggatatctgt ggtaagcggt       300
tcctgccccg gctcagggcc aagaacagat gagacagctg agtgatgggc caaacaggat       360
atctgtggta agcagttcct gccccggctc ggggccaaga acagatggtc ccagatgcg        420
gtccagccct cagcagtttc tagtgaatca tcagatgttt ccagggtgcc caaggacct        480
gaaaatgacc ctgtacctta tttgaactaa ccaatcagtt cgcttctcgc ttctgttcgc       540
gcgcttccgc tctccgagct caataaaaga gcccacaacc cctcactcgg cgcgccagtc       600
ttccgataga ctgcgtcgcc cgggtacccg tattcccaat aaagcctctt gctgtttgca       660
tccgaatcgt ggtctcgctg ttccttggga gggtctcctc tgagtgattg actacccacg       720
acggggtct ttcatttggg ggctcgtccg ggatttggag acccctgccc agggaccacc        780
gacccaccac cgggaggtaa gctggccagc aacctatctg tgtctgtccg attgtctagt       840
gtctatgttt gatgttatgc gcctgcgtct gtactagtta gctaactagc tctgtatctg       900
gcggacccgt ggtggaactg acgagttctg aacacccggc cgcaacccag ggagacgtcc       960
cagggacttt gggggccgtt tttgtggccc gacctgagga agggagtcga tgtggaatcc      1020
gacccgtca ggatatgtgg ttctggtagg agacgagaac ctaaaacagt tcccgcctcc       1080
gtctgaattt ttgcttcgg tttggaaccg aagccgcgcg tcttgtctgc tgcagcatcg       1140
ttctgtgttg tctctgtctg actgtgttc tgtatttgtc tgaaaattag ggccagactg       1200
ttaccactcc cttaagtttg accttaggtc actggaaaga tgtcgagcgg atcgctcaca       1260
accagtcggt agatgtcaag aagagacgtt gggttaccct ctgctctgca gaatggccaa       1320
cctttaacgt cggatggccg cgagacggca ccttttaaccg agacctcatc acccaggtta       1380
agatcaaggt cttttcacct ggcccgcatg gacacccaga ccaggtcccc tacatcgtga       1440
cctgggaagc cttggctttt gacccccctc cctgggtcaa gccctttgta caccctaagc       1500
ctccgcctcc tcttcctcca tccgcccgt ctctccccct tgaacctcct cgttcgaccc       1560
cgcctcgatc ctcctttat ccagccctca ctccttctct aggcgccgga attccggccg       1620
tgacaagagt tactaacagc ccctctctcc aagctcactt acaggctctc tacttagtcc       1680
agcacgaagt ctggagacct ctggcggcag cctaccaaga caactggac cgaccggtgg       1740
tacctcaccc ttaccgagtc ggcgacacag tgtgggtccg ccgacaccag actaagaacc       1800
tagaacctcg ctggaaagga ccttacacag tcctgcagac caccccccacc gccctcaaag      1860
tagacggcat cgcagcttgg atacacgccg cccacgtgaa ggctgccgac cccggggtg        1920
gaccatctct agactgacgc ggccgcccac cgaggtgcac ctggtggagt ctggggaga       1980
cttagtgaag cctggagggt ccctgaaact ctcctgtgca gcctctggat tcactttcag       2040
tcactatggc atgtcttggg ttcgccagac tccagacaag aggctggagt gggtcgcaac       2100
cattggtagt cgtggtactt acacccacta tccagacagt gtgaagggac gattcaccat       2160
ctccagagac aatgacaaga acgccctgta cctgcaaatg aacagtctga agtctgaaga       2220
cacagccatg tattactgtg caagaagaag tgaatttat tactacggta ataccactacta      2280
```

```
ttactctgct atggactact ggggtcaagg agcctcagtc accgtctcct caggtggagg    2340
cggttcaggc ggaggtggct ctggcggtgg cggatcggac attgtgctga cccaatctcc    2400
agcttctttg gctgtatctc taggacagag ggccaccatc tcctgcagag ccagcgaaag    2460
tgttgataat tatggcttta gttttatgaa ctggttccaa cagaaaccag acagccacc     2520
caaactcctc atctatgcta tatccaaccg aggatccggg gtccctgcca ggtttagtgg    2580
cagtgggtct gggacagact tcagcctcaa catccatcct gtagaggagg atgatcctgc    2640
aatgtatttc tgtcagcaaa ctaaggaggt tccgtggacg ttcggtggag gcaccaagct    2700
ggaaatcaaa ggtggaggcg gttcagaggt gcagcttcag gagtcaggac ctggccttgt    2760
gaaaccctca cagtcactct ccctcacctg ttctgtcact gcttacttca tcactagtaa    2820
ttactgggcc tggatccgga agttcccagg aaataaaatg gagtggatgg acacataac     2880
ctacagtggt tacactacct acaatccatc tctcaaaagt cgaatctcca ttactagaga    2940
cacatcgagg aatcagttct tcctccagtt gaactctgta actactgagg acacagccac    3000
ttattactgt gcaagaggtg gaggcggttc aggcggaggt ggctctggcg gtggcggatc    3060
gaacattgta atgacccaat ctcccaaatc catgtccatg tcagtaggag agagggtcac    3120
cttgacctgc aaggccagtg agaatgtggt tacttatgtt tcctggtatc aacagaaacc    3180
agagcagtct cctaaactgc tgatatacgg ggcatccaac cggtacactg gggtcccga    3240
tcgcttcaca ggcagtggat ctgcaacaga tttcactctg accatcagca gtgtgcaggc    3300
tgaagacctt gcagattatc actgtggaca gggttacagc tatccggtcg aggatcaatt    3360
ccgcccctct ccctccccc ccctaacgt tactggccga agccgcttgg aataaggccg     3420
gtgtgcgttt gtctatatgt tattttccac catattgccg tcttttggca atgtgagggc    3480
ccggaaacct ggccctgtct tcttgacgag cattcctagg ggtctttccc ctctcgccaa    3540
aggaatgcaa ggtctgttga atgtcgtgaa ggaagcagtt cctctggaag cttcttgaag    3600
acaaacaacg tctgtagcga cccttttgcag gcagcggaac cccccacctg gcgacaggtg    3660
cctctgcggc caaaagccac gtgtataaga tacacctgca aaggcggcac aaccccagtg    3720
ccacgttgtg agttggatag ttgtggaaag agtcaaatgg ctctcctcaa gcgtattcaa    3780
caaggggctg aaggatgccc agaaggtacc ccattgtatg ggatctgatc tggggcctcg    3840
gtgcacatgc tttacatgtg tttagtcgag gttaaaaaac gtctaggccc ccgaaccac     3900
ggggacgtgg ttttcctttg aaaaacacga taataccatg attgaacaag atggattgca    3960
cgcaggttct ccggccgctt gggtggagag gctattcggc tatgactggg cacaacagac    4020
aatcggctgc tctgatgccg ccgtgttccg gctgtcagcg caggggcgcc cggttctttt    4080
tgtcaagacc gacctgtccg gtgccctgaa tgaactgcag gacgaggcag cgcggctatc    4140
gtggctggcc acgacgggcg ttccttgcgc agctgtgctc gacgttgtca ctgaagcggg    4200
aagggactgg ctgctattgg gcgaagtgcc ggggcaggat ctcctgtcat ctcaccttgc    4260
tcctgccgag aaagtatcca tcatggctga tgcaatgcgg cggctgcata cgcttgatcc    4320
ggctacctgc ccattcgacc accaagcgaa acatcgcatc gagcgagcac gtactcggat    4380
ggaagccggt cttgtcgatc aggatgatct ggacgaagag catcagggc tcgcgccagc    4440
cgaactgttc gccaggctca aggcgcgcat gcccgacggc gaggatctcg tcgtgaccca    4500
tggcgatgcc tgcttgccga atatcatggt ggaaaatggc cgcttttctg gattcatcga    4560
ctgtggccgc tgggtgtgg cggaccgcta tcaggacata gcgttggcta cccgtgatat    4620
tgctgaagag cttggcggcg aatgggctga ccgcttcctc gtgctttacg gtatcgccgc    4680
```

-continued

```
tcccgattcg cagcgcatcg ccttctatcg ccttcttgac gagttcttct gagcgggact    4740
ctggggatcc gataaaataa aagattttat ttagtctcca gaaaaagggg ggaatgaaag    4800
accccacctg taggtttggc aagctagctt aagtaacgcc attttgcaag gcatggaaaa    4860
atacataact gagaatagag aagttcagat caaggtcagg aacagatgga acagctgaat    4920
atgggccaaa caggatatct gtggtaagca gttcctgccc cggctcaggg ccaagaacag    4980
atggaacagc tgaatatggg ccaaacagga tatctgtggt aagcagttcc tgccccggct    5040
cagggccaag aacagatggt ccccagatgc ggtccagccc tcagcagttt ctagagaacc    5100
atcagatgtt tccagggtgc cccaaggacc tgaaatgacc ctgtgcctta tttgaactaa    5160
ccaatcagtt cgcttctcgc ttctgttcgc gcgcttctgc tccccgagct caataaaaga    5220
gcccacaacc cctcactcgg ggcgccagtc ctccgattga ctgagtcgcc cgggtacccg    5280
tgtatccaat aaaccctctt gcagttgcat ccgacttgtg gtctcgctgt tccttgggag    5340
ggtctcctct gagtgattga ctacccgt                                       5368

<210> SEQ ID NO 25
<211> LENGTH: 5515
<212> TYPE: DNA
<213> ORGANISM: Artificial Sequence
<220> FEATURE:
<223> OTHER INFORMATION: BEAT 3 vector

<400> SEQUENCE: 25
gaattaattc ataccagatc accgaaaact gtcctccaaa tgtgtccccc tcacactccc      60
aaattcgcgg gcttctgctc ttagaccact ctaccctatt ccccacactc accggagcca     120
aagccgcggc ccttccgttt ctttgctttt gaaagacccc accgtaggt ggcaagctag      180 cttaagtaac gccactttgc aaggcatgga aaaatacata actgagaata ggaaagttca     240
gatcaaggtc aggaacaaag aaacagctga ataccaaaca ggatatctgt ggtaagcggt     300
tcctgccccg gctcagggcc aagaacagat gagacagctg agtgatgggc aaacaggat     360 atctgtggta agcagttcct gccccggctc ggggccaaga acagatggtc ccagatgcg     420 gtccagccct cagcagtttc tagtgaatca tcagatgttt ccagggtgcc ccaaggacct     480
gaaaatgacc ctgtacccta tttgaactaa ccaatcagtt cgcttctcgc ttctgttcgc     540
gcgcttccgc tctccgagct caataaaaga gcccacaacc cctcactcgg cgcgccagtc     600
ttccgataga ctgcgtcgcc cgggtacccg tattcccaat aaagcctctt gctgtttgca     660
tccgaatcgt ggtctcgctg ttccttggga gggtctcctc tgagtgattg actacccacg     720 acggggggtct ttcatttggg ggctcgtccg ggatttggag accctgcccc agggaccacc     780
gacccaccac cggaggtaa gctggccagc aacctatctg tgtctgtccg attgtctagt     840
gtctatgttt gatgttatgc gcctgcgtct gtactagtta gctaactagc tctgtatctg     900
gcggacccgt ggtggaactg acgagttctg aacaccggc cgcaacccag ggagacgtcc     960
cagggacttt gggggccgtt tttgtggccc gacctgagga agggagtcga tgtggaatcc    1020
gaccccgtca ggatatgtgg ttctggtagg agacgagaac ctaaaacagt tcccgcctcc    1080
gtctgaattt ttgctttcgg tttggaaccg aagccgcgcg tcttgtctgc tgcagcatcg    1140
ttctgtgttg tctctgtctg actgtgtttc tgtatttgtc tgaaaattag ggccagactg    1200
ttaccactcc cttaagtttg accttaggtc actggaaaga tgtcgagcgg atcgctcaca    1260
accagtcggt agatgtcaag aagagacgtt gggttacctt ctgctctgca gaatggccaa    1320
```

```
cctttaacgt cggatggccg cgagacggca cctttaaccg agacctcatc acccaggtta    1380
agatcaaggt cttttcacct ggcccgcatg gacacccaga ccaggtcccc tacatcgtga    1440
cctgggaagc cttggctttt gaccccctc cctgggtcaa gccctttgta caccctaagc    1500
ctccgcctcc tcttcctcca tccgcccgt ctctcccct tgaacctcct cgttcgaccc    1560
cgcctcgatc ctcccttat ccagccctca ctccttctct aggcgccgga attccggccg    1620
tgacaagagt tactaacagc ccctctctcc aagctcactt acaggctctc tacttagtcc    1680
agcacgaagt ctggagacct ctggcggcag cctaccaaga caactggac cgaccggtgg    1740 tacctcaccc ttaccgagtc ggcgacacag tgtgggtccg ccgacaccag actaagaacc    1800
tagaacctcg ctggaaagga ccttacacag tcctgcagac caccccacc gccctcaaag    1860 tagacggcat cgcagcttgg atacacgccg cccacgtgaa ggctgccgac cccggggtg    1920 gaccatctct agactgacgc ggccgcccac catggagaca gacacactcc tgctatgggt    1980
actgctgctc tgggttccag ttccactgg tgacgaggtg cagctggtgg agtctgggg    2040 aggcttggtg cagcctggaa agtccctgaa actctcctgt gaggcctctg gattcacctt    2100
cagcggctat ggcatgcact gggtccgcca ggctccaggg aggggctgg agtcggtcgc    2160 atacattact agtagtagta ttaatatcaa atatgctgac gctgtgaaag gccggttcac    2220
cgtctccaga gacaatgcca agaacttact gtttctacaa atgaacattc tcaagtctga    2280
ggacacagcc atgtactact gtgcaagatt cgactggaca aaaaattact ggggccaagg    2340
aaccatggtc accgtctcct caggtggagg cggttcaggc ggaggtggct ctggcggtgg    2400
cggatcggac atccagatga cccagtctcc atcatcactg cctgcctccc tgggagacag    2460
agtcactatc aattgtcagg ccagtcagga cattagcaat tatttaaact ggtaccagca    2520
gaaaccaggg aaagctccta agctcctgat ctattataca aataaattgg cagatggagt    2580
cccatcaagg ttcagtggca gtggttctgg gagagattct ctttcacta tcagcagcct    2640 ggaatccgaa gatattggat cttattactg tcaacagtat tataactatc cgtgacgtt    2700 cggacctggc accaagctgg aaatcaaagg tggaggcggt tcaatggagg tgcaggtggt    2760
ggagtctgat ggaggcttag tgcagcctgg aaggtcccta aaactcccct gtgcagcctc    2820
aggattcact ttcagtgact attacatggc ctgggtccgc caggctccaa cgaagggct    2880 ggagtgggtc gcaagcatta gttatgatgg tagtagcact tactatcgag actccgtgaa    2940
gggccgattc actatctcca gagataatgc aaaaagcacc ctatacctgc aaatggacag    3000
tctgaggtct gaggacacgg ccacttatta ctgcggaaga cacagtagct actttgatta    3060
ctggggccaa ggagtcatgg tcacagtctc ctcaggtgga ggcggttcag gcggaggtgg    3120
ctctggcggt ggcggatcgg acactgtact gacccagtct cctgctttgg ctgtgtctcc    3180
aggagagagg gttaccatct cctgtagggc cagtgacagt gtcagtacac ttatgcactg    3240
gtaccaacag aaaccaggac agcaacccaa actcctcatc tatctagcat cacacctaga    3300
atctggggtc cctgccaggt tcagtggcag tgggtctggg acagacttca ccctcaccat    3360
tgatcctgtg gaggctgatg acactgcaac ctattactgt cagcagagtt ggaatgatcc    3420
gtggacgttc ggtggaggca ccaagctgga attgaaaaat ggggccgtcg agcaccacca    3480
ccaccaccac tgagtcgagg atcaattccg ccctctccc tccccccccc ctaacgttac    3540
tggccgaagc cgcttggaat aaggccggtg tgcgtttgtc tatatgttat tttccaccat    3600
attgccgtct tttggcaatg tgagggcccg gaaacctggc cctgtcttct tgacgagcat    3660
tcctaggggt cttcccctc tcgccaaagg aatgcaaggt ctgttgaatg tcgtgaagga    3720
```

```
agcagttcct ctggaagctt cttgaagaca acaacgtct gtagcgaccc tttgcaggca    3780
gcggaacccc ccacctggcg acaggtgcct ctgcggccaa agccacgtg tataagatac    3840 acctgcaaag gcggcacaac cccagtgcca cgttgtgagt tggatagttg tggaaagagt    3900
caaatggctc tcctcaagcg tattcaacaa ggggctgaag gatgcccaga aggtacccca    3960
ttgtatggga tctgatctgg ggcctcggtg cacatgcttt acatgtgttt agtcgaggtt    4020
aaaaaacgtc taggccccc gaaccacggg gacgtggttt cctttgaaa acacgataa     4080 taccatgatt gaacaagatg gattgcacgc aggttctccg gccgcttggg tggagaggct    4140
attcggctat gactgggcac aacagacaat cggctgctct gatgccgccg tgttccggct    4200
gtcagcgcag gggcgcccgg ttcttttgt caagaccgac ctgtccggtg ccctgaatga    4260
actgcaggac gaggcagcgc ggctatcgtg gctggccacg acgggcgttc cttgcgcagc    4320
tgtgctcgac gttgtcactg aagcgggaag gactggctg ctattgggcg aagtgccggg    4380
gcaggatctc ctgtcatctc accttgctcc tgccgagaaa gtatccatca tggctgatgc    4440
aatgcggcgg ctgcatacgc ttgatccggc tacctgccca ttcgaccacc aagcgaaaca    4500
tcgcatcgag cgagcacgta ctcggatgga agccggtctt gtcgatcagg atgatctgga    4560
cgaagagcat caggggctcg cgccagccga actgttcgcc aggctcaagg cgcgcatgcc    4620
cgacggcgag gatctcgtcg tgacccatgg cgatgcctgc ttgccgaata tcatggtgga    4680
aaatggccgc ttttctggat tcatcgactg tggccggctg ggtgtggcgg accgctatca    4740
ggacatagcg ttggctaccc gtgatattgc tgaagagctt ggcggcgaat gggctgaccg    4800
cttcctcgtg ctttacggta tcgccgctcc cgattcgcag cgcatcgcct tctatcgcct    4860
tcttgacgag ttcttctgag cgggactctg gggatccgat aaaataaaag atttttattta    4920 gtctccagaa aaggggggga atgaaagacc ccacctgtag gtttggcaag ctagcttaag    4980
taacgccatt ttgcaaggca tggaaaaata cataactgag aatagagaag ttcagatcaa    5040
ggtcaggaac agatggaaca gctgaatatg gccaaacag gatatctgtg gtaagcagtt    5100
cctgccccgg ctcagggcca agaacagatg gaacagctga atatgggcca acaggatat    5160 ctgtggtaag cagttcctgc cccggctcag ggccaagaac agatggtccc cagatgcggt    5220
ccagccctca gcagtttcta gagaaccatc agatgtttcc agggtgcccc aaggacctga    5280
aatgaccctg tgccttattt gaactaacca atcagttcgc ttctcgcttc tgttcgcgcg    5340
cttctgctcc ccgagctcaa taaaagagcc cacaacccct cactcggggc gccagtcctc    5400
cgattgactg agtcgcccgg gtacccgtgt atccaataaa ccctcttgca gttgcatccg    5460
acttgtggtc tcgctgttcc ttgggagggt ctcctctgag tgattgacta cccgt         5515
```

<210> SEQ ID NO 26
<211> LENGTH: 5386
<212> TYPE: DNA
<213> ORGANISM: Artificial Sequence
<220> FEATURE:
<223> OTHER INFORMATION: BEAT 4 vector

<400> SEQUENCE: 26

```
gaattaattc ataccagatc accgaaaact gtcctccaaa tgtgtccccc tcacactccc      60
aaattcgcgg gcttctgctc ttagaccact ctaccctatt ccccacactc accggagcca     120
aagccgcggc ccttccgttt cttgctttt gaaagacccc acccgtaggt ggcaagctag     180
cttaagtaac gccactttgc aaggcatgga aaatacata actgagaata ggaaagttca     240
```

-continued

```
gatcaaggtc aggaacaaag aaacagctga ataccaaaca ggatatctgt ggtaagcggt      300
tcctgccccg gctcagggcc aagaacagat gagacagctg agtgatgggc caaacaggat      360
atctgtggta agcagttcct gccccggctc ggggccaaga acagatggtc cccagatgcg      420
gtccagccct cagcagtttc tagtgaatca tcagatgttt ccagggtgcc caaggacct      480 gaaaatgacc ctgtacctta tttgaactaa ccaatcagtt cgcttctcgc ttctgttcgc      540
gcgcttccgc tctccgagct caataaaaga gcccacaacc cctcactcgg cgcgccagtc      600
ttccgataga ctgcgtcgcc cgggtacccg tattcccaat aaagcctctt gctgtttgca      660
tccgaatcgt ggtctcgctg ttccttggga gggtctcctc tgagtgattg actacccacg      720 acggggtct ttcatttggg ggctcgtccg ggatttggag acccctgccc agggaccacc      780
gacccaccac cggaggtaa gctggccagc aacctatctg tgtctgtccg attgtctagt      840
gtctatgttt gatgttatgc gcctgcgtct gtactagtta gctaactagc tctgtatctg      900
gcggacccgt ggtggaactg acgagttctg aacacccggc cgcaacccag ggagacgtcc      960
cagggacttt gggggccgtt tttgtggccc gacctgagga agggagtcga tgtggaatcc     1020
gaccccgtca ggatatgtgg ttctggtagg agacgagaac ctaaaacagt tcccgcctcc     1080
gtctgaattt ttgctttcgg tttggaaccg aagccgcgcg tcttgtctgc tgcagcatcg     1140
ttctgtgttg tctctgtctg actgtgtttc tgtatttgtc tgaaaattag gccagactg     1200 ttaccactcc cttaagtttg acctaggtc actggaaaga tgtcgagcgg atcgctcaca     1260
accagtcggt agatgtcaag aagagacgtt gggttacctt ctgctctgca gaatggccaa     1320
cctttaacgt cggatggccg cgagacggca cctttaaccg agacctcatc acccaggtta     1380
agatcaaggt cttttcacct ggcccgcatg gacacccaga ccaggtcccc tacatcgtga     1440
cctgggaagc cttggcttt gacccccctc cctgggtcaa gcccttgta cacctaagc     1500 ctccgcctcc tcttcctcca tccgccccgt ctctcccct tgaacctcct cgttcgaccc     1560
cgcctcgatc ctccctttat ccagcccca ctccttctct aggcgccgga attccggccg     1620
tgacaagagt tactaacagc ccctctctcc aagctcactt acaggctctc tacttagtcc     1680
agcacgaagt ctggagacct ctggcggcag cctaccaaga acaactggac cgaccggtgg     1740
tacctcaccc ttaccgagtc ggcgacacag tgtgggtccg ccgacaccag actaagaacc     1800
tagaacctcg ctgaaagga ccttacacag tcctgcagac caccccccacc gccctcaaag     1860 tagacggcat cgcagcttgg atacacgccg cccacgtgaa ggctgccgac cccgggggtg     1920
gaccatctct agactgacgc ggccgcccac catggagaca gacacactcc tgctatgggt     1980
actgctgctc tgggttccag gttccactgg tgacgaggtg cagctggtgg agtctggggg     2040
aggcttggtg cagcctggaa agtccctgaa actctcctgt gaggcctctg gattcacctt     2100
cagcggctat ggcatgcact gggtccgcca ggctccaggg aggggctgg agtcggtcgc     2160 atacattact agtagtagta ttaatatcaa atatgctgac gctgtgaaag gccggttcac     2220
cgtctccaga gacaatgcca agaacttact gtttctacaa atgaacattc tcaagtctga     2280
ggacacagcc atgtactact gtgcaagatt cgactggggac aaaaattact ggggccaagg     2340
aaccatggtc accgtctcct caggtggagg cggttcaggc ggaggtggct ctggcggtgg     2400
cggatcggac atccagatga cccagtctcc atcatcactg cctgcctccc tgggagacag     2460
agtcactatc aattgtcagg ccagtcagga cattagcaat tatttaaact ggtaccagca     2520
gaaaccaggg aaagctccta agctcctgat ctattataca aataaattgg cagatggagt     2580
cccatcaagg ttcagtggca gtggttctgg gagagattct tctttcacta tcagcagcct     2640
```

```
ggaatccgaa gatattggat cttattactg tcaacagtat tataactatc cgtggacgtt    2700
cggacctggc accaagctgg aaatcaaagg tggaggcggt tcagaggtgc agcttcagga    2760
gtcaggacct ggccttgtga aaccctcaca gtcactctcc ctcacctgtt ctgtcactgc    2820
ttacttcatc actagtaatt actgggcctg gatccggaag ttcccaggaa ataaaatgga    2880
gtggatggga cacataacct acagtggtta cactacctac aatccatctc tcaaaagtcg    2940
aatctccatt actagagaca catcgaggaa tcagttcttc ctccagttga actctgtaac    3000
tactgaggac acagccactt attactgtgc aagaggtgga ggcggttcag gcggaggtgg    3060
ctctggcggt ggcggatcga acattgtaat gacccaatct cccaaatcca tgtccatgtc    3120
agtaggagag agggtcaccc tgacctgcaa ggccagtgag aatgtggtta cttatgtttc    3180
ctggtatcaa cagaaaccag agcagtctcc taaactgctg atatacgggg catccaaccg    3240
gtacactggg gtccccgatc gcttcacagg cagtggatct gcaacagatt tcactctgac    3300
catcagcagt gtgcaggctg aagaccttgc agattatcac tgtggacagg ttacagcta    3360
tccggtcgag gatcaattcc gcccctctcc ctcccccccc cctaacgtta ctggccgaag    3420
ccgcttggaa taaggccggt gtgcgtttgt ctatatgtta ttttccacca tattgccgtc    3480
ttttggcaat gtgagggccc ggaaacctgg ccctgtcttc ttgacgagca ttcctagggg    3540
tctttcccct ctcgccaaag gaatgcaagg tctgttgaat gtcgtgaagg aagcagttcc    3600
tctggaagct tcttgaagac aaacaacgtc tgtagcgacc ctttgcaggc agcggaaccc    3660
cccacctggc gacaggtgcc tctgcggcca aaagccacgt gtataagata cacctgcaaa    3720
ggcggcacaa ccccagtgcc acgttgtgag ttggatagtt gtggaaagag tcaaatggct    3780
ctcctcaagc gtattcaaca aggggctgaa ggatgcccag aaggtacccc attgtatggg    3840
atctgatctg gggcctcggt gcacatgctt tacatgtgtt tagtcgaggt taaaaaacgt    3900
ctaggccccc cgaaccacgg ggacgtggtt ttcctttgaa aaacacgata taccatgat     3960
tgaacaagat ggattgcacg caggttctcc ggccgcttgg gtggagaggc tattcggcta    4020
tgactgggca caacagacaa tcggctgctc tgatgccgcc gtgttccggc tgtcagcgca    4080
ggggcgcccg gttctttttg tcaagaccga cctgtccggt gccctgaatg aactgcagga    4140
cgaggcagcg cggctatcgt ggctggccac gacgggcgtt ccttgcgcag ctgtgctcga    4200
cgttgtcact gaagcgggaa gggactggct gctattgggc gaagtgccgg ggcaggatct    4260
cctgtcatct caccttgctc ctgccgagaa agtatccatc atggctgatg caatgcggcg    4320
gctgcatacg cttgatccgg ctacctgccc attcgaccac caagcgaaac atcgcatcga    4380
gcgagcacgt actcggatgg aagccggtct tgtcgatcag gatgatctgg acgaagagca    4440
tcagggctc gcgccagccg aactgttcgc caggctcaag gcgcgcatgc ccgacggcga    4500
ggatctcgtc gtgacccatg gcgatgcctg cttgccgaat atcatggtgg aaaatggccg    4560
cttttctgga ttcatcgact gtggccggct gggtgtggcg gaccgctatc aggacatagc    4620
gttggctacc cgtgatattg ctgaagagct tggcggcgaa tgggctgacc gcttcctcgt    4680
gctttacggt atcgccgctc ccgattcgca gcgcatcgcc ttctatcgcc ttcttgacga    4740
gttcttctga gcgggactct ggggatccga taaaataaaa gatttatttt agtctccaga    4800
aaaggggggg aatgaaagac cccacctgta ggtttggcaa gctagcttaa gtaacgccat    4860
tttgcaaggc atgaaaaat acataactga gaatagagaa gttcagatca aggtcaggaa     4920
cagatggaac agctgaatat gggccaaaca ggatatctgt ggtaagcagt tcctgccccg    4980
```

```
gctcagggcc aagaacagat ggaacagctg aatatgggcc aaacaggata tctgtggtaa    5040
gcagttcctg ccccggctca gggccaagaa cagatggtcc ccagatgcgg tccagccctc    5100
agcagtttct agagaaccat cagatgtttc cagggtgccc caaggacctg aaatgaccct    5160
gtgccttatt tgaactaacc aatcagttcg cttctcgctt ctgttcgcgc gcttctgctc    5220
cccgagctca ataaaagagc ccacaacccc tcactcgggg cgccagtcct ccgattgact    5280
gagtcgcccg ggtacccgtg tatccaataa accctcttgc agttgcatcc gacttgtggt    5340
ctcgctgttc cttgggaggg tctcctctga gtgattgact acccgt                   5386
```